(12) United States Patent
Bellgard et al.

(10) Patent No.: US 8,992,938 B2
(45) Date of Patent: Mar. 31, 2015

(54) **GENES AND PROTEINS OF *BRACHYSPIRA HYODYSENTERIAE* AND USES TH

GENES AND PROTEINS OF *BRACHYSPIRA HYODYSENTERIAE* AND USES THEREOF

FIELD OF INVENTION

This invention relates to novel genes in *Brachyspira hyodysenteriae* and the proteins encoded therein. This invention further relates to use of these novel genes and proteins for diagnosis of *B. hyodysenteriae* disease, vaccines against *B. hyodysenteriae* and for screening for compounds that kill *B. hyodysenteriae* or block the pathogenic effects of *B. hyodysenteriae*. These sequences may also be useful for diagnostic and therapeutic and/or prophylactic treatment of diseases in animals caused by other *Brachyspira* species, including *B. suanatina, B. intermedia, B. alvinipulli, B. aalborgi, B. innocens, B. murdochii,* and *B. pilosicoli*.

BACKGROUND OF INVENTION

Swine dysentery is a significant endemic disease of pigs in Australia and worldwide. Swine dysentery is a contagious mucohaemorrhagic diarrhoeal disease, characterised by extensive inflammation and necrosis of the epithelial surface of the large intestine. Economic losses due to swine dysentery result mainly from growth retardation, costs of medication and mortality. The causative agent of swine dysentery was first identified as an anaerobic spirochaete (*Treponema hyodysenteriae*) in 1971, and was recently reassigned to the genus *Brachyspira* as *B. hyodysenteriae*. Where swine dysentery is established in a piggery, the disease spectrum can vary from being mild, transient or unapparent, to being severe and even fatal. Medication strategies on individual piggeries may mask clinical signs and on some piggeries the disease may go unnoticed, or may only be suspected. Whether or not obvious disease occurs, *B. hyodysenteriae* may persist in infected pigs, or in other reservoir hosts such as rodents, or in the environment. All these sources pose potential for transmission of the disease to uninfected herds. Commercial poultry may also be colonized by *B. hyodysenteriae*, although it is not clear how commonly this occurs under field conditions.

Colonisation by *B. hyodysenteriae* elicits a strong immunological response against the spirochaete, hence indirect evidence of exposure to the spirochaete can be obtained by measuring circulating antibody titres in the blood of infected animals. These antibody titres have been reported to be maintained at low levels, even in animals that have recovered from swine dysentery. Serological tests for detection of antibodies therefore have considerable potential for detecting subclinical infections and recovered carrier pigs that have undetectable numbers of spirochaetes in their large intestines. These tests would be particularly valuable in an easy to use kit form, such as an enzyme-linked immunosorbent assay. A variety of techniques have been developed to demonstrate the presence of circulating antibodies against *B. hyodysenteriae*, including indirect fluorescent antibody tests, haemagglutination tests, microtitration agglutination tests, complement fixation tests, and ELISA using either lipopolysaccharide or whole sonicated spirochaetes as antigen. All these tests have suffered from problems of specificity, as related non-pathogenic intestinal spirochaetes can induce cross-reactive antibodies. These tests are useful for detecting herds where there is obvious disease and high circulating antibody titres, but they are problematic for identifying sub-clinically infected herds and individual infected pigs. Consequently, to date, no completely sensitive and specific assays are available for the detection of antibodies against *B. hyodysenteriae*. The lack of suitable diagnostic tests has hampered control of swine dysentery.

A number of methods are employed to control swine dysentery, varying from the prophylactic use of antimicrobial agents, to complete destocking of infected herds and prevention of re-entry of infected carrier pigs. All these options are expensive and, if they are to be fully effective, they require the use of sophisticated diagnostic tests to monitor progress. Currently, detection of swine dysentery in herds with subclinical infections, and individual healthy carrier animals, remains a major problem and is hampering implementation of effective control measures. A definitive diagnosis of swine dysentery traditionally has required the isolation and identification of *B. hyodysenteriae* from the faeces or mucosa of diseased pigs. Major problems involved include the slow growth and fastidious nutritional requirements of these anaerobic bacteria and confusion due to the presence of morphologically similar spirochaetes in the normal flora of the pig intestine. A significant improvement in the diagnosis of individual affected pigs was achieved with the development of polymerase chain reaction (PCR) assays for the detection of spirochaetes from faeces. Unfortunately in practical applications the limit of detection of PCRs rendered it unable to detect carrier animals with subclinical infections. As a consequence of these diagnostic problems, there is a clear need to develop a simple and effective diagnostic tool capable of detecting *B. hyodysenteriae* infection at the herd and individual pig level.

A strong immunological response is induced against the spirochaete following colonization with *B. hyodysenteriae*, and pigs recovered from swine dysentery are protected from re-infection. Despite this, attempts to develop vaccines to control swine dysentery have met with very limited success, either because they have provided inadequate protection on a herd basis, or they have been too costly and difficult to produce to make them commercially viable. Bacterin vaccines provide some level of protection, but they tend to be lipopolysaccharide serogroup-specific, which then requires the use of multivalent bacterins. Furthermore they are difficult and costly to produce on a large scale because of the fastidious anaerobic growth requirements of the spirochaete.

Several attempts have been made to develop attenuated live vaccines for swine dysentery. This approach has the disadvantage that attenuated strains show reduced colonisation, and hence cause reduced immune stimulation. There also is reluctance on the part of producers and veterinarians to use live vaccines for swine dysentery because of the possibility of reversion to virulence, especially as very little is known about genetic regulation and organization in *B. hyodysenteriae*.

The use of recombinant subunit vaccines is an attractive alternative, since the products would be well-defined (essential for registration purposes), and relatively easy to produce on a large scale. To date the first reported use of a recombinant protein from *B. hyodysenteriae* as a vaccine candidate (a 38-kilodalton flagellar protein) failed to prevent colonisation in pigs. This failure is likely to relate specifically to the particular recombinant protein used, as well as to other more down-stream issues of delivery systems and routes, dose rates, choice of adjuvants etc. (Gabe, J D, Chang, R J, Slomiany, R, Andrews, W H and McCaman, M T (1995) Isolation of extracytoplasmic proteins from *Serpulina hyodysenteriae* B204 and molecular cloning of the flaB1 gene encoding a 38-kilodalton flagellar protein.

Infection and Immunity 63:142-148). The first reported partially protective recombinant *B. hyodysenteriae* protein used for vaccination was a 29.7 kDa outer membrane lipoprotein (Bhlp29.7, also referred to as BmpB and BlpA) which had homology with the methionine-binding lipoproteins of various pathogenic bacteria. The use of the his-tagged recombinant Bhlp29.7 protein for vaccination of pigs, followed by experimental challenge with *B. hyodysenteriae*, resulted in 17-40% of vaccinated pigs developing disease compared to 50-70% of the unvaccinated control pigs developing disease. Since the incidence of disease for the Bhlp29.7 vaccinated pigs was significantly (P=0.047) less than for the control pigs, Bhlp29.7 appeared to have potential as a swine dysentery vaccine component (La, T, Phillips, N D, Reichel, M P and Hampson, D J (2004). Protection of pigs from swine dysentery by vaccination with recombinant BmpB, a 29.7 kDa outer-membrane lipoprotein of *Brachyspira hyodysenteriae*. Veterinary Microbiology 102:97-109). A number of other attempts have been made to identify outer envelop proteins from *B. hyodysenteriae* that could be used as recombinant vaccine components, but again no successful vaccine has yet been made. A much more global approach is needed to the identification of potentially useful immunogenic recombinant proteins from *B. hyodysenteriae* is needed.

To date, only one study using DNA for vaccination has been reported. In this study, the *B. hyodysenteriae* ftnA gene, encoding a putative ferritin, was cloned into an *E. coli* plasmid and the plasmid DNA used to coat gold beads for ballistic vaccination. A murine model for swine dysentery was used to determine the protective nature of vaccination with DNA and/or recombinant protein. Vaccination with recombinant protein induced a good systemic response against ferritin however vaccination with DNA induced only a detectable systemic response. Vaccination with DNA followed a boost with recombinant protein induced a systemic immune response to ferritin only after boosting with protein. However, none of the vaccination regimes tested was able to provide the mice with protection against *B. hyodysenteriae* colonisation and the associated lesions. Interestingly, vaccination of the mice with DNA alone resulted in significant exacerbation of disease (Davis, A. J., Smith, S. C. and Moore, R. J. (2005). The *Brachyspira hyodysenteriae* ftnA gene: DNA vaccination and real-time PCR quantification of bacteria in a mouse model of disease. Current Microbiology 50: 285-291).

BRIEF SUMMARY OF INVENTION

It is an object of this invention to have novel genes from *B. hyodysenteriae* and the proteins encoded by those genes. It is a further object of this invention that the novel genes and the proteins encoded by those genes can be used for therapeutic and diagnostic purposes. One can use the genes and/or the proteins in a vaccine against *B. hyodysenteriae* and to diagnose *B. hyodysenteriae* infections.

It is an object of this invention to have novel *B. hyodysenteriae* genes having the nucleotide sequence contained in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, and 65. It is also an object of this invention to have nucleotide sequences that are identical to SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, and 65 where the percentage identity can be at least 95%, 90%, 85%, 80%, 75% and 70% (and every integer from 100 to 70). This invention also includes a DNA vaccine or DNA immunogenic composition containing the nucleotide sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, and 65 and sequences that are at least 95%, 90%, 85%, 80%, 75% and 70% identical (and every integer from 100 to 70) to these sequences. This invention further includes a diagnostic assay containing DNA having the nucleotide sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, and 65 and sequences that are at least 95%, 90%, 85%, 80%, 75% and 70% identical (and every integer from 100 to 70) to these sequences.

It is also an object of this invention to have plasmids containing DNA having the sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, and 65; prokaryotic and/or eukaryotic expression vectors containing DNA having the sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, and 65; and a cell containing the plasmids which contain DNA having the sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, and 65.

It is an object of this invention to have novel *B. hyodysenteriae* proteins having the amino acid sequence contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66. It is another object of this invention to have proteins that are at least 95%, 90%, 85%, 80%, 75% and 70% homologous (and every integer from 100 to 70) to the sequences contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66. It is also an object of this invention for a vaccine or immunogenic composition to contain the proteins having the amino acid sequence contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66, or amino acid sequences that are at least 95%, 90%, 85%, 80%, 75% and 70% homologous (and every integer from 100 to 70) to the sequences contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66. It is a further aspect of this invention to have a diagnostic kit containing one or more proteins having a sequence contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66 or that are at least 95%, 90%, 85%, 80%, 75% and 70% homologous to the sequences contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66.

It is another aspect of this invention to have nucleotide sequences which encode the proteins having the amino acid sequence contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66, and encode the amino acid sequences that are at least 95%, 90%, 85%, 80%, 75% and 70% homologous (and every integer from 100 to 70) to the sequences contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66. The invention also covers plasmids, eukaryotic and prokaryotic expression vectors, and DNA vaccines which contain DNA having a sequence which encodes a protein having the amino acid sequence contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66, and encode amino acid sequences that are at least 95%, 90%, 85%, 80%, 75% and 70% homologous (and every integer from 100 to 70) to the sequences contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66. Cells which contain these plasmids and expression vectors are included in this invention.

This invention includes monoclonal antibodies that bind to proteins having an amino acid sequence contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66 or bind to proteins that are at least 95%, 90%, 85%, 80%, 75% and 70% homologous (and every integer from 100 to 70) to the sequences contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66. Diagnostic kits containing the monoclonal antibodies that bind to proteins having an amino acid sequence contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66 or bind to proteins that are at least 95%, 90%, 85%, 80%, 75% and 70% homologous (and every integer from 100 to 70) to the sequences contained in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66 are included in this invention. These diagnostic kits can detect the presence of *B. hyodysenteriae* in an animal. The animal is preferably any mammal and bird; more preferably, chicken, goose, duck, turkey, parakeet, dog, cat, hamster, gerbil, rabbit, ferret, horse, cow, sheep, pig, monkey, and human.

The invention also contemplates the method of preventing or treating an infection of *B. hyodysenteriae* in an animal by administering to an animal a DNA vaccine containing one or more nucleotide sequences listed in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, and 65 or sequences that are at least 95%, 90%, 85%, 80%, 75% and 70% identical (and every integer from 100 to 70) to these sequences. This invention also covers a method of preventing or treating an infection of *B. hyodysenteriae* in an animal by administering to an animal a vaccine containing one or more proteins having the amino acid sequence containing in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66 or sequences that are at least 95%, 90%, 85%, 80%, 75% and 70% homologous (and every integer from 100 to 70) to these sequences. The animal is preferably any mammal and bird; more preferably, chicken, goose, duck, turkey, parakeet, dog, cat, hamster, gerbil, rabbit, ferret, horse, cow, sheep, pig, monkey, and human.

The invention also contemplates the method of generating an immune response in an animal by administering to an animal an immunogenic composition containing one or more nucleotide sequences listed in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, and 65 or sequences that are at least 95%, 90%, 85%, 80%, 75% and 70% identical (and every integer from 100 to 70) to these sequences. This invention also covers a method of generating an immune response in an animal by administering to an animal an immunogenic composition containing one or more proteins having the amino acid sequence containing in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, and 66 or sequences that are at least 95%, 90%, 85%, 80%, 75% and 70% homologous (and every integer from 100 to 70) to these sequences. The animal is preferably any mammal and bird; more preferably, chicken, goose, duck, turkey, parakeet, dog, cat, hamster, gerbil, rabbit, ferret, horse, cow, sheep, pig, monkey, and human.

DETAILED SUMMARY OF INVENTION

The articles "a" and "an" are used herein to refer to one or to more than one (i.e., to at least one) of the grammatical object of the article. By way of example, "an element" means one element or more than one element.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

An animal can be any mammal or bird. Examples of mammals include dog, cat, hamster, gerbil, rabbit, ferret, horse, cow, sheep, pig, monkey, and human. Examples of birds include chicken, goose, duck, turkey, and parakeet.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz, G. E. and R. H. Schinner., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner include: (i) a positively-charged group containing Lys, Arg and His, (ii) a negatively-charged group containing Glu and Asp, (iii) an aromatic group containing Phe, Tyr and Trp, (iv) a nitrogen ring group containing His and Trp, (v) a large aliphatic nonpolar group containing Val, Leu and De, (vi) a slightly-polar group containing Met and Cys, (vii) a small-residue group containing Ser, Thr, Asp, Asn, Gly, Ala, Glu, Gln and Pro, (viii) an aliphatic group containing Val, Leu, De, Met and Cys, and (ix) a small, hydroxyl group containing Ser and Thr.

A "fusion protein" or "fusion polypeptide" refers to a chimeric protein as that term is known in the art and may be constructed using methods known in the art. In many examples of fusion proteins, there are two different polypeptide sequences, and in certain cases, there may be more. The polynucleotide sequences encoding the fusion protein may be operably linked in frame so that the fusion protein may be translated correctly. A fusion protein may include polypeptide sequences from the same species or from different species. In various embodiments, the fusion polypeptide may contain one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides containing a glutathione S-transferase tag (GST-tag), histidine tag (His-tag), an immunoglobulin domain or an immunoglobulin binding domain.

The term "isolated polypeptide" refers to a polypeptide, in certain embodiments prepared from recombinant DNA or RNA, or of synthetic origin or natural origin, or some combination thereof, which (1) is not associated with proteins that it is normally found with in nature, (2) is separated from the cell in which it normally occurs, (3) is free of other proteins from the same cellular source, (4) is expressed by a cell from a different species, or (5) does not occur in nature. It is possible for an isolated polypeptide exist but not qualify as a purified polypeptide.

The term "isolated nucleic acid" and "isolated polynucleotide" refers to a polynucleotide whether genomic DNA, cDNA, mRNA, tRNA, rRNA, iRNA, or a polynucleotide obtained from a cellular organelle (such as mitochondria and chloroplast), or whether from synthetic origin, which (1) is not associated with the cell in which the "isolated nucleic acid" is found in nature, or (2) is operably linked to a polynucleotide to which it is not linked in nature. It is possible for an isolated polynucleotide exist but not qualify as a purified polynucleotide.

The term "nucleic acid" and "polynucleotide" refers to a polymeric form of nucleotides, either ribonucleotides or deoxyribonucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "nucleic acid of the invention" and "polynucleotide of the invention" refers to a nucleic acid encoding a polypeptide of the invention. A polynucleotide of the invention may comprise all, or a portion of, a subject nucleic acid sequence; a nucleotide sequence at least 60%, 70%, 80%, 90%, 95%, 96%, 97%, 98% or 99% identical to a subject nucleic acid sequence (and every integer between 60 and 100); a nucleotide sequence that hybridizes under stringent conditions to a subject nucleic acid sequence; nucleotide sequences encoding polypeptides that are functionally equivalent to polypeptides of the invention; nucleotide sequences encoding polypeptides at least about 60%, 70%, 80%, 85%, 90%, 95%, 98%, 99% homologous or identical with a subject amino acid sequence (and every integer between 60 and 100); nucleotide sequences encoding polypeptides having an activity of a polypeptide of the invention and having at least about 60%, 70%, 80%, 85%, 90%, 95%, 98%, 99% or more homology or identity with a subject amino acid sequence (and every integer between 60 and 100); nucleotide sequences that differ by 1 to about 2, 3, 5, 7, 10, 15, 20, 30, 50, 75 or more nucleotide substitutions, additions or deletions, such as allelic variants, of a subject nucleic acid sequence; nucleic acids derived from and evolutionarily related to a subject nucleic acid sequence; and complements of, and nucleotide sequences resulting from the degeneracy of the genetic code, for all of the foregoing and other nucleic acids of the invention. Nucleic acids of the invention also include homologs, e.g., orthologs and paralogs, of a subject nucleic acid sequence and also variants of a subject nucleic acid sequence which have been codon optimized for expression in a particular organism (e.g., host cell).

The term "operably linked", when describing the relationship between two nucleic acid regions, refers to a juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

The term "polypeptide", and the terms "protein" and "peptide" which are used interchangeably herein, refers to a polymer of amino acids. Exemplary polypeptides include gene products, naturally-occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In certain embodiments, a fragment may comprise a domain having the desired biological activity, and optionally additional amino acids on one or both sides of the domain, which additional amino acids may number from 5, 10, 15, 20, 30, 40, 50, or up to 100 or more residues. Further, fragments can include a sub-fragment of a specific region, which sub-fragment retains a function of the region from which it is derived. In another embodiment, a fragment may have immunogenic properties.

The term "polypeptide of the invention" refers to a polypeptide containing a subject amino acid sequence, or an equivalent or fragment thereof. Polypeptides of the invention include polypeptides containing all or a portion of a subject amino acid sequence; a subject amino acid sequence with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% homologous to a subject amino acid sequence (and every integer between 60 and 100); and functional fragments thereof. Polypeptides of the invention also include homologs, e.g., orthologs and paralogs, of a subject amino acid sequence.

It is also possible to modify the structure of the polypeptides of the invention for such purposes as enhancing therapeutic or prophylactic efficacy, or stability (e.g., ex vivo shelf life, resistance to proteolytic degradation in vivo, etc.). Such modified polypeptides, when designed to retain at least one activity of the naturally-occurring form of the protein, are considered "functional equivalents" of the polypeptides described in more detail herein. Such modified polypeptides may be produced, for instance, by amino acid substitution, deletion, or addition, which substitutions may consist in whole or part by conservative amino acid substitutions.

For instance, it is reasonable to expect that an isolated conservative amino acid substitution, such as replacement of a leucine with an isoleucine or valine, an aspartate with a glutamate, a threonine with a serine, will not have a major affect on the biological activity of the resulting molecule. Whether a change in the amino acid sequence of a polypeptide results in a functional homolog may be readily determined by assessing the ability of the variant polypeptide to produce a response similar to that of the wild-type protein. Polypeptides in which more than one replacement has taken place may readily be tested in the same manner.

The term "purified" refers to an object species that is the predominant species present (i.e., on a molar basis it is more abundant than any other individual species in the composition). A "purified fraction" is a composition wherein the object species is at least about 50 percent (on a molar basis) of all species present. In making the determination of the purity or a species in solution or dispersion, the solvent or matrix in which the species is dissolved or dispersed is usually not included in such determination; instead, only the species (including the one of interest) dissolved or dispersed are taken into account. Generally, a purified composition will have one species that is more than about 80% of all species present in the composition, more than about 85%, 90%, 95%, 99% or more of all species present. The object species may be purified to essential homogeneity (contaminant species cannot be detected in the composition by conventional detection methods) wherein the composition is essentially a single species. A skilled artisan may purify a polypeptide of the invention using standard techniques for protein purification in light of the teachings herein. Purity of a polypeptide may be determined by a number of methods known to those of skill in the art, including for example, amino-terminal amino acid sequence analysis, gel electrophoresis, mass-spectrometry analysis and the methods described herein.

The terms "recombinant protein" or "recombinant polypeptide" refer to a polypeptide which is produced by recombinant DNA techniques. An example of such techniques includes the case when DNA encoding the expressed protein is inserted into a suitable expression vector which is in turn used to transform a host cell to produce the protein or polypeptide encoded by the DNA.

The term "regulatory sequence" is a generic term used throughout the specification to refer to polynucleotide sequences, such as initiation signals, enhancers, regulators and promoters, that are necessary or desirable to affect the expression of coding and non-coding sequences to which they are operably linked. Exemplary regulatory sequences are described in Goeddel; *Gene Expression Technology: Methods in Enzymology*, Academic Press, San Diego, Calif. (1990), and include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase (e.g., Pho5), the promoters of the yeast α-mating factors, the polyhedron promoter of the baculovirus system and other sequences known to control the expression of genes of prokaryotic or eukaryotic cells or their viruses, and various combinations thereof. The nature and use of such control sequences may differ depending upon the host organism. In prokaryotes, such regulatory sequences generally include promoter, ribosomal binding site, and transcription termination sequences. The term "regulatory sequence" is intended to include, at a minimum, components whose presence may influence expression, and may also include additional components whose presence is advantageous, for example, leader sequences and fusion partner sequences. In certain embodiments, transcription of a polynucleotide sequence is under the control of a promoter sequence (or other regulatory sequence) which controls the expression of the polynucleotide in a cell-type in which expression is intended. It will also be understood that the polynucleotide can be under the control of regulatory sequences which are the same or different from those sequences which control expression of the naturally-occurring form of the polynucleotide.

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids or nucleotides occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The term "soluble" as used herein with reference to a polypeptide of the invention or other protein, means that upon expression in cell culture, at least some portion of the polypeptide or protein expressed remains in the cytoplasmic fraction of the cell and does not fractionate with the cellular debris upon lysis and centrifugation of the lysate. Solubility of a polypeptide may be increased by a variety of art recognized methods, including fusion to a heterologous amino acid sequence, deletion of amino acid residues, amino acid substitution (e.g., enriching the sequence with amino acid residues having hydrophilic side chains), and chemical modification (e.g., addition of hydrophilic groups).

The solubility of polypeptides may be measured using a variety of art recognized techniques, including, dynamic light scattering to determine aggregation state, UV absorption, centrifugation to separate aggregated from non-aggregated material, and SDS gel electrophoresis (e.g., the amount of protein in the soluble fraction is compared to the amount of protein in the soluble and insoluble fractions combined). When expressed in a host cell, the polypeptides of the invention may be at least about 1%, 2%, 5%, 10%, 20%, 30%, 40%, 50%, 60%, 70%, 80%, 90% or more soluble, e.g., at least about 1%, 2%, 5%, 10%, 20%, 30%, 40%, 50%, 60%, 70%, 80%, 90% or more of the total amount of protein expressed in the cell is found in the cytoplasmic fraction. In certain embodiments, a one liter culture of cells expressing a polypeptide of the invention will produce at least about 0.1, 0.2, 0.5, 1, 2, 5, 10, 20, 30, 40, 50 milligrams of more of soluble protein. In an exemplary embodiment, a polypeptide of the invention is at least about 10% soluble and will produce at least about 1 milligram of protein from a one liter cell culture.

The term "specifically hybridizes" refers to detectable and specific nucleic acid binding. Polynucleotides, oligonucleotides and nucleic acids of the invention selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence identity between the polynucleotides, oligonucleotides, and nucleic acids of the invention and a nucleic acid sequence of interest will be at least 30%, 40%, 50%, 60%, 70%, 80%, 85%, 90%, 95%, 98%, 99%, or more (and every integer between 30 and 100). In certain instances, hybridization and washing conditions are performed under stringent conditions according to conventional hybridization procedures and as described further herein.

The terms "stringent conditions" or "stringent hybridization conditions" refer to conditions which promote specific hybridization between two complementary polynucleotide strands so as to form a duplex. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of a polynucleotide sequence hybridizes to a perfectly matched complementary strand. In certain cases it may be desirable to increase the stringency of the hybridization conditions to be about equal to the Tm for a particular duplex.

A variety of techniques for estimating the Tm are available. Typically, G-C base pairs in a duplex are estimated to contribute about 3° C. to the Tm, while A-T base pairs are estimated to contribute about 2° C., up to a theoretical maximum of about 80-100° C.

However, more sophisticated models of Tm are available in which G-C stacking interactions, solvent effects, the desired assay temperature and the like are taken into account. For example, probes can be designed to have a dissociation temperature (Td) of approximately 60° C., using the formula: $Td=(((3\times \#GC)+(2\times \#AT))\times 37)-562)/\#bp)-5$; where #GC, #AT, and #bp are the number of guanine-cytosine base pairs, the number of adenine-thymine base pairs, and the number of total base pairs, respectively, involved in the formation of the duplex.

Hybridization may be carried out in 5×SSC, 4×SSC, 3×SSC, 2×SSC, 1×SSC or 0.2×SSC for at least about 1 hour, 2 hours, 5 hours, 12 hours, or 24 hours. The temperature of the hybridization may be increased to adjust the stringency of the reaction, for example, from about 25° C. (room temperature), to about 45° C., 50° C., 55° C., 60° C., or 65° C. The hybridization reaction may also include another agent affecting the stringency, for example, hybridization conducted in the presence of 50% formamide increases the stringency of hybridization at a defined temperature.

The hybridization reaction may be followed by a single wash step, or two or more wash steps, which may be at the same or a different salinity and temperature. For example, the temperature of the wash may be increased to adjust the stringency from about 25° C. (room temperature), to about 45° C., 50° C., 55° C., 60° C., 65° C., or higher. The wash step may be conducted in the presence of a detergent, e.g., 0.1 or 0.2% SDS. For example, hybridization may be followed by two wash steps at 65° C. each for about 20 minutes in 2×SSC, 0.1% SDS, and optionally two additional wash steps at 65° C. each for about 20 minutes in 0.2×SSC, 0.1% SDS.

Exemplary stringent hybridization conditions include overnight hybridization at 65° C. in a solution containing 50% formamide, 10×Denhardt (0.2% Ficoll, 0.2% polyvinylpyrrolidone, 0.2% bovine serum albumin) and 200 µg/ml of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2×SSC, 0.1% SDS.

Hybridization may consist of hybridizing two nucleic acids in solution, or a nucleic acid in solution to a nucleic acid attached to a solid support, e.g., a filter. When one nucleic acid is on a solid support, a prehybridization step may be conducted prior to hybridization. Prehybridization may be carried out for at least about 1 hour, 3 hours or 10 hours in the same solution and at the same temperature as the hybridization solution (without the complementary polynucleotide strand).

Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y.; S. Agrawal (ed.) Methods in Molecular Biology, volume 20; Tijssen (1993) Laboratory Techniques in Biochemistry and Molecular Biology—Hybridization With Nucleic Acid Probes, e.g., part I chapter 2 "Overview of principles of hybridization and the strategy of nucleic acid probe assays", Elsevier, N.Y.; and Tibanyenda, N. et al., Eur. J. Biochem. 139:19 (1984) and Ebel, S. et al., Biochem. 31:12083 (1992).

The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The nucleic acids of the invention may be used as diagnostic reagents to detect the presence or absence of the target DNA or RNA sequences to which they specifically bind, such as for determining the level of expression of a nucleic acid of the invention. In one aspect, the present invention contemplates a method for detecting the presence of a nucleic acid of the invention or a portion thereof in a sample, the method of the steps of: (a) providing an oligonucleotide at least eight nucleotides in length, the oligonucleotide being complementary to a portion of a nucleic acid of the invention; (b) contacting the oligonucleotide with a sample containing at least one nucleic acid under conditions that permit hybridization of the oligonucleotide with a nucleic acid of the invention or a portion thereof; and (c) detecting hybridization of the oligonucleotide to a nucleic acid in the sample, thereby detecting the presence of a nucleic acid of the invention or a portion thereof in the sample. In another aspect, the present invention contemplates a method for detecting the presence of a nucleic acid of the invention or a portion thereof in a sample, by (a) providing a pair of single stranded oligonucleotides, each of which is at least eight nucleotides in length, complementary to sequences of a nucleic acid of the invention, and wherein the sequences to which the oligonucleotides are complementary are at least ten nucleotides apart; and (b) contacting the oligonucleotides with a sample containing at least one nucleic acid under hybridization conditions; (c) amplifying the nucleotide sequence between the two oligonucleotide primers; and (d) detecting the presence of the amplified sequence, thereby detecting the presence of a nucleic acid of the invention or a portion thereof in the sample.

In another aspect of the invention, the polynucleotide of the invention is provided in an expression vector containing a nucleotide sequence encoding a polypeptide of the invention and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered.

An expression vector containing the polynucleotide of the invention can then be used as a pharmaceutical agent to treat an animal infected with *B. hyodysenteriae* or as a vaccine (also a pharmaceutical agent) to prevent an animal from being infected with *B. hyodysenteriae*, or to reduce the symptoms and course of the disease if the animal does become infected. One manner of using an expression vector as a pharmaceutical agent is to administer a nucleic acid vaccine to the animal at risk of being infected or to the animal after being infected. Nucleic acid vaccine technology is well-described in the art. Some descriptions can be found in U.S. Pat. No. 6,562,376 (Hooper et al.); U.S. Pat. No. 5,589,466 (Felgner, et al.); U.S. Pat. No. 6,673,776 (Felgner, et al.); and U.S. Pat. No. 6,710,035 (Felgner, et al.). Nucleic acid vaccines can be injected into muscle or intradermally, can be electroporated into the animal (see WO 01/23537, King et al.; and WO 01/68889, Malone et al.), via lipid compositions (see U.S. Pat. No. 5,703,055, Felgner, et al), or other mechanisms known in the art field.

Expression vectors can also be transfected into bacteria which can be administered to the target animal to induce an immune response to the protein encoded by the nucleotides of this invention contained on the expression vector. The expression vector can contain eukaryotic expression sequences such that the nucleotides of this invention are transcribed and translated in the host animal. Alternatively, the expression vector can be transcribed in the bacteria and then translated in the host animal. The bacteria used as a carrier of the expression vector should be attenuated but still invasive. One can use *Shigella* spp., *Salmonella* spp., *Escherichia* spp., and *Aeromonas* spp., just to name a few, that have been attenuated but still invasive. Examples of these methods can be found in U.S. Pat. No. 5,824,538 (Branstrom et al); U.S. Pat. No. 5,877,159 (Powell, et al.); U.S. Pat. No. 6,150,170 (Powell, et al.); U.S. Pat. No. 6,500,419 (Hone, et al.); and U.S. Pat. No. 6,682,729 (Powell, et al.).

Alternatively, the polynucleotides of this invention can be placed in certain viruses which act a vector. Viral vectors can either express the proteins of this invention on the surface of the virus, or carry polynucleotides of this invention into an animal cell where the polynucleotide is transcribed and translated into a protein. The animal infected with the viral vectors can develop an immune response to the proteins encoded by the polynucleotides of this invention. Thereby one can alleviate or prevent an infection by *B. hyodysenteriae* in the animal which received the viral vectors. Examples of viral vectors can be found U.S. Pat. No. 5,283,191 (Morgan et al.); U.S. Pat. No. 5,554,525 (Sondermeijer et al) and U.S. Pat. No. 5,712,118 (Murphy).

The polynucleotide of the invention may be used to cause expression and over-expression of a polypeptide of the invention in cells propagated in culture, e.g. to produce proteins or polypeptides, including fusion proteins or polypeptides.

This invention pertains to a host cell transfected with a recombinant gene in order to express a polypeptide of the invention. The host cell may be any prokaryotic or eukaryotic cell. For example, a polypeptide of the invention may be expressed in bacterial cells, such as *E. coli*, insect cells (baculovirus), yeast, plant, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Alternatively, the nucleotide sequence may be altered to optimize expression in the host cell, yet the protein produced would have high homology to the originally encoded protein. Other methods suitable for maximizing expression of the polypeptide will be known to those in the art.

The present invention further pertains to methods of producing the polypeptides of the invention. For example, a host cell transfected with an expression vector encoding a polypeptide of the invention may be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated.

A cell culture includes host cells, media and other byproducts. Suitable media for cell culture are well known in the art. The polypeptide may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of a polypeptide of the invention.

Thus, a nucleotide sequence encoding all or a selected portion of polypeptide of the invention, may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant polypeptides of the invention by microbial means or tissue-culture technology.

Suitable vectors for the expression of a polypeptide of the invention include plasmids of the types: pTrcHis-derived plasmids, pET-derived plasmids, pBR322-derived plasmids, pEMBL-derived plasmids, pEX-derived plasmids, pBTac-derived plasmids and pUC-derived plasmids for expression in prokaryotic cells, such as *E. coli*. The various methods employed in the preparation of the plasmids and transformation of host organisms are well known in the art. For other suitable expression systems for both prokaryotic and eukaryotic cells, as well as general recombinant procedures, see *Molecular Cloning, A Laboratory Manual,* 2nd Ed., ed. by Sambrook, Fritsch and Maniatis (Cold Spring Harbor Laboratory Press, 1989) Chapters 16 and 17.

Coding sequences for a polypeptide of interest may be incorporated as a part of a fusion gene including a nucleotide sequence encoding a different polypeptide. The present invention contemplates an isolated polynucleotide containing a nucleic acid of the invention and at least one heterologous sequence encoding a heterologous peptide linked in frame to the nucleotide sequence of the nucleic acid of the invention so as to encode a fusion protein containing the heterologous polypeptide. The heterologous polypeptide may be fused to (a) the C-terminus of the polypeptide of the invention, (b) the N-terminus of the polypeptide of the invention, or (c) the C-terminus and the N-terminus of the polypeptide of the invention. In certain instances, the heterologous sequence encodes a polypeptide permitting the detection, isolation, solubilization and/or stabilization of the polypeptide to which it is fused. In still other embodiments, the heterologous sequence encodes a polypeptide such as a poly His tag, myc, HA, GST, protein A, protein G, calmodulin-binding peptide, thioredoxin, maltose-binding protein, poly arginine, poly His-Asp, FLAG, a portion of an immunoglobulin protein, and a transcytosis peptide.

Fusion expression systems can be useful when it is desirable to produce an immunogenic fragment of a polypeptide of the invention. For example, the VP6 capsid protein of rotavirus may be used as an immunologic carrier protein for portions of polypeptide, either in the monomeric form or in the form of a viral particle. The nucleic acid sequences corresponding to the portion of a polypeptide of the invention to which antibodies are to be raised may be incorporated into a fusion gene construct which includes coding sequences for a late vaccinia virus structural protein to produce a set of recombinant viruses expressing fusion proteins comprising a portion of the protein as part of the virion. The Hepatitis B surface antigen may also be utilized in this role as well. Similarly, chimeric constructs coding for fusion proteins containing a portion of a polypeptide of the invention and the poliovirus capsid protein may be created to enhance immunogenicity (see, for example, EP Publication NO: 0259149; and Evans et al., (1989) *Nature* 339:385; Huang et al., (1988) *J. Virol.* 62:3855; and Schlienger et al., (1992) *J. Virol.* 66:2).

Fusion proteins may facilitate the expression and/or purification of proteins. For example, a polypeptide of the invention may be generated as a glutathione-S-transferase (GST) fusion protein. Such GST fusion proteins may be used to simplify purification of a polypeptide of the invention, such as through the use of glutathione-derivatized matrices (see, for example, *Current Protocols in Molecular Biology*, eds. Ausubel et al., (N.Y.: John Wiley & Sons, 1991)). In another embodiment, a fusion gene coding for a purification leader sequence, such as a poly-(His)/enterokinase cleavage site sequence at the N-terminus of the desired portion of the recombinant protein, may allow purification of the expressed fusion protein by affinity chromatography using a $Ni^{2+}$ metal resin. The purification leader sequence may then be subsequently removed by treatment with enterokinase to provide the purified protein (e.g., see Hochuli et al., (1987) *J. Chromatography* 411: 177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, *Current Protocols in Molecular Biology*, eds. Ausubel et al., John Wiley & Sons: 1992).

In other embodiments, the invention provides for nucleic acids of the invention immobilized onto a solid surface, including, plates, microtiter plates, slides, beads, particles, spheres, films, strands, precipitates, gels, sheets, tubing, containers, capillaries, pads, slices, etc. The nucleic acids of the invention may be immobilized onto a chip as part of an array. The array may contain one or more polynucleotides of the invention as described herein. In one embodiment, the chip contains one or more polynucleotides of the invention as part of an array of polynucleotide sequences from the same pathogenic species as such polynucleotide(s).

In a preferred form of the invention there is provided isolated *B. hyodysenteriae* polypeptides as herein described, and also the polynucleotide sequences encoding these polypeptides. More desirably the *B. hyodysenteriae* polypeptides are provided in substantially purified form.

Preferred polypeptides of the invention will have one or more biological properties (e.g., in vivo, in vitro or immunological properties) of the native full-length polypeptide. Non-functional polypeptides are also included within the scope of the invention because they may be useful, for example, as antagonists of the functional polypeptides. The biological properties of analogues, fragments, or derivatives relative to wild type may be determined, for example, by means of biological assays.

Polypeptides, including analogues, fragments and derivatives, can be prepared synthetically (e.g., using the well known techniques of solid phase or solution phase peptide synthesis). Preferably, solid phase synthetic techniques are employed. Alternatively, the polypeptides of the invention can be prepared using well known genetic engineering techniques, as described infra. In yet another embodiment, the polypeptides can be purified (e.g., by immunoaffinity purification) from a biological fluid, such as but not limited to plasma, faeces, serum, or urine from animals, including, but not limited to, pig, chicken, goose, duck, turkey, parakeet, human, monkey, dog, cat, horse, hamster, gerbil, rabbit, ferret, horse, cattle, and sheep. An animal can be any mammal or bird.

The *B. hyodysenteriae* polypeptide analogues include those polypeptides having the amino acid sequence, wherein one or more of the amino acids are substituted with another amino acid which substitutions do not substantially alter the biological activity of the molecule.

According to the invention, the polypeptides of the invention produced recombinantly or by chemical synthesis and fragments or other derivatives or analogues thereof, including fusion proteins, may be used as an immunogen to generate antibodies that recognize the polypeptides.

A molecule is "antigenic" when it is capable of specifically interacting with an antigen recognition molecule of the immune system, such as an immunoglobulin (antibody) or T cell antigen receptor. An antigenic amino acid sequence contains at least about 5, and preferably at least about 10, amino acids. An antigenic portion of a molecule can be the portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, $F(ab')_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds an antigen.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction with mercaptoethanol of the disulfide bonds linking the two heavy chain portions, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "adjuvant" refers to a compound or mixture that enhances the immune response to an antigen. An adjuvant can serve as a tissue depot that slowly releases the antigen and also as a lymphoid system activator that non-specifically enhances the immune response [Hood et al., in *Immunology*, p. 384, Second Ed., Benjamin/Cummings, Menlo Park, Calif. (1984)]. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminium hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Various procedures known in the art may be used for the production of polyclonal antibodies to the polypeptides of the invention. For the production of antibody, various host animals can be immunised by injection with the polypeptide of the invention, including but not limited to rabbits, mice, rats, sheep, goats, etc. In one embodiment, a polypeptide of the invention can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward a polypeptide of the invention, any technique that provides for the production of antibody molecules by continuous cell lines in culture may be used. These include but are not limited to the hybridoma technique originally developed by Kohler et al., (1975) *Nature*, 256:495-497, the trioma technique, the human B-cell hybridoma technique [Kozbor et al., (1983) *Immunology Today*, 4:72], and the EBV-hybridoma technique to produce human monoclonal antibodies [Cole et al., (1985) in *Monoclonal Antibodies and Cancer Therapy*, pp. 77-96, Alan R. Liss, Inc.]. Immortal, antibody-producing cell lines can be created by techniques other than fusion, such as direct transformation of B lymphocytes with oncogenic DNA, or transfection with Epstein-Barr virus. See, e.g., U.S. Pat. Nos. 4,341,761; 4,399,121; 4,427,783; 4,444,887; 4,451,570; 4,466,917; 4,472,500; 4,491,632; and 4,493,890.

In an additional embodiment of the invention, monoclonal antibodies can be produced in germ-free animals utilising recent technology. According to the invention, chicken or swine antibodies may be used and can be obtained by using chicken or swine hybridomas or by transforming B cells with EBV virus in vitro. In fact, according to the invention, techniques developed for the production of "chimeric antibodies" [Morrison et al., (1984) *J. Bacteriol.*, 159-870; Neuberger et al., (1984) *Nature*, 312:604-608; Takeda et al., (1985) *Nature*, 314:452-454] by splicing the genes from a mouse antibody molecule specific for a polypeptide of the invention together with genes from an antibody molecule of appropriate biological activity can be used; such antibodies are within the scope of this invention. Such chimeric antibodies are preferred for use in therapy of intestinal diseases or disorders (described infra), since the antibodies are much less likely than xenogenic antibodies to induce an immune response, in particular an allergic response, themselves.

According to the invention, techniques described for the production of single chain antibodies (U.S. Pat. No. 4,946,778) can be adapted to produce single chain antibodies specific for an polypeptide of the invention. An additional embodiment of the invention utilises the techniques described for the construction of Fab expression libraries [Huse et al., (1989) *Science*, 246:1275-1281] to allow rapid and easy identification of monoclonal Fab fragments with the desired specificity for a polypeptide of the invention.

Antibody fragments, which contain the idiotype of the antibody molecule, can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA, "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention. For example, to select antibodies that recognise a specific epitope of a polypeptide of the invention, one may assay generated hybridomas for a product that binds to a fragment of a polypeptide of the invention containing such epitope.

The invention also covers diagnostic and prognostic methods to detect the presence of *B. hyodysenteriae* using a polypeptide of the invention and/or antibodies which bind to the polypeptide of the invention and kits useful for diagnosis and prognosis of *B. hyodysenteriae* infections.

Diagnostic and prognostic methods will generally be conducted using a biological sample obtained from an animal, such as chicken or swine. A "sample" refers to an animal's tissue or fluid suspected of containing a *Brachyspira* species, such as *B. hyodysenteriae*, or its polynucleotides or its polypeptides. Examples of such tissue or fluids include, but not limited to, plasma, serum, fecal material, urine, lung, heart, skeletal muscle, stomach, intestines, and in vitro cell culture constituents.

The invention provides methods for detecting the presence of a polypeptide of the invention in a sample, with the following steps: (a) contacting a sample suspected of containing a polypeptide of the invention with an antibody (preferably bound to a solid support) that specifically binds to the polypeptide of the invention under conditions which allow for the formation of reaction complexes comprising the antibody and the polypeptide of the invention; and (b) detecting the formation of reaction complexes comprising the antibody and polypeptide of the invention in the sample, wherein detection of the formation of reaction complexes indicates the presence of the polypeptide of the invention in the sample.

Preferably, the antibody used in this method is derived from an affinity-purified polyclonal antibody, and more preferably a monoclonal antibody. In addition, it is preferable for the antibody molecules used herein be in the form of Fab, Fab', F(ab')$_2$ or F(v) portions or whole antibody molecules.

Particularly preferred methods for detecting *B. hyodysenteriae* based on the above method include enzyme linked immunosorbent assays, radioimmunoassays, immunoradiometric assays and immunoenzymatic assays, including sandwich assays using monoclonal and/or polyclonal antibodies.

Three such procedures that are especially useful utilise either polypeptide of the invention (or a fragment thereof) labelled with a detectable label, antibody $Ab_1$ labelled with a detectable label, or antibody $Ab_2$ labelled with a detectable label. The procedures may be summarized by the following equations wherein the asterisk indicates that the particle is labelled and "AA" stands for the polypeptide of the invention:

$$AA^* + Ab_1 = AA^*Ab_1 \quad\quad (A.)$$

$$AA + Ab^*_1 = AAAb_1^* \quad\quad (B.)$$

$$AA + Ab_1 + Ab_2^* = Ab_1 AAAb_2^* \quad\quad (C.)$$

The procedures and their application are all familiar to those skilled in the art and accordingly may be utilised within the scope of the present invention. The "competitive" procedure, Procedure A, is described in U.S. Pat. Nos. 3,654,090 and 3,850,752. Procedure B is representative of well-known competitive assay techniques. Procedure C, the "sandwich" procedure, is described in U.S. Pat. Nos. RE 31,006 and 4,016,043. Still other procedures are known, such as the "double antibody" or "DASP" procedure, and can be used.

In each instance, the polypeptide of the invention form complexes with one or more antibody(ies) or binding partners and one member of the complex is labelled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This reaction is because $Ab_1$, raised in one mammalian species, has been used in another species as an antigen to raise the antibody, $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary antibody, and $Ab_2$ will be referred to as a secondary or anti-$Ab_1$ antibody.

The labels most commonly employed for these studies are radioactive elements, enzymes, chemicals that fluoresce when exposed to ultraviolet light, and others. Examples of fluorescent materials capable of being utilised as labels include fluorescein, rhodamine and auramine. A particular detecting material is anti-rabbit antibody prepared in goats and conjugated with fluorescein through an isothiocyanate. Examples of preferred isotope include $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. The radioactive label can be detected by any of the currently available counting procedures. While many enzymes can be used, examples of preferred enzymes are peroxidase, β-glucuronidase, β-D-glucosidase, β-D-galactosidase, urease, glucose oxidase plus peroxidase and alkaline phosphatase. Enzyme are conjugated to the selected particle by reaction with bridging molecules such as carbodiimides, diisocyanates, glutaraldehyde and the like. Enzyme labels can be detected by any of the presently utilized colorimetric, spectrophotometric, fluorospectrophotometric, amperometric or gasometric techniques. U.S. Pat. Nos. 3,654,090; 3,850,752; and 4,016,043 are referred to by way of example for their disclosure of alternate labelling material and methods.

The invention also provides a method of detecting antibodies to a polypeptide of the invention in biological samples, using the following steps: (a) providing a polypeptide of the invention or a fragment thereof; (b) incubating a biological sample with said polypeptide of the invention under conditions which allow for the formation of an antibody-antigen complex; and (c) determining whether an antibody-antigen complex with the polypeptide of the invention is formed.

In another embodiment of the invention there are provided in vitro methods for evaluating the level of antibodies to a polypeptide of the invention in a biological sample using the following steps: (a) detecting the formation of reaction complexes in a biological sample according to the method noted above; and (b) evaluating the amount of reaction complexes formed, which amount of reaction complexes corresponds to the level of polypeptide of the invention in the biological sample.

Further there are provided in vitro methods for monitoring therapeutic treatment of a disease associated with *B. hyodysenteriae* in an animal host by evaluating, as describe above, the levels of antibodies to a polypeptide of the invention in a series of biological samples obtained at different time points from an animal host undergoing such therapeutic treatment.

The present invention further provides methods for detecting the presence or absence of *B. hyodysenteriae* in a biological sample by: (a) bringing the biological sample into contact with a polynucleotide probe or primer of polynucleotide of the invention under suitable hybridizing conditions; and (b) detecting any duplex formed between the probe or primer and nucleic acid in the sample.

According to one embodiment of the invention, detection of *B. hyodysenteriae* may be accomplished by directly amplifying polynucleotide sequences from biological sample, using known techniques and then detecting the presence of polynucleotide of the invention sequences.

In one form of the invention, the target nucleic acid sequence is amplified by PCR and then detected using any of the specific methods mentioned above. Other useful diagnostic techniques for detecting the presence of polynucleotide sequences include, but are not limited to: 1) allele-specific PCR; 2) single stranded conformation analysis; 3) denaturing gradient gel electrophoresis; 4) RNase protection assays; 5) the use of proteins which recognize nucleotide mismatches, such as the *E. coli* mutS protein; 6) allele-specific oligonucleotides; and 7) fluorescent in situ hybridisation.

In addition to the above methods polynucleotide sequences may be detected using conventional probe technology. When probes are used to detect the presence of the desired polynucleotide sequences, the biological sample to be analysed, such as blood or serum, may be treated, if desired, to extract the nucleic acids. The sample polynucleotide sequences may be prepared in various ways to facilitate detection of the target sequence; e.g. denaturation, restriction digestion, electrophoresis or dot blotting. The targeted region of the sample polynucleotide sequence usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Sample polynucleotide sequences and probes are incubated under conditions that promote stable hybrid formation of the target sequence in the probe with the putative desired polynucleotide sequence in the sample. Preferably, high stringency conditions are used in order to prevent false positives.

Detection, if any, of the resulting hybrid is usually accomplished by the use of labelled probes. Alternatively, the probe may be unlabeled, but may be detectable by specific binding with a ligand that is labelled, either directly or indirectly. Suitable labels and methods for labelling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labelled moiety.

It is also contemplated within the scope of this invention that the nucleic acid probe assays of this invention may employ a cocktail of nucleic acid probes capable of detecting the desired polynucleotide sequences of this invention. Thus, in one example to detect the presence of polynucleotide sequences of this invention in a cell sample, more than one probe complementary to a polynucleotide sequences is employed and in particular the number of different probes is alternatively 2, 3, or 5 different nucleic acid probe sequences.

The polynucleotide sequences described herein (preferably in the form of probes) may also be immobilised to a solid phase support for the detection of *Brachyspira* species, including but not limited to *B. hyodysenteriae, B. intermedia, B. alvinipulli, B. aalborgi, B. innocens, B. murdochii,* and *B. pilosicoli*. Alternatively the polynucleotide sequences described herein will form part of a library of DNA molecules that may be used to detect simultaneously a number of different genes from *Brachyspira* species, such as *B. hyodysenteriae*. In a further alternate form of the invention polynucleotide sequences described herein together with other polynucleotide sequences (such as from other bacteria or viruses) may be immobilised on a solid support in such a manner permitting identification of the presence of a *Brachyspira* species, such as *B. hyodysenteriae* and/or any of the other polynucleotide sequences bound onto the solid support.

Techniques for producing immobilised libraries of DNA molecules have been described in the art. Generally, most prior art methods describe the synthesis of single-stranded nucleic acid molecule libraries, using for example masking techniques to build up various permutations of sequences at the various discrete positions on the solid substrate. U.S. Pat. No. 5,837,832 describes an improved method for producing DNA arrays immobilised to silicon substrates based on very large scale integration technology. In particular, U.S. Pat. No. 5,837,832 describes a strategy called "tiling" to synthesize specific sets of probes at spatially defined locations on a substrate that may be used to produced the immobilised DNA libraries of the present invention. U.S. Pat. No. 5,837,832 also provides references for earlier techniques that may also be used. Thus polynucleotide sequence probes may be synthesised in situ on the surface of the substrate.

Alternatively, single-stranded molecules may be synthesised off the solid substrate and each pre-formed sequence applied to a discrete position on the solid substrate. For example, polynucleotide sequences may be printed directly onto the substrate using robotic devices equipped with either pins or pizo electric devices.

The library sequences are typically immobilised onto or in discrete regions of a solid substrate. The substrate may be porous to allow immobilisation within the substrate or substantially non-porous, in which case the library sequences are typically immobilised on the surface of the substrate. The solid substrate may be made of any material to which polypeptides can bind, either directly or indirectly. Examples of suitable solid substrates include flat glass, silicon wafers, mica, ceramics and organic polymers such as plastics, including polystyrene and polymethacrylate. It may also be possible to use semi-permeable membranes such as nitrocellulose or nylon membranes, which are widely available. The semi-permeable membranes may be mounted on a more robust solid surface such as glass. The surfaces may optionally be coated with a layer of metal, such as gold, platinum or other transition metal.

Preferably, the solid substrate is generally a material having a rigid or semi-rigid surface. In preferred embodiments, at least one surface of the substrate will be substantially flat, although in some embodiments it may be desirable to physically separate synthesis regions for different polymers with, for example, raised regions or etched trenches. It is also preferred that the solid substrate is suitable for the high density application of DNA sequences in discrete areas of typically from 50 to 100 µm, giving a density of 10000 to 40000 dots/cm$^{-2}$.

The solid substrate is conveniently divided up into sections. This may be achieved by techniques such as photoetching, or by the application of hydrophobic inks, for example Teflon®-based inks (Cel-line®, USA).

Discrete positions, in which each different member of the library is located may have any convenient shape, e.g., circular, rectangular, elliptical, wedge-shaped, etc.

Attachment of the polynucleotide sequences to the substrate may be by covalent or non-covalent means. The polynucleotide sequences may be attached to the substrate via a layer of molecules to which the library sequences bind. For example, the polynucleotide sequences may be labelled with biotin and the substrate coated with avidin and/or streptavidin. A convenient feature of using biotinylated polynucleotide sequences is that the efficiency of coupling to the solid substrate can be determined easily. Since the polynucleotide sequences may bind only poorly to some solid substrates, it is often necessary to provide a chemical interface between the solid substrate (such as in the case of glass) and the nucleic acid sequences. Examples of suitable chemical interfaces include hexaethylene glycol. Another example is the use of polylysine coated glass, the polylysine then being chemically modified using standard procedures to introduce an affinity ligand. Other methods for attaching molecules to the surfaces of solid substrate by the use of coupling agents are known in the art, see for example WO98/49557.

Binding of complementary polynucleotide sequences to the immobilised nucleic acid library may be determined by a variety of means such as changes in the optical characteristics of the bound polynucleotide sequence (i.e. by the use of ethidium bromide) or by the use of labelled nucleic acids, such as polypeptides labelled with fluorophores. Other detection techniques that do not require the use of labels include optical techniques such as optoacoustics, reflectometry, ellipsometry and surface plasmon resonance (see WO97/49989).

Thus, the present invention provides a solid substrate having immobilized thereon at least one polynucleotide of the present invention, preferably two or more different polynucleotide sequences of the present invention.

The present invention also can be used as a prophylactic or therapeutic, which may be utilised for the purpose of stimulating humoral and cell mediated responses in animals, such as chickens and swine, thereby providing protection against colonisation with *Brachyspira* species, including but not limited to *B. hyodysenteriae, B. suanatina, B. intermedia, B. alvinipulli, B. aalborgi, B. innocens, B. murdochii,* and *B. pilosicoli*. Natural infection with a *Brachyspira* species, such as *B. hyodysenteriae* induces circulating antibody titres against the proteins described herein. Therefore, the amino acid sequences described herein or parts thereof, have the potential to form the basis of a systemically or orally administered prophylactic or therapeutic to provide protection against intestinal spirochaetosis.

Accordingly, in one embodiment the present invention provides the amino acid sequences described herein or fragments thereof or antibodies that bind the amino acid sequences or the polynucleotide sequences described herein in a therapeutically effective amount admixed with a pharmaceutically acceptable carrier, diluent, or excipient.

The phrase "therapeutically effective amount" is used herein to mean an amount sufficient to reduce by at least about 15%, preferably by at least 50%, more preferably by at least 90%, and most preferably prevent, a clinically significant deficit in the activity, function and response of the animal host. Alternatively, a therapeutically effective amount is sufficient to cause an improvement in a clinically significant condition in the animal host.

The phrase "pharmaceutically acceptable" refers to molecular entities and compositions that are physiologically tolerable and do not typically produce an allergic or similarly untoward reaction, such as gastric upset and the like, when administered to an animal. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, *Remington's Pharmaceutical Sciences*, 18th Ed., Mack Publishing Co., Easton, Pa., (1990).

In a more specific form of the invention there are provided pharmaceutical compositions comprising therapeutically effective amounts of the amino acid sequences described herein or an analogue, fragment or derivative product thereof or antibodies thereto together with pharmaceutically acceptable diluents, preservatives, solubilizes, emulsifiers, adjuvants and/or carriers. Such compositions include diluents of various buffer content (e.g., Tris-HCl, acetate, phosphate), pH and ionic strength and additives such as detergents and solubilizing agents (e.g., Tween® 80, Polysorbate 80), antioxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as polylactic acid, polyglycoli.c acid, etc. or into liposomes, Hylauronic acid may also be used. Such compositions may influence the physical state, stability, rate of in vivo release, and rate of in vivo clearance of the present proteins and derivatives. See, e.g., Martin, *Remington's Pharmaceutical Sciences*, 18th Ed. (1990, Mack Publishing Co., Easton, Pa. 18042) pages 1435-1712 that are herein incorporated by reference. The compositions may be prepared in liquid form, or may be in dried powder, such as lyophilised form.

Alternatively, the polynucleotides of the invention can be optimized for expression in plants (e.g., corn). The plant may be transformed with plasmids containing the optimized polynucleotides. Then the plant is grown, and the proteins of the invention are expressed in the plant, or the plant-optimized version is expressed. The plant is later harvested, and the section of the plant containing the proteins of the invention is processed into feed for the animal. This animal feed will impart immunity against *B. hyodysenteriae* when eaten by the animal. Examples of prior art detailing these methods can be found in U.S. Pat. No. 5,914,123 (Arntzen, et al.); U.S. Pat. No. 6,034,298 (Lam, et al.); and U.S. Pat. No. 6,136,320 (Arntzen, et al.).

It will be appreciated that pharmaceutical compositions provided accordingly to the invention may be administered by any means known in the art. Preferably, the pharmaceutical compositions for administration are administered by injection, orally, or by the pulmonary, or nasal route. The amino acid sequences described herein or antibodies derived therefrom are more preferably delivered by intravenous, intraarterial, intraperitoneal, intramuscular, or subcutaneous routes of administration. Alternatively, the amino acid sequence described herein or antibodies derived therefrom, properly formulated, can be administered by nasal or oral administration.

Also encompassed by the present invention is the use of polynucleotide sequences of the invention, as well as antisense and ribozyme polynucleotide sequences hybridisable to a polynucleotide sequence encoding an amino acid sequence according to the invention, for manufacture of a medicament for modulation of a disease associated *B. hyodysenteriae*.

Polynucleotide sequences encoding antisense constructs or ribozymes for use in therapeutic methods are desirably administered directly as a naked nucleic acid construct. Uptake of naked nucleic acid constructs by bacterial cells is enhanced by several known transfection techniques, for example those including the use of transfection agents. Example of these agents include cationic agents (for example calcium phosphate and DEAE-dextran) and lipofectants. Typically, nucleic acid constructs are mixed with the transfection agent to produce a composition.

Alternatively the antisense construct or ribozymes may be combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration. The routes of administration described are intended only as a guide since a skilled practitioner will be able to determine readily the optimum route of administration and any dosage for any particular animal and condition.

The invention also includes kits for screening animals suspected of being infected with a *Brachyspira* species, such as *B. hyodysenteriae* or to confirm that an animal is infected with a *Brachyspira* species, such as *B. hyodysenteriae*. In a further embodiment of this invention, kits suitable for use by a specialist may be prepared to determine the presence or absence of *Brachyspira* species, including but not limited to *B. hyodysenteriae, B. suanatina, B. intermedia, B. alvinipulli, B. aalborgi, B. innocens, B. murdochii*, and *B. pilosicoli* in suspected infected animals or to quantitatively measure a *Brachyspira* species, including but not limited to *B. hyodysenteriae, B. suanatina, B. intermedia, B. alvinipulli, B. aalborgi* and *B. pilosicoli* infection. In accordance with the testing techniques discussed above, such kits can contain at least a labelled version of one of the amino acid sequences described herein or its binding partner, for instance an antibody specific thereto, and directions depending upon the method selected, e.g., "competitive," "sandwich," "DASP" and the like. Alternatively, such kits can contain at least a polynucleotide sequence complementary to a portion of one of the polynucleotide sequences described herein together with instructions for its use. The kits may also contain peripheral reagents such as buffers, stabilizers, etc.

Accordingly, a test kit for the demonstration of the presence of a *Brachyspira* species, including but not limited to *B. hyodysenteriae, B. suanatina, B. intermedia, B. alvinipulli, B. aalborgi, B. innocens, B. murdochii*, and *B. pilosicoli*, may contain the following:

(a) a predetermined amount of at least one labelled immunochemically reactive component obtained by the direct or indirect attachment of one of the amino acid sequences described herein or a specific binding partner thereto, to a detectable label;

(b) other reagents; and (c) directions for use of said kit.

More specifically, the diagnostic test kit may contain:

(a) a known amount of one of the amino acid sequences described herein as described above (or a binding partner) generally bound to a solid phase to form an immunosorbent, or in the alternative, bound to a suitable tag, or there are a plural of such end products, etc;

(b) if necessary, other reagents; and (c) directions for use of said test kit.

In a further variation, the test kit may contain:

(a) a labelled component which has been obtained by coupling one of the amino acid sequences described herein to a detectable label;

(b) one or more additional immunochemical reagents of which at least one reagent is a ligand or an immobilized ligand, which ligand is selected from the group consisting of:

(i) a ligand capable of binding with the labelled component (a);

(ii) a ligand capable of binding with a binding partner of the labelled component (a);

(iii) a ligand capable of binding with at least one of the component(s) to be determined; or (iv) a ligand capable of binding with at least one of the binding partners of at least one of the component(s) to be determined; and (c) directions for the performance of a protocol for the detection and/or determination of one or more components of an immunochemical reaction between one of the amino acid sequences described herein and a specific binding partner thereto.

Preparation of Genomic Library

A genomic library is prepared using an Australian porcine field isolate of *B. hyodysenteriae* (strain WA1), This strain has been well-characterised and shown to he virulent following experimental challenge of pigs. The cetyltrimetyhylammonium bromide (CTAB) method is used to prepare high quality chromosomal DNA suitable for preparation of genomic DNA libraries. *B. hyodysenteriae* is grown in 100 ml anaerobic trypticase soy broth culture to a cell density of $10^9$ cells/ml. The cells are harvested at 4,000×g for 10 minutes, and the cell pellet resuspended in 9.5 ml TE buffer. SDS is added to a final concentration of 0.5% (w/v), and the cells lysed at 37° C. for 1 hour with 100 μg of Proteinase K. NaCl is added to a final concentration of 0.7 M and 1.5 ml CTAB/NaCl solution (10% w/v CTAB, 0.7 M NaCl) is added before incubating the solution at 65° C. for 20 minutes. The lysate is extracted with an equal volume of chloroform/isoamyl alcohol, and the tube is centrifuged at 6,000×g for 10 minutes to separate the phases. The aqueous phase is transferred to a fresh tube and 0.6 volumes of isopropanol are added to precipitate the high molecular weight DNA. The precipitated DNA is collected using a hooked glass rod and transferred to a tube containing 1 ml of 70% (v/v) ethanol. The tube is centrifuged at 10,000×g and the pelleted DNA redissolved in 4 ml TE buffer overnight. A cesium chloride gradient containing 1.05 g/ml CsCl and 0.5 mg/ml ethidium bromide is prepared using the redissolved DNA solution. The gradient is transferred to 4 ml scalable centrifuge tubes and centrifuged at 70,000×g overnight at 15° C. The separated DNA is visualized under an ultraviolet light, and the high molecular weight DNA is withdrawn from the gradient using a 15-g needle. The ethidium bromide is removed from the DNA by sequential extraction with CsCl-saturated isopropanol. The purified chromosomal DNA is dialysed against 2 liters TE buffer and precipitated with isopropanol. The resuspended genomic DNA is sheared using a GeneMachines Hydroshear™ (Genomic Solutions, Ann Arbor, Mich.), and the sheared DNA is filled-in using Klenow DNA polymerase to generate blunt-end. fragments. One hundred ng of the blunt-end DNA fragments is ligated with 25 ng of pSMART® VC vector (Lucigen, Meddleton, Wis.) using CloneSmart® DNA ligase, The ligated DNA is then eleetroporated into *E coli* electrocompetent cells. A small insert (2-3 kb) library and medium insert (3-40 kb) library is constructed into the low copy version of the pSMART® VC vector.

Genomic Sequencing

After the genomic library is obtained, individual clones of *E. coil* containing the pSMART® VC vector are picked. The plasmid DNA is purified and sequenced. The purified plasmids are subjected to automated direct sequencing of the pSMART® VC vector using the forward and reverse primers specific for the pSMART® VC vector. Each sequencing reaction is performed in a 10 μl volume consisting of 200 ng of plasmid DNA, 2 pmol of primer, and 4 μl of the ABI PRISM™ BigDye® Terminator Cycle Sequencing Ready Reaction Mix (PE Applied Biosystems, Foster City, Calif.). Cycling conditions involve a 2 minute denaturing step at 96° C., followed by 25 cycles of denaturation at 96° C. for 10 seconds, and a combined primer annealing and extension step at 60° C. for 4 minutes. Residual dye terminators are removed from the sequencing products by precipitation with 95% (v/v) ethanol containing 85 mM sodium acetate (pH 5.2), 3 mM EDTA (pH 8), and vacuum dried. The plasmids are sequenced in duplicate using each primer. Sequencing products are analysed using an ABI 373A DNA Sequencer (PE Applied Biosystems).

Annotation

Partial genome sequences for *B. hyodysenteriae* are assembled and annotated using a range of public domain bioinformatics tools to analyse and re-analyse the sequences as part of a quality assurance procedure on data analysis. Open reading frames (ORFs) are predicted using a variety of programs including GeneMark™, GLIMMER, ORPHEUS, SELFID and GetORF, Putative ORFS are examined for homology (DNA and protein) with existing international databases using searches including BLAST and FASTA. All the predicted ORFs are analysed to determine their cellular localisation using programs including PSI-BLAST, FASTA, MOTIFS, FINDPATTERNS, PHD, SIGNALP and PSORT. Databases including Interpro, Prosite, ProDom, Pfam and Blocks are used to predict surface associated proteins such as transmembrane domains, leader peptides, homologies to known surface proteins, lipoprotein signature, outer membrane anchoring motifs and host cell binding domains. Phylogenetic and other molecular evolution analysis is conducted with the identified genes and with other species to assist in the assignment of function. The in silico analysis of both partially sequenced genomes produces a comprehensive list of all the predicted ORFS present in the sequence data available. Each ORF is interrogated for descriptive information such as predicted molecular weight, isoelectric point, hydrophobicity, and subcellular localisation to enable correlation with the in vitro properties of the native gene product. Predicted genes which encode proteins similar to surface localized components and/or virulence factors in other pathogenic bacteria are selected as potential vaccine targets.

Bioinformatics Results

The shotgun sequencing of the *B. hyodysenteriae* genome results in 94.6% (3028.6 kb out of a predicted 3200 kb) of the genome being sequenced. The *B. hyodysenteriae* sequence is comprised of 294 contigs with an average contig size of 10.3 kb. For *B. hyodysenteriae,* 2,593 open-reading frames (ORFs) are predicted from the 294 contigs. Comparison of the predicted ORFs with genes present in the nucleic acid and protein databases indicate that approximately 70% of the ORFs have homology with genes contained in the public databases. The remaining 30% of the predicted ORFs have no known identity.

Vaccine Candidates

To help reduce the number of ORFs that would be tested as a vaccine candidate, ORF's showing reasonable homology (E-value less than $e^{-15}$) with outer surface proteins, secreted proteins, and possible virulence factors present in public databases are selected as potential vaccine candidates. Of the 2,593 ORFs obtained in the genomic shotgun sequencing, many passed this test but the results of thirty-three genes are presented here. Table 1 shows thirty-three genes selected as potential vaccine targets and their similarity with other known amino acid sequences obtained from SWISS-PROT database. It is noted that the percent identity of amino acids does not raise above 58% while the percent similarity or homology of amino acids remains less than 71%, thus indicating that these ORFs are unique.

TABLE 1

| Gene | Identity of Protein With Highest Homology | Identity (amino acids) | Similarity (amino acids) | Accession Number |
|---|---|---|---|---|
| NAV-H54 | Variable surface protein (VspD) of *Brachyspira hyodysenteriae* | 106/223 (47%) | 136/223 (60%) | O68157 |
| NAV-H55 | Flagellar protein B of *Leptospira interrogans* | 58/213 (27%) | 108/213 (50%) | Q72SJ3 |
| NAV-H56 | Myosin-like major antigen | 288/1509 (19%) | 609/1509 (40%) | P21249 |
| NAV-H57 | Lytic murein transglycosylate (possibly outer membrane-bound) | 97/318 (25%) | 158/318 (41%) | Q6F7W9 |
| NAV-H58 | Outer membrane protein of *Treponema pallidum* | 57/175 (32%) | 90/175 (51%) | P96127 |
| NAV-H59 | Myosin-like major antigen | 204/1012 (20%) | 432/1012 (42%) | P21249 |
| NAV-H60 | Outer membrane protein and related peptidoglycan-associated lipoprotein | 46/139 (33%) | 68/139 (48%) | COG2885 |
| NAV-H61 | Putative lipoprotein of *Treponema denticola* | 336/805 (41%) | 483/805 (60%) | Q73NT0 |
| NAV-H62 | NlpA lipoprotein of *Streptococcus suis* | 92/269 (34%) | 151/269 (56%) | Q303L3 |
| NAV-H63 | NlpA lipoprotein of *Streptococcus suis* | 106/312 (33%) | 167/312 (53%) | Q303L3 |
| NAV-H64 | NlpA lipoprotein of *Streptococcus suis* | 112/337 (33%) | 198/337 (58%) | Q303L3 |
| NAV-H65 | Putative secreted protein of *Streptomyces violaceoruber* | 50/127 (39%) | 68/127 (53%) | Q849M9 |
| NAV-H66 | Toxin (YoeB) of *Escherichia coli* | 42/85 (58%) | 60/85 (76%) | P69349 |
| NAV-H67 | Outer membrane protein (TolC) | 80/350 (20%) | 171/350 (39%) | Q2Z054 |
| NAV-H68 | Probable hemolysin-related protein of *Dehalococcoides* sp. | 121/415 (29%) | 204/415 (49%) | Q3ZYX1 |
| NAV-H69 | Outer surface protein of *Bacillus cereus* | 193/357 (54%) | 256/357 (71%) | Q4MWS0 |
| NAV-H70 | Membrane associated lipoprotein of *Vibrio vulnificus* | 146/417 (35%) | 203/417 (48%) | Q2SRL9 |
| NAV-H71 | Surface layer protein of *Methanosarcina barkeri* | 72/201 (36%) | 112/201 (49%) | Q8TJE3 |
| NAV-H72 | Lytic murein transglycosylate (possibly outer membrane-bound) | 51/141 (36%) | 6/141 (53%) | P44049 |
| NAV-H73 | Toxin (YoeB) of *Escherichia coli* | 42/84 (50%) | 62/84 (73%) | P69349 |
| NAV-H74 | Outer membrane protein/ protective antigen | 210/833 (25%) | 339/833 (40%) | COG4775 |

TABLE 1-continued

| Gene | Identity of Protein With Highest Homology | Identity (amino acids) | Similarity (amino acids) | Accession Number |
|---|---|---|---|---|
| NAV-H22 | variable surface protein (VspH) of *Brachyspira hyodysenteriae* | 29% (133/454) | 43% (199/454) | AAK14803.1 |
| NAV-H23 | membrane associated lipoprotein of *Mycoplasma mycoides* | 43% (114/263) | 60% (159/263) | AAF27178.1 |
| NAV-H24 | Outer membrane lipoprotein of *Geobacter metallireducens* | 32% (46/142) | 53% (76/142) | ZP00300921.1 |
| NAV-H30 | surface antigen (BspA) of *Bacteroides forsythus* | 38% (83/216) | 55% (120/216) | AAC82625.1 |
| NAV-H32 | hemolytic protein (HlpA) of *Nostoc* sp. | 35% (49/137) | 56% (77/137) | NP488469.1 |
| NAV-H33 | hemolytic protein of *Prevotella intermedia* | 54% (64/117) | 70% (83/117) | AAC05836.1 |
| NAV-H37 | virulence-mediating protein (VirC) of *Vibrio parahaemolyticus* | 36% (58/159) | 63% (101/159) | NP800579.1 |
| NAV-H40 | lytic murein transglycosylase (contains LysM/invasin domains) | 26% (120/449) | 41% (185/449) | ZP00146104.1 |
| NAV-H41 | surface antigen BspA of *Bacteroides forsythus* | 41% (84/201) | 57% (115/201) | AAC82625.1 |
| NAV-H43 | Hemolysins and related proteins of *Anabaena variabilis* | 35% (150/425) | 56% (242/425) | ZP00162711.2 |
| NAV-H44 | outer membrane porin of *Leptospira interrogans* | 20% (79/393) | 41% (163/393) | YP001419.1 |
| NAV-H45 | virulence factor (MviN) protein of *Geobacter sulfurreducens* | 32% (153/469) | 49% (231/469) | NP952225.1 |

The DNA and amino acid sequences of NAV-H54 are found in SEQ ID NOs: 1 and 2, respectively. The DNA and amino acid sequences of NAV-H55 are found in SEQ ID NOs: 3 and 4, respectively. The DNA and amino acid sequences of NAV-H56 are found in SEQ ID NOs: 5 and 6, respectively. The DNA and amino acid sequences of NAV-H57 are found in SEQ ID NOs: 7 and 8, respectively. The DNA and amino acid sequences of NAV-H58 are found in SEQ ID NOs: 9 and 10, respectively. The DNA and amino acid sequences of NAV-H59 are found in SEQ ID NOs: 11 and 12, respectively. The DNA and amino acid sequences of NAV-H60 are found in SEQ ID NOs: 13 and 14, respectively. The DNA and amino acid sequences of NAV-H61 are found in SEQ ID NOs: 15 and 16, respectively. The DNA and amino acid sequences of NAV-H62 are found in SEQ ID NOs: 17 and 18, respectively. The DNA and amino acid sequences of NAV-H63 are found in SEQ ID NOs: 19 and 20, respectively. The DNA and amino acid sequences of NAV-H64 are found in SEQ ID NOs: 21 and 22, respectively. The DNA and amino acid sequences of NAV-H65 are found in SEQ ID NOs: 23 and 24, respectively. The DNA and amino acid sequences of NAV-H66 are found in SEQ ID NOs: 25 and 26, respectively. The DNA and amino acid sequences of NAV-H67 are found in SEQ ID NOs: 27 and 28, respectively. The DNA and amino acid sequences of NAV-H68 are found in SEQ ID NOs: 29 and 30, respectively. The DNA and amino acid sequences of NAV-H69 are found in SEQ ID NOs: 31 and 32, respectively. The DNA and amino acid sequences of NAV-H70 are found in SEQ ID NOs: 33 and 34, respectively. The DNA and amino acid sequences of NAV-H71 are found in SEQ ID NOs: 35 and 36, respectively. The DNA and amino acid sequences of NAV-H72 are found in SEQ ID NOs: 37 and 38, respectively. The DNA and amino acid sequences of NAV-H73 are found in SEQ ID NOs: 39 and 40, respectively. The DNA and amino acid sequences of NAV-H74 are found in SEQ ID NOs: 41 and 42, respectively.

The DNA and amino acid sequences of NAV-H22 are found in SEQ ID NOs: 43 and 44, respectively. The DNA and amino acid sequences of NAV-H23 are found in SEQ ID NOs: 45 and 46, respectively. The DNA and amino acid sequences of NAV-H24 are found in SEQ ID NOs: 47 and 48, respectively. The DNA and amino acid sequences of NAV-H30 are found in SEQ ID NOs: 49 and 50, respectively. The DNA and amino acid sequences of NAV-H32 are found in SEQ ID NOs: 51 and 52, respectively. The DNA and amino acid sequences of NAV-H33 are found in SEQ ID NOs: 53 and 54, respectively. The DNA and amino acid sequences of NAV-H37 are found in SEQ ID NOs: 55 and 56, respectively. The DNA and amino acid sequences of NAV-H40 are found in SEQ ID NOs: 57 and 58, respectively. The DNA and amino acid sequences of NAV-H41 are found in SEQ ID NOs: 59 and 60, respectively. The DNA and amino acid sequences of NAV-H43 are found in SEQ ID NOs: 61 and 62, respectively. The DNA and amino acid sequences of NAV-H44 are found in SEQ ID NOs: 63 and 64, respectively. The DNA and amino acid sequences of NAV-H45 are found in SEQ ID NOs: 65 and 66, respectively.

To further reduce the number of ORFs that would be tested as a vaccine candidate, gene products predicted by the in silico analysis to be localised in the cytoplasm or inner membrane of the spirochaete are abandoned. As a result, twenty one of the thirty three genes presented in Table 1 are further analysed. These include NAV-H58, NAV-H60, NAV-H62, NAV-H64, NAV-H66, NAV-H67, NAV-H69, NAV-H71, NAV-H73, NAV-H22, NAV-H23, NAV-H24, NAV-H30, NAV-H32, NAV-H33, NAV-H37, NAV-H40, NAV-H41, NAV-H43, NAV-H44, and NAV-H45.

Analysis of Gene Distribution Using Polymerase Chain Reaction (PCR)

One or two primer pairs which anneal to different regions of the target gene encoding region are designed and optimised for PCR detection. Individual primers are designed using Oligo Explorer 1.2 and primer sets with calculated melting temperatures of approximately 55-60° C. are selected. These primers sets are also selected to generate PCR products greater than 200 bp. A medium-stringency primer annealing temperature of 50° C. is selected for the distribution analysis PCR. The medium-stringency conditions would allow potential minor mismatched sequences (because of strain differences) occurring at the primer binding sites to not affect primer binding. Distribution analysis of the twenty one *B. hyodysenteriae* target genes are performed on 23 strains of *B. hyodysenteriae*, including two strains which have been shown to be avirulent. PCR analysis is performed in a 25 μl total volume using Taq DNA polymerase (Biotech International, Thurmont, Md.). The amplification mixture consists of 1×PCR buffer (containing 1.5 mM of $MgCl_2$), 1 U of Taq DNA polymerase, 0.2 mM of each dNTP (Amersham Pharmacia Biotech, Piscataway, N.J.), 0.5 μM of the primer pair, and 1 μl purified chromosomal template DNA. Cycling conditions involve an initial template denaturation step of 5 minutes at 94° C., follow by 35 cycles of denaturation at 94° C. for 30 seconds, annealing at 50° C. for 15 seconds, and primer extension at 68° C. for 4 minutes. The PCR products are subjected to electrophoresis in 1% (w/v) agarose gels in 1×TAE buffer (40 mM Tris-acetate, 1 mM EDTA), staining with a 1 μg/ml ethidium bromide solution and viewing over UV light.

The primers used for eighteen genes (out of twenty one) are indicated in Table 2. Of these eighteen genes, three of them (NAV-H23, NAV-H41 and NAV-H71) are present in 83% of the *B. hyodysenteriae* strains tested; three of them (NAV-H24, NAV-H30 and NAV-H73) are present in 87% of the strains tested, seven of them (NAV-H22, NAV-H32, NAV-H33, NAV-H37, NAV-H43, NAV-H64 and NAV-H69) are present in 91% of the strains tested, and three of them (NAV-H40, NAV-H44, and NAV-H45) are present in 100% of the strains tested. The remaining three genes are present in less than 80% of the *B. hyodysenteriae* strains tested. The poor distribution of these genes makes them less useful as a vaccine subunit. For this reason, further analysis of these genes has been abandoned.

TABLE 2

| Gene | Primer name | Primer Sequence (5'-3') | |
|---|---|---|---|
| NAV-H22 | H22-F4 | AAACGTTTATATTTTATTTTATC | (SEQ ID NO: 67) |
| | H22-R1308 | AAACTTCCAAGTGATACC | (SEQ ID NO: 68) |
| NAV-H23 | H23-F4 | AAATATAAACCTACAAGCAG | (SEQ ID NO: 69) |
| | H23-R2366 | AATATTTCAGTTAATCTAAAATC | (SEQ ID NO: 70) |
| NAV-H24 | H24-F19 | ACTTTAATCTTTGTATTAATTTTG | (SEQ ID NO: 71) |
| | H24-R729 | TTGTTTTAATTTGATAATATCAG | (SEQ ID NO: 72) |
| NAV-H30 | H30-F4 | AAAAAAATTATTTTATTAATATTTATATT | (SEQ ID NO: 73) |
| | H30-R969 | TTCTCTTATAATCTTTACAGTTG | (SEQ ID NO: 74) |
| NAV-H32 | H32-F4 | CATATTTCTGGTGATTCTC | (SEQ ID NO: 75) |
| | H32-R564 | TTTTTTGATAAATAAGTTTTTTATTTG | (SEQ ID NO: 76) |
| NAV-H33 | H33-F4 | TTTAATACTCCTATATTATTAATTATTT | (SEQ ID NO: 77) |
| | H33-R396 | AAGGAGAATCACCAGAAA | (SEQ ID NO: 78) |
| NAV-H37 | H37-F4 | AATGATATTATTAAAGTGATAAA | (SEQ ID NO: 79) |
| | H37-R825 | AAAATCTAATATAACGGATT | (SEQ ID NO: 80) |
| NAV-H40 | H40-F16 | AAATATGCTTCCATTATAGG | (SEQ ID NO: 81) |
| | H40-R1815 | ACTTTTAGGAAGAAGTTTAAC | (SEQ ID NO: 82) |
| NAV-H41 | H41-F19 | TATATTTTCATTATATATTTATTAG | (SEQ ID NO: 83) |
| | H41-R1067 | CTAGGCATAGATTTTCCA | (SEQ ID NO: 84) |
| NAV-H43 | H43-F46 | TTTGCCATGTCGGAAATTGCAG | (SEQ ID NO: 85) |
| | H43-R1236 | TATTCTAGCACCGTCCATATC | (SEQ ID NO: 86) |
| NAV-H44 | H44-F43 | GTATGTTTATATGCTCAGGATAC | (SEQ ID NO: 87) |
| | H44-R2931 | AACAGCAGCACTATCTTGTAA | (SEQ ID NO: 88) |
| | H44-F80 | CAGCAGCAACAAATAATACTACTG | (SEQ ID NO: 89) |
| | H44-R929 | TGAATATAAACACCTTCTCTCAAAG | (SEQ ID NO: 90) |
| NAV-H45 | H45-F52 | AAAATGTCATTGGTAACTACTGTAAG | (SEQ ID NO: 91) |
| | H45-R1595 | CTTGATAATCTGCCTTTAAACATAC | (SEQ ID NO: 92) |
| NAV-H62 | H62-F69 | ATGTGAGGAAAAAACAGAAAG | (SEQ ID NO: 93) |
| | H62-R866 | TCATTACCAGAAAACCATACTC | (SEQ ID NO: 94) |
| NAV-H64 | H64-F69 | AGGAAATAAAGCTCCTGCTGCTTCAGC | (SEQ ID NO: 95) |
| | H64-R253 | GCATAGCAGCAACTTCAGAAGGTCCA | (SEQ ID NO: 96) |
| NAV-H66 | H66-F114 | CTTATTAATTGGTATAGGAAAACC | (SEQ ID NO: 97) |
| | H66-R200 | AATCTATGTTCTTGATTTATTAGCC | (SEQ ID NO: 98) |
| NAV-H69 | H69-F546 | AGAAGCTACTTTTGGACCTTGGCCTGT | (SEQ ID NO: 99) |
| | H69-R662 | ACACAGTCAACACCAAGAGC | (SEQ ID NO: 100) |
| NAV-H71 | H71-F568 | AAACAGCAGACTAGCTGGTG | (SEQ ID NO: 101) |
| | H71-R773 | TGACCATTACTTACACCGGATACCCA | (SEQ ID NO: 102) |
| | H71-F37 | TTAATGACTATATCGCTTTCATACACTTTC | (SEQ ID NO: 103) |
| | H71-R1241 | TCAATTCTTCCAGACATAAAATCAGTAAG | (SEQ ID NO: 104) |
| NAV-H73 | H73-F37 | TATATAGAGTGGGTATCAGAAG | (SEQ ID NO: 105) |
| | H73-R254 | TCATAATGGTATTTACAAGATG | (SEQ ID NO: 106) | pTrcHis Plasmid Extraction

*Escherichia coli* JM 109 clones harboring the pTrcHis plasmid (Invitrogem Carlsbad, Calif.) are streaked out from glycerol stock storage onto Luria-Bertani (LB) agar plates supplemented with 100 mg/l ampicillin and incubated at 37° C. for 16 hours. A single colony is used to inoculate 10 ml of LB broth supplemented with 100 mg/l ampicillin, and the broth culture is incubated at 37° C. for 12 hours with shaking. The entire overnight culture is centrifuged at 5,000×g for 10 minutes, and the plasmid contained in the cells is extracted using the QIAprep® Spin Miniprep Kit (Qiagen, Doncaster VIC), The pelleted cells are resuspended with 250 μl cell resuspension buffer P1 and then are lysed with the addition of 250 μl cell lysis buffer P2. The lysed cells are neutralized with 350 μl neutralization buffer N3, and the precipitated cell debris is pelleted by centrifugation at 20,000×g for 10 minutes. The supernatant is transferred to a spin column and centrifuged at 10,000×g for 1 minute. After discarding the flow-through, 500 μl wash buffer PE is applied to the column and centrifuged as before. The flow-through is discarded, and the column is dried by centrifugation at 20,000×g for 3 minutes. The plasmid DNA is eluted from the column with 100 μl elution buffer EB. The purified plasmid is quantified using a Dynaquan™ DNA fluorometer (Hoefer, San Francisco, Calif.), and the DNA concentration is adjusted to 100 μl by dilution with TE buffer. The purified pTrcHis plasmid is stored at −20° C.

Vector Preparation

Two μg of the purified pTrcHis plasmid is digested at 37° C. for 1-4 hours in a total volume of 50 μl containing 5 U of two restriction enzymes in 100 mM Tris-HCl (pH 7.5), 50 mM NaCl, 10 mM $MgCl_2$, 1 mM DTT and 100 μg/ml BSA. The particular pair of restriction enzymes used depends on the sequence of the primers and the sequence of the ORF; the goal being to use primers that would not cut the ORFs. The restricted vector is verified by electrophoresing 1 μl of the digestion reaction through a 1% (w/v) agarose gel in 1×TAE buffer at 90V for 1 hour. The electrophoresed DNA is stained with 1 μg/ml ethidium bromide and is viewed over ultraviolet (UV) light.

Linearised pTrcHis vector is purified using the Ultra-Clean® PCR Clean-up Kit (Mo Bio Laboratories, Carlsbad, Calif.), Briefly, the restriction reaction (50 μl) is mixed with 250 μl SpinBind buffer B1, and the entire volume is added to a spin-colunm. After centrifugation at 8,000×g for 1 minute, the flow-through is discarded and 300 μl SpinClean buffer B2 is added to the column, The column is centrifuged as before, and the flow-through is discarded before drying the column at 20,000×g for 3 minutes. The purified vector is eluted from the column with 50 μl TE buffer. Purified linear vector is quantified using a fluorometer, and the DNA concentration is adjusted to 50 μl/ml by dilution with TE buffer, The purified restricted vector is stored at −20° C.

Primer Design for Insert Preparation

Primer pairs are designed to amplify as much of the coding region of the target gene as possible using genomic DNA as the starting point. All primers sequences include terminal restriction enzyme sites to enable cohesive-end ligation of the resultant amplicon into the linearised pTrcHis vector. The primers are tested using Amplify 1.2 (University of Wisconsin, Madison, Wis.) and the theoretical amplicon sequence is inserted into the appropriate position in the pTrcHis vector sequence. Deduced translation of the chimeric pTrcHis expression cassette is performed using Vector NTI version 6 (InforMax) to confirm that the gene inserts would be in the correct reading frame. Table 3 also provides the gene size, the protein size, the predicted molecular weight of the native protein in daltons and the predicted pI of the protein. It is noted that the histidine-fusion of the recombinant protein adds approximately 4 kDa to the native protein's predicted molecular weight.

TABLE 3

| Gene | Gene size (bp) | Protein size (aa) | Predicted MW of native protein (Da) | Predicted pI |
| --- | --- | --- | --- | --- |
| NAV-H40 | 1815 | 605 | 97,733 | 9.4853 |
| NAV-H41 | 1068 | 356 | 39,870 | 5.2168 |
| NAV-H44 | 2940 | 980 | 113,722 | 5.1864 |
| NAV-H62 | 1014 | 338 | 37642 | 4.3944 |
| NAV-H64 | 1011 | 337 | 36468 | 4.4953 |
| NAV-H66 | 264 | 88 | 10629 | 9.3027 |
| NAV-H69 | 1080 | 360 | 41525 | 5.7123 |
| NAV-H73 | 258 | 86 | 10527 | 9.5920 |

Amplification of the Gene Inserts

Using genomic DNA, all target gene inserts are amplified by PCR in a 100 μl total volume using Taq DNA polymerase (Biotech International) and Pfu DNA polymerase (Promega, Madison, Wisc.). The amplification mixture consists of 1×PCR buffer (containing 1.5 mM of $MgCl_2$), 1 U of Taq DNA polymerase, 0.01 U Pfu DNA polymerase, 0.2 mM of each dNTP (Amersham Pharmacia Biotech), 0.5 μM of the appropriate primer pair and 1 μl of purified chromosomal DNA. The chromosomal DNA is prepared from the same *B. hyodysenteriae* strain used for genome sequencing. Cycling conditions involve an initial template denaturation step of 5 minutes at 94° C., followed by 35 cycles of denaturation at 94° C. for 30 seconds, annealing at 50° C. for 15 seconds, and primer extension at 68° C. for 4 minutes, The PCR products are subjected to electrophoresis in 1% (w/v agarose gels in 1×TAE buffer, are stained with a 1 μl/ml ethidium bromide solution and are viewed over UV light. After verifying the presence of the correct size PCR product, the PCR reaction is purified using the UltraClean® PCR Clean-up Kit (Mo Bio Laboratories, Carlsbad, Calif.), The PCR reaction (100 μl) is mixed with 500 μl SpinBind buffer B1, and the entire volume is added to a spin-column. After centrifugation at 8,000×g for 1 minute, the flow-through is discarded, and 300 μl SpinClean buffer B2 is added to the column. The column is centrifuged as before and the flow-through is discarded before drying the column at 20,000×g for 3 minutes. The purified vector is eluted from the column with 1000 μl TE buffer.

Restriction Enzyme Digestion of the Gene Inserts

Thirty μl of the purified PCR product are digested in a 50 μl total volume with 1 U of each restriction enzyme compatible with the terminal restriction endonuclease recognition site determined by the cloning oligonucleotide primer. The restriction reaction consists of 100 mM Tris-HCl (pH 7.5), 50 mM NaCl, 10 mM $MgCl_2$, 1 mM DTT and 100 μg/ml BSA with 1 U of each restriction enzyme at 37° C. for 1-4 hours, The digested insert DNA are purified using the UltraClean® PCR Clean-up Kit (see above), Purified digested insert DNA are quantified using the fluorometer, and the DNA concentration is adjusted to 20 μg/ml by dilution with TE buffer, The purified restricted insert DNA are used immediately for vector ligation.

Ligation of the Gene Inserts into the pTrcHis Vector

Ligation reactions are all performed in a total volume of 20 μl. One hundred ng of linearised pTrcHis is incubated with 20 ng of restricted insert at 16° C. for 16 hours in 30 mM Tris-HCl (pH 7.8), 10 mM $MgCl_2$, 10 mM DTT and 1 mM ATP containing 1 U of T4 DNA ligase (Promega). An identical ligation reaction containing no insert DNA is also included as a vector re-circularisation negative control. The appropriate restriction enzyme is used for each reaction.

Transformation of pTrcHis Ligations into *E. Coli* Cells

Competent *E. coli* JM109 (Promega) cells are thawed from −80° C. storage on ice and then 50 µl of the cells are transferred into ice-cold 1.5 ml microfuge tubes containing 5 µl of the overnight ligation reactions (equivalent to 25 ng of pTrcHis vector). The tubes are mixed by gently tapping the bottom of each tube on the bench and left on ice for 30 minutes. The cells are then heat-shocked by placing the tubes into a 42° C. water bath for 45 seconds before returning the tube to ice for 2 minutes. The transformed cells are recovered in 1 ml LB broth for 1 hour at 37° C. with gentle mixing. The recovered cells are harvested at 2,500×g for 5 minutes, and the cells are resuspended in 50 µl of fresh LB broth. The entire 50 µl of resuspended cells are spread evenly onto a LB agar plate containing 100 mg/l ampicillin using a sterile glass rod. Plates are incubated at 37° C. for 16 hours.

Detection of Recombinant pTrcHis Constructs in *E. Coli* by PCR

Twelve single transformant colonies for each construct are streaked onto fresh LB agar plates containing 100 mg/l ampicillin and incubated at 37° C. for 16 hours. A single colony from each transformation event is resuspended in 50 µl of TE buffer and is boiled for 1 minute. Two µl of boiled cells are used as template for PCR. The amplification mixture consists of 1×PCR buffer (containing 1.5 mM of $MgCl_2$), 1 U of Taq DNA polymerase, 0.2 mM of each dNTP, 0.5 µM of the pTrcHis-F primer (5'-CAATTTATCAGACAATCTGTGTG-3' SEQ ID NO: 107) and 0.5 µM of the pTrcHis-R primer (5'-TGCCTGGCAGTTCCCTACTCTCG-3' SEQ ID NO: 108). Cycling conditions involve an initial template denaturation step of 5 minutes at 94° C., followed by 35 cycles of denaturation at 94° C. for 30 seconds, annealing at 60° C. for 15 seconds, and a primer extension at 72° C. for 1 minute. The PCR products are subjected to electrophoresis in 1% (w/v) agarose gels in 1×TAE buffer, are stained with a 1 µg/ml ethidium bromide solution and are viewed over UV light. Cloning of the various inserts into the pTrcHis expression vector produces recombinant constructs of various sizes.

Pilot Expression of Recombinant His-Tagged Proteins

Five to ten isolated colonies of recombinant pTrcHis construct in *E. coli* JM109 are inoculated into 3 ml LB broth in a 5 ml tube containing 100 mg/l ampicillin and 1 mM IPTG and incubated at 37° C. for 16 hours with shaking. The cells are harvested by centrifugation at 5,000×g for 10 minutes at 4° C. The supernatant is discarded, and each pellet is resuspended with 10 µl Ni—NTA denaturing lysis buffer (100 mM $NaH_2PO_4$, 10 mM Tris-HCl, 8 M urea, pH 8.0). After vortexing the tube for 1 minute, the cellular debris is pelleted by centrifugation at 10,000×g for 10 minute at 4° C. The supernatant is transferred to a new tube and stored at −20° C. until analysis.

Sodium Dodecyl Sulfate Polyacrylamide Gel Electrophoresis (SDS-Page)

SDS-PAGE analysis of protein is performed using a discontinuous Tris-glycine buffer system. Thirty µl of protein sample are mixed with 10 µl 4× sample treatment buffer (250 mM Tris-HCl (pH 6.0), 8% (w/v) SDS, 200 mM OTT, 40% (v/v) glycerol and 0.04% (w/v) bromophenol blue). Samples are boiled for 5 minutes immediately prior to loading 10 µl of the sample into wells in the gel. The gel comprises a stacking gel (125 mM Tris-HCl ph 6.8, 4% w/v acylamide, 0.15% w/v bis-acrylamide and 0.1% w/v SDS) and a separating gel (375 mM Tris-HCl pH 8.8, 12% w/v acylamide, 0.31% w/v bis-acrylamide and 0.1% SDS). These gels are polymerised by the addition of 0.1% (v/v) TEMED and 0.05% (w/v) freshly prepared ammonium sulphate solution and cast into the mini-Protean® dual slab cell (Bio-Rad, Hercules, Calif.). Samples are run at 150 V at room temperature (RT) until the bromophenol blue dye reaches the bottom of the gel. Pre-stained molecular weight standards are electrophoresed in parallel with the samples in order to allow molecular weight estimations. After eleetrophoresis, the gel is immediately stained using Coomassie Brilliant Blue G250 (Bio-Rad) or is subjected to electro-transfer onto nitrocellulose membrane for Western blotting.

Western Blot Analysis

Electrophoretic transfer of separated proteins from the SDS-PAGE gel to nitrocellulose membrane is performed using the Towbin transfer buffer system. After electrophoresis, the gel is equilibrated in transfer buffer (25 mM Tris, 192 m/M glycine, 20% v/v methanol, pH 8.3) for 15 minutes. The proteins in the gel are electro-transferred to nitrocellulose membrane (Protran, Schleicher and Schuell BioScience, Inc., Keene, N.H.) using the mini-Protean® transblot apparatus (Bio-Rad) at 30 V overnight at 4° C. The freshly transferred nitrocellulose membrane containing the separated proteins is blocked with 10 ml of Tris-buffered saline (TBS) containing 5% (w/v) skim milk powder for 1 hour at room temperature. The membrane is washed with TBS containing 0.1% (v/v) Tween® 20 (TBST) and then is incubated with 10 mL mouse anti-his antibody (diluted 5,000-fold with TBST) for 1 hour at room temperature. After washing three times for 5 minutes with TBST, the membrane is incubated with 10 mL goat anti-mouse IgG (whole molecule)-AP diluted 5,000-fold in TBST for 1 hour at RT. The membrane is developed using the Alkaline Phosphatase Substrate Kit (Bio-Rad). The development reaction is stopped by washing the membrane with distilled water. The membrane is then dried and scanned for presentation.

Verification of Reading Frame of the Recombinant pTrcHis Constructs by Direct Sequence Analysis Two transformant clones for each construct which produced the correct sized PCR products are inoculated into 10 ml LB broth containing 100 mg/l ampicillin and incubated at 37° C. for 12 hours with shaking. The entire overnight cultures are centrifuged at 5,000×g for 10 minutes, and the plasmid contained in the cells are extracted using the QIAprep® Spin Miniprep Kit as described previously. The purified plasmid is quantified using a fluorometer. Both purified plasmids are subjected to automated direct sequencing of the pTrcHis expression cassette using the pTrcHis-F and pTrcHis-R primers. Each sequencing reaction is performed in a 10 J.11 volume consisting of 200 ng of plasmid DNA, 2 pmol of primer, and 4 J.11 of the ABI PRISM™ BigDye® Terminator Cycle Sequencing Ready Reaction Mix (PE Applied Biosystems, Foster City, Calif.). Cycling conditions involve a 2 minute denaturing step at 96° C., followed by 25 cycles of denaturation at 96° C. for 10 seconds, and a combined primer annealing and extension step at 60° C. for 4 minutes. Residual dye terminators are removed from the sequencing products by precipitation with 95% (v/v) ethanol containing 85 mM sodium acetate (pH 5.2), 3 mM EDTA (pH 8), and vacuum dried. The plasmids are sequenced in duplicate using each primer. Sequencing products are analysed using an ABI 373A DNA Sequencer (PB Applied Biosystems). Nucleotide sequencing of the pTrcHis is performed to verify that the expression cassette is in the correct reading frame for each constructs.

Expression and Purification of Recombinant His-Tagged Proteins

A single colony of the recombinant pTrcHis construct in *E. coli* JM 109 is inoculated into 50 ml LB broth in a 250 ml conical flask containing 100 mg/l ampicillin and incubated at 37° C. for 16 hours with shaking. A 2 l conical flask containing 1 l of LB broth supplemented with 100 mg/l ampicillin is inoculated with 10 ml of the overnight culture and incubated at 37° C. until the optical density of the cells at 600 nm is 0.5 (approximately 3-4 hours). The culture is then induced by adding IPTG to a final concentration of 1 mM, and the cells are returned to 37° C. with shaking. After 5 hours of induction, the culture is transferred to 250 ml centrifuge bottles, and the bottles are centrifuged at 5,000×g for 20 minutes at 4° C. The supernatant is discarded, and each pellet is resuspended with 8 ml Ni—NTA denaturing lysis buffer (100 mM $NaH_2PO_4$, 10 mM Tris-HCl, 8 M urea, pH 8.0). The resuspended cells are stored at −20° C. overnight.

The cell suspension is removed from −20° C. storage and thawed on ice. The cell lysate is then sonicated on ice 3 times for 30 seconds with 1 minute incubation on ice between sonication rounds. The lysed cells are cleared by centrifugation at 20,000×g for 10 minutes at 4° C., and the supernatant is transferred to a 15 ml column containing a 0.5 ml bed volume of Ni—NTA agarose resin (Qiagen). The recombinant $His_6$-tagged protein is allowed to bind to the resin for 1 hour at 4° C. with end-over-end mixing. The resin is then washed with 30 ml of Ni—NTA denaturing wash buffer (100 mM $NaH_2PO_4$, 10 mM Tris-HCl, 8 M urea, pH 6.3) before elution with 12 ml of Ni—NTA denaturing elution buffer (100 mM $NaH_2PO_4$, 10 mM Tris-HCl, 8 M urea, pH 4.5). Four 3 ml fractions of the eluate are collected and stored at 4° C. Thirty μl of each eluate is treated with 10 μl of 4× sample treatment buffer and boiled for 5 minutes. The samples are subjected to SDS-PAGE and stained with Coomassie Brilliant Blue G250 (Bio-Rad). The stained gel is equilibrated in distilled water for 1 hour and dried between two sheets of cellulose overnight at RT.

Expression of the selected recombinant *E. coli* clones is performed in medium-scale to generate sufficient recombinant protein for vaccination of mice (see below).

Dialysis and Lyophilisation of the Purified Recombinant His-Tagged Protein

The eluted proteins are pooled and transferred into a hydrated dialysis tube (Spectrum Laboratories, Inc., Los Angeles, Calif.) with a molecular weight cut-off (MWCO) of 3,500 Da. A 200 μl aliquot of the pooled eluate is taken and quantified using a commercial Protein Assay (Bio-Rad). The proteins are dialysed against 2 l of distilled water at 4° C. with stirring. The dialysis buffer is changed 8 times at 12-hourly intervals. The dialysed proteins are transferred from the dialysis tube into a 50 ml centrifuge tubes (40 ml maximum volume), and the tubes are placed at −80° C. overnight. Tubes are placed into a MAXI freeze-drier (Heto-Holten, Allerod, Denmark) and lyophilised to dryness. The lyophilised proteins are then re-hydrated with PBS to a calculated concentration of 2 mg/ml and stored at −20° C. Following dialysis and lyophilisation, stable recombinant antigen is successfully produced.

Eight of the eighteen genes are successfully cloned into the *E. coli* Expression System and recombinant protein can be expressed stably from these clones.

Serology Using Purified Recombinant Protein

Twenty μg of purified recombinant protein is loaded into a 7 cm IEF well, electrophoresed through a 10% (w/v) SDS-PAGE gel, and electro-transferred to nitrocellulose membrane. The membrane is blocked with TBS-skim milk (5% w/v) and assembled into the multi-screen apparatus (Bio-Rad). The wells are incubated with 100 μl of diluted pig serum (100-fold) for 1 hour at room temperature. The pig serum is obtained from high health status pigs (n=3), experimentally challenged pigs showing clinical SD (n=5), naturally infected seroconverting pigs (n=5), and pigs recovered from natural infection (n=4). The membrane then is removed from the apparatus and washed three times with TBST (0.1% v/v) before incubating with 10 ml of goat anti-swine IgG (whole molecule)-AP (5,000-fold) for 1 hour at RT. The membrane is washed three times with TBST before color development using an Alkaline Phosphatase Substrate Kit (Bio-Rad). The membrane is washed with tap water when sufficient development has occurred, dried and scanned for presentation.

The reactivity of the pig serum obtained from animal of differing health status is shown in the table below. All proteins are recognised by 100% of the panel of serum thus indicating that the genes are expressed in vivo and that they are able to induce a systemic immune response following exposure to the spirochaete.

TABLE 4

Gene distribution and serologic reactivity of the eight successfully expressed *B. hyodysenteriae* vaccine candidates.

| Gene | Distribution (%) | Serology (%) |
| --- | --- | --- |
| NAV-H40 | 100 | 100% |
| NAV-H41 | 83 | 100% |
| NAV-H44 | 100 | 100% |
| NAV-H62 | 96 | 100% |
| NAV-H64 | 91 | 100% |
| NAV-H66 | 96 | 100% |
| NAV-H69 | 91 | 100% |
| NAV-H73 | 87 | 100% |

The gene distribution was analysed by PCR using a panel of 23 different strains. Serology was performed using 19 serum samples from five different categories of disease.

Vaccination of Mice Using the Purified Recombinant his-Tagged Proteins

For each of the purified recombinant his-tagged proteins, ten mice are systemically and orally immunized to determine whether the recombinant protein would be immunogenic. The recombinant protein is emulsified with 30% (v/v) water in oil adjuvant and injected intramuscularly into the quadraceps muscle of ten mice (Balb/cJ: 5 weeks old males). All mice receive 100 μg of protein in a total volume of 100 μl. Three weeks after the first vaccination, all mice receive a second intramuscular vaccination identical to the first vaccination. All mice are killed two weeks after the second vaccination. Sera are obtained from the heart at post-mortem and tested in Western blot analysis for antibodies against cellular extracts of *B. hyodysenteriae*.

Western Blot Analysis

Twenty μg of purified recombinant protein is loaded into a 7 cm IEF well, electrophoresed through a 10% (w/v) SDS-PAGE gel, and electro-transferred to nitrocellulose membrane. The membrane is blocked with TBS-skim milk (5% w/v) and assembled into the multi-screen apparatus (Bio-Rad). The wells are incubated with 100 μl of diluted mouse serum (100-fold) for 1 hour at room temperature. The membrane is removed from the apparatus and washed three times with TBST (0.1% v/v) before incubating with 10 ml of goat anti-mouse IgG (whole molecule)-AP (5,000-fold) for 1 hour at room temperature. The membrane is washed three times with TBST before color development using an Alkaline Phosphatase Substrate Kit (Bio-Rad). The membrane is washed with tap water when sufficient development has occurred, dried and scanned for presentation.

Western blot analysis shows a significant increase in antibody reactivity in the mice towards the recombinant vaccine antigens following vaccination. All the mice recognise recombinant proteins which are similar in molecular weight to that of the coomassie blue stained purified recombinant proteins. These experiments provide evidence that the recombinant proteins are immunogenic when used to vaccinate mice and that the vaccination protocol employed can induce specific circulating antibody titres against the antigen. The results indicate that the recombinant proteins can be useful in an effective vaccine for animal species from being colonised by B. hyodysenteriae.

Vaccination of Pigs Using the Purified Recombinant his-Tagged Proteins

For each of the purified recombinant his-tagged proteins, ten sero-negative pigs are injected intramuscularly with 1 mg of the particular antigen in 1 ml vaccine volume. The antigen is emulsified with an equal volume of a water-in-oil adjuvant. The pigs are vaccinated at three weeks of age and again at six weeks of age. A second group of ten sero-negative pigs is used as negative controls and are left unvaccinated. All pigs are challenged with 100 ml of an active B. hyodysenteriae culture (~$10^9$ cells/ml) at eight weeks of age, and the pigs are observed for clinical signed of swine dysentery during the experiment (up to six weeks post-challenge) and at post-morten examination.

Diagnostic Kit

Serum is obtained from pigs in a piggery with known infection of B. hyodysenteriae, from pigs known to have not been infected with B. hyodysenteriae, and from pigs in piggery with unknown infection with B. hyodysenteriae. Twenty µg of purified recombinant protein is loaded into a 7 cm IEF well, electrophoresed through a 10% (w/v) SDS-PAGE gel, and electro-transferred to nitrocellulose membrane. The membrane is blocked with TBS-skim milk (5% w/v) and assembled into the multi-screen apparatus (Bio-Rad). The wells are incubated with 100 µl of diluted pig serum (100-fold) for 1 hour at room temperature. The membrane then is removed from the apparatus and washed three times with TBST (0.1% v/v) before incubating with 10 ml of goat anti-swine IgG (whole molecule)-AP (5,000-fold) for 1 hour at room temperature. The membrane is washed three times with TBST before color development using an Alkaline Phosphatase Substrate Kit (Bio-Rad). The membrane is washed with tap water when sufficient development has occurred, dried and scanned for presentation. One can determine if pigs are infected with B. hyodysenteriae by comparing the results to the positive and negative control.

While this invention has been described with a reference to specific embodiments, it will be obvious to those of ordinary skill in the art that variations in these methods and compositions may be used and that it is intended that the invention may be practiced otherwise than as specifically described herein. Accordingly this invention includes all modifications encompassed within the spirit and scope of the invention as defined by the claims.

The invention claimed is:

1. An isolated polypeptide comprising the full length of the amino acid sequence SEQ ID NO: 60 and a heterologous polypeptide that permits the detection, isolation, solubilization, or stabilization of the isolated polypeptide.

2. An isolated polypeptide comprising a sequence that is at least 70% homologous to a polypeptide with the amino acid sequence SEQ ID NO: 60, and heterologous polypeptide that permits the detection, isolation, solubilization, or stabilization of the isolated polypeptide.

3. An isolated polypeptide comprising a sequence that is at least 80% homologous to a polypeptide with the amino acid sequence SEQ ID NO: 60, and a heterologous polypeptide that permits the detection, isolation, solubilization, or stabilization of the isolated polypeptide.

4. An isolated polypeptide comprising a sequence that is at least 90% homologous to a polypeptide with the amino acid sequence SEQ ID NO: 60, and a heterologous polypeptide that permits the detection, isolation, solubilization, or stabilization of the isolated polypeptide.

5. An immunogenic composition comprising the polypeptide claim 1.

6. A method of generating an immune response to a *Brachyspira* infection in an animal comprising administering to said animal the polypeptide of claim 1.

7. An immunogenic composition comprising the polypeptide of claim 2.

8. A method of generating an immune response to a *Brachyspira* infection in an animal comprising administering to said animal the polypeptide of claim 2.

9. An immunogenic composition comprising the polypeptide of claim 3.

10. A method of generating an immune response to a *Brachyspira* infection in an animal comprising administering to said animal the polypeptide of claim 3.

11. An immunogenic composition comprising the polypeptide of claim 4.

12. A method of generating an immune response to a *Brachyspira* infection in an animal comprising administering to said animal the polypeptide of claim 4.

* * * * *

SEQUENCE LISTING

```
<160> NUMBER OF SEQ ID NOS: 94

<210> SEQ ID NO 1
<211> LENGTH: 600
<212> TYPE: DNA
<213> ORGANISM: Brachyspira hyodysenteriae

<400> SEQUENCE: 1
atgggtatta gtttagatcc tcaaatcaga tactatacag gaatagattt gctcaatcaa        60
gtaagattaa tagttaaata tggtatgaat caaactaaaa ctgcatcaga aacatataca       120
gcttcttctt ttggttttga tttcagatta tatttcggag ctatggttgg aaatgttact       180
cttaatcctt tcatcaaagt aacttatgat acttctttag gtgctaaagg taaatctact       240
ggaagttatg aagtattatc agacagtgtt gttattccta caacaactgc agctgattta       300
cttgatagag aaacttatac tttatctata cttcctactt tagctttaga ggcaagcagt       360
gatgtagttt ctctttattt agagcctgga ttaggttatt ctatttatga tgatggtaga       420
aaaggttcta aacttaatca ttctttagct tggtcagctt atgcagaact ttatattact       480
cctgttgaag atttagaatg gtattttgag atggatgtaa ataatgaggg aggagttcct       540
attagctttg catctactac aggtattact tggtacttgc cttctttcgg agcagcagag       600

<210> SEQ ID NO 2
<211> LENGTH: 200
<212> TYPE: PRT
<213> ORGANISM: Brachyspira hyodysenteriae

<400> SEQUENCE: 2

Met Gly Ile Ser Leu Asp Pro Gln Ile Arg Tyr Tyr Thr Gly Ile Asp
  1               5                  10                  15

Leu Leu Asn Gln Val Arg Leu Ile Val Lys Tyr Gly Met Asn Gln Thr
             20                  25                  30

Lys Thr Ala Ser Glu Thr Tyr Thr Ala Ser Ser Phe Gly Phe Asp Phe
         35                  40                  45
```

```
Arg Leu Tyr Phe Gly Ala Met Val Gly Asn Val Thr Leu Asn Pro Phe
     50                  55                  60

Ile Lys Val Thr Tyr Asp Thr Ser Leu Gly Ala Lys Gly Lys Ser Thr
 65              70                  75                  80

Gly Ser Tyr Glu Val Leu Ser Asp Ser Val Ile Pro Thr Thr Thr
                 85                  90                  95

Ala Ala Asp Leu Leu Asp Arg Glu Thr Tyr Thr Leu Ser Ile Leu Pro
             100                 105                 110

Thr Leu Ala Leu Glu Ala Ser Ser Asp Val Val Ser Leu Tyr Leu Glu
            115                 120                 125

Pro Gly Leu Gly Tyr Ser Ile Tyr Asp Asp Gly Arg Lys Gly Ser Lys
        130                 135                 140

Leu Asn His Ser Leu Ala Trp Ser Ala Tyr Ala Glu Leu Tyr Ile Thr
145             150                 155                 160

Pro Val Glu Asp Leu Glu Trp Tyr Phe Glu Met Asp Val Asn Asn Glu
                165                 170                 175

Gly Gly Val Pro Ile Ser Phe Ala Ser Thr Thr Gly Ile Thr Trp Tyr
            180                 185                 190

Leu Pro Ser Phe Gly Ala Ala Glu
        195                 200

<210> SEQ ID NO 3
<211> LENGTH: 717
<212> TYPE: DNA
<213> ORGANISM: Brachyspira hyodysenteriae

<400> SEQUENCE: 3
atgaaactac aaataggaat tttaactata gtaaatttaa tagcatttat accactatta       60
tatatgtttg atatatttgg tgttgttaat tattatactt taatgcgtaa taaaatagca      120
cctaatgtac cgggtttttt aacaagattc actcaaaaac ctagagtaga agatatgact      180
cttttggcta gagaagatct taataaaatg agagaatcat tcaatttaag agaaaaagat      240
ttgcaggctc aggaatcttt aatagcaagc agagcaatag aattgaacac tcaatctgaa      300
ttgatagaac aagacagaca aaatctttta aatgcttggt ctaattatca agctactatg      360
gatgaatctt ctcagtatca attagtatta actgaccttg ctaataaaat caatagtatg      420
cctcctcaaa gctctgtggc attacttaat cagttagctg ctaatggttc tgatgactta      480
atcatagatg tattattaga aatggactct agctgctgct gaaggaag aaacagtact       540 acttcttacc ttttaagctt aatggatccg aatgttgctg ctagaatatt agaaaaatat      600
gaagcaagat ctaatcctgg aaataataca gtaccttctt cacctaatga cttccctaat      660
tatatgcctg ataataatga cgctatgtta atgaaggca taatggatat gggagca         717

<210> SEQ ID NO 4
<211> LENGTH: 239
<212> TYPE: PRT
<213> ORGANISM: Brachyspira hyodysenteriae

<400> SEQUENCE: 4

Met Lys Leu Gln Ile Gly Ile Leu Thr Ile Val Asn Leu Ile Ala Phe
 1               5                  10                  15

Ile Pro Leu Leu Tyr Met Phe Asp Ile Phe Gly Val Val Asn Tyr Tyr
             20                  25                  30

Thr Leu Met Arg Asn Lys Ile Ala Pro Asn Val Pro Gly Phe Leu Thr
         35                  40                  45
```

```
Arg Phe Thr Gln Lys Pro Arg Val Glu Asp Met Thr Leu Leu Ala Arg
    50                  55                  60

Glu Asp Leu Asn Lys Met Arg Glu Ser Phe Asn Leu Arg Glu Lys Asp
65                  70                  75                  80

Leu Gln Ala Gln Glu Ser Leu Ile Ala Ser Arg Ala Ile Glu Leu Asn
                85                  90                  95

Thr Gln Ser Glu Leu Ile Glu Gln Asp Arg Gln Asn Leu Leu Asn Ala
            100                 105                 110

Trp Ser Asn Tyr Gln Ala Thr Met Asp Glu Ser Ser Gln Tyr Gln Leu
        115                 120                 125

Val Leu Thr Asp Leu Ala Asn Lys Ile Asn Ser Met Pro Pro Gln Ser
    130                 135                 140

Ser Val Ala Leu Leu Asn Gln Leu Ala Ala Asn Gly Ser Asp Asp Leu
145                 150                 155                 160

Ile Ile Asp Val Leu Leu Glu Met Asp Ser Ile Ala Ala Ala Glu Gly
                165                 170                 175

Arg Asn Ser Thr Thr Ser Tyr Leu Leu Ser Leu Met Asp Pro Asn Val
            180                 185                 190

Ala Ala Arg Ile Leu Glu Lys Tyr Glu Ala Arg Ser Asn Pro Gly Asn
        195                 200                 205

Asn Thr Val Pro Ser Ser Pro Asn Asp Phe Pro Asn Tyr Met Pro Asp
    210                 215                 220

Asn Asn Asp Ala Met Leu Asn Glu Gly Ile Met Asp Met Gly Ala
225                 230                 235
```

<210> SEQ ID NO 5
<211> LENGTH: 4671
<212> TYPE: DNA
<213> ORGANISM: Brachyspira hyodysenteriae

<400> SEQUENCE: 5

```
atgtcagatg ttgatgtatt gttaaaagat gaagttaaag ctctatcaag cagattatca     60
gattttgaag agagaataaa agatgatata gtaagagatt tagatgaata ttctatagaa    120
ttaaataatc ttactgataa tgtaggaaaa ttaaattcaa gaatagatga tgttaaatca    180
caaatagaag atagcattaa taaatcttct gaattggaaa ctcttatttc tagtgaaaaa    240
gaagaattag ataataaact atctactatt aaggatgagt tagtatctaa gtctgaaaat    300
gatgatacta tagagaaatt attcactcaa gaaaaagaaa aattaaatga acttttcaat    360
caaataaaag atgataataa agagttcaga tatagattag agaaacgtgt tgcttatttt    420
gaggacactt ggtcagacag cagcagattg aaaaatattt tctcaactga tataagagaa    480
caattggata atatcagaaa tgataatgag attaaatttg aaaattctat aaattatttg    540
aaagataaag tagaatctat agataatgat atatctaatt ggaaagaaaa cactgttgat    600
gaattagtta aacaattagg tgaagctaga gaaagcatat ctaattattt gaatgattca    660
gagataaaag gaaaagaatt agtagataat cttttatcta aaatagatga aaaagaaaat    720
agcatgtatc agactttaga agataaagag aagaacatgt atcaaacttt agatgataaa    780
gaaaagagta tgtatcaaac tctagatgat agagcaagaa acatgtataa atctttagat    840
gaaaaagaaa agtctatata tgaaatctta gataataaag tacaggaaat agaaagcaga    900
ttatctctta ttgattctaa attgaatgat gatataactt ctaacttaga aaatctatat    960
gatatgctaa atgaagcagt agctaaatat gatgaagaga taaaaaatat tgagcattat   1020
```

| | |
|---|---|
| agattagatg agaataataa gattttagat gatattgata atgtaggaaa agaaataaga | 1080 |
| tcttcttatg aaaattattc taagcttata gaagaggttt ataataattc tcttaattca | 1140 |
| ttaaaagatt attctaattc tattaaagat gagatagaaa aatcaagaga agaaacagaa | 1200 |
| gaaagacact tgtctagtga gagagaatat attgatgagt atttgaaagg atattcagaa | 1260 |
| aaattagaat ctcaagtatc tgataagata aatatattga atgatgctaa aactgattta | 1320 |
| gataatatgt taaaatcttc ttttgatgat ttagaagcaa gatttaatga atctatgact | 1380 |
| aagtttgaag aatcttcaaa taacagagta ttcaaaactt tacaagatat agagaaaaaa | 1440 |
| gctgatgatg taatttatgg aaacaattat atctacaaga tagaagataa agtaaaagac | 1500 |
| ttctatggta aaatagatac taaactactt cattttgctg atagatatga tactttagag | 1560 |
| aaaaagatat atgatttaga gagcaatcaa aattatatat tcagactcga agataaaatt | 1620 |
| agagatttga atgaaaagct agatgataga ataacaaatg ttaatgaaag atatgataat | 1680 |
| ttaagaaaat cttttgatga taaatttgtt catatagaaa gtgctgtatt gaataatgag | 1740 |
| caagttcaga aattgagaga tgatttcatt attttcaaag atgatgtatt gaaagctaat | 1800 |
| agagataata taccagagct attcaataaa gaaaaagaaa aatttgaaga gttatttaat | 1860 |
| tcgttcgcta atgatataat atctaaatta gatacttcta atgctaatat agaagagttc | 1920 |
| aaaaatacta tgtatgatga aaagaattct atattagaaa atatggaatc atttagatat | 1980 |
| gagttagatg aattaaagaa caatgattct attgaagctt tagaagctga gaaagctaga | 2040 |
| ttagaagata ctttcaattc tttcagagaa gaatttgaaa gactttatga tttggaaagt | 2100 |
| gaagtttata atttgaaaag taatttagat ggtgttgatt ctaatttaag aagcgatgtt | 2160 |
| gataaattat ttgatgaagt ttctgagttt aaatatgctt tagaagaaaa aatagatatt | 2220 |
| ttagaagata atacagtttc tagagattta tttgatgatg acagagaaaa attatattct | 2280 |
| ttatatgatg aacttgaagc aggaaataaa gactttaaag atttaatgga taagagaata | 2340 |
| agttattttg aagatacttg gtctgatcct aataaggctt taaaacttta tgaaaatgct | 2400 |
| ttaacacctg aagtagataa tttgaaatct gaaatacttt ctaatgtaaa agatcaagta | 2460 |
| aatgaaaatag aaaagaactt atctgtttgg aaagatgata atttgtctct tcttttagag | 2520 |
| caattaaaag aggctaaaga aaatatcgat aactttatag aaagttctaa agacaagaag | 2580 |
| aatggtatta ttgccaaaat gatatcttct ataaaagagg aaatattagg caaagaaagt | 2640 |
| gagataaaata ctcgtcttga agaaaaactt tcttctgtta atgaaagaat tgctgattta | 2700 |
| gaaaatagat taacttctga tgttagcaga tttaataata tgatatctga agcagttgat | 2760 |
| aaatatgaag atgagcttaa gaatatagaa tcttatagat tagaagaaaa tgaatctata | 2820 |
| atgagaaatt tggaagatat tggaagaaat ataatttcaa attatgataa ttattctaaa | 2880 |
| atgctagatt ctgtttatga gaataataaa aatgctttag atgagtattc aaacagctta | 2940 |
| agaatagaaa tagaaaaagc tagagttgat actaataaag gttatataga tgaatatttg | 3000 |
| agtgaatatt cttctaaagt agaggctgat ataaagaaaa gactagaaga gcttgagaaa | 3060 |
| aataaatata atttagatgt tatgataaat gattcattta ataatttgaa tcaaagtatt | 3120 |
| aataatgcag tatctaaaat gatagaagat tctgattcta aattaagaga tgttatagat | 3180 |
| aatttagaag ttcagataaa tgatcttata gctaataaag aagaagaaat agttagcaga | 3240 |
| atatcagctt atgaaacaga tctaaaaaat gaacagtatt cttcacttga agatattaaa | 3300 |
| aatgagttat taggtctttta taatgagttt aaagagaatg ttaattatga taatttgaaa | 3360 |
| gatatatctg aaaaattaga tagtatagaa acttcattgt tagaagttaa tactcaatta | 3420 |

-continued

```
gaaaataaag ctaaagatat ttctgataga atagatttag aaaaagaaga attatatgct   3480
tctgttaata aattgtcttc agaatttgaa gatttcaaat caaatataga tgacagattc   3540
aaaactcaag taagcgattt tgtatctaat aatgagcata tattatcact ctttggtgaa   3600
tatagtgaga aaatttcttc tgtaactaat atattggaag acatagaaaa tgttaaagta   3660
tctttaattg aagaaataaa taaagtaaaa gaagaaatag ataataaata ttcaagtctt   3720
actaaagatt ttgataaatc aatagatgat ataaaagatg ctgtattaga taagaataat   3780
atacttcaat attatataaa tgaaaagaa ttgttatgga agagattga tgctttgaaa    3840 gctacttttg cttcaatgaa agataatata ttgaatgcta atgaagcagt tgctaaatat   3900
gctccttcta tcattgatag tgagaaagtt cgtatacagt ctgttataga cgatgtattt   3960
gaaactttaa gtgctaaaat aaataataat gaagacagta tttctaattt agaatcttct   4020
ttctctgaat ataaatctct tatatcagat gctatagacg gatttaaaga tgaaatttct   4080
tctataagaa atagtaataa ctatgatgat ttaattgaag agagaaatag attggaagaa   4140
tcatttaatt ctcttaaaga tgatttctca aaaatagaag atttggaaaa agatttacat   4200
cttgttaaag ctaagttaaa aggtgatgac agcagcttga ttgatgaagt tatgagactt   4260
tctgatgagc ttgaaatctt gaaagataat gtatcaaata tgaataatac agataataat   4320
gtaaatgata ataatgatat tgatgctatt tatgaagatt tcaaacagtt aaatgaaagt   4380
ttagaatcat tcaaagaaac tgttattcct caattatcta cttttagtaa attggaagat   4440
aagatatcag aaaatagaga ggaaatctat aaatatatca atagtataat gtattcttta   4500
cctgaagctt atataagcag agaagagata tctaatttag aaaataaatt atatgataca   4560
tttaataact tcaatgacgg catagtatct ataagaatg atttagtttt ctatatagag    4620
aaagacacta agatttcaa agatagaata gaaagagaag atagagttct t            4671
```

<210> SEQ ID NO 6
<211> LENGTH: 1557
<212> TYPE: PRT
<213> ORGANISM: Brachyspira hyodysenteriae

<400> SEQUENCE: 6

```
Met Ser Asp Val Asp Val Leu Leu Lys Asp Glu Val Lys Ala Leu Ser
 1               5                  10                  15

Ser Arg Leu Ser Asp Phe Glu Glu Arg Ile Lys Asp Ile Val Arg
            20                  25                  30

Asp Leu Asp Glu Tyr Ser Ile Glu Leu Asn Asn Leu Thr Asp Asn Val
        35                  40                  45

Gly Lys Leu Asn Ser Arg Ile Asp Asp Val Lys Ser Gln Ile Glu Asp
    50                  55                  60

Ser Ile Asn Lys Ser Ser Glu Leu Glu Thr Leu Ile Ser Ser Glu Lys
65                  70                  75                  80

Glu Glu Leu Asp Asn Lys Leu Ser Thr Ile Lys Asp Glu Leu Val Ser
                85                  90                  95

Lys Ser Glu Asn Asp Asp Thr Ile Glu Lys Leu Phe Thr Gln Glu Lys
            100                 105                 110

Glu Lys Leu Asn Glu Leu Phe Asn Gln Ile Lys Asp Asp Asn Lys Glu
        115                 120                 125

Phe Arg Tyr Arg Leu Glu Lys Arg Val Ala Tyr Phe Glu Asp Thr Trp
    130                 135                 140

Ser Asp Ser Ser Arg Leu Lys Asn Ile Phe Ser Thr Asp Ile Arg Glu
```

```
            145                 150                 155                 160
        Gln Leu Asp Asn Ile Arg Asn Asp Asn Glu Ile Lys Phe Glu Asn Ser
                        165                 170                 175
        Ile Asn Tyr Leu Lys Asp Lys Val Glu Ser Ile Asp Asn Asp Ile Ser
                        180                 185                 190
        Asn Trp Lys Glu Asn Thr Val Asp Glu Leu Val Lys Gln Leu Gly Glu
                        195                 200                 205
        Ala Arg Glu Ser Ile Ser Asn Tyr Leu Asn Asp Ser Glu Ile Lys Gly
                210                 215                 220
        Lys Glu Leu Val Asp Asn Leu Leu Ser Lys Ile Asp Glu Lys Glu Asn
        225                 230                 235                 240
        Ser Met Tyr Gln Thr Leu Glu Asp Lys Glu Lys Asn Met Tyr Gln Thr
                        245                 250                 255
        Leu Asp Asp Lys Glu Lys Ser Met Tyr Gln Thr Leu Asp Asp Arg Ala
                        260                 265                 270
        Arg Asn Met Tyr Lys Ser Leu Asp Glu Lys Lys Ser Ile Tyr Glu
                        275                 280                 285
        Ile Leu Asp Asn Lys Val Gln Glu Ile Glu Ser Arg Leu Ser Leu Ile
                290                 295                 300
        Asp Ser Lys Leu Asn Asp Asp Ile Thr Ser Asn Leu Glu Asn Leu Tyr
        305                 310                 315                 320
        Asp Met Leu Asn Glu Ala Val Ala Lys Tyr Asp Glu Glu Ile Lys Asn
                        325                 330                 335
        Ile Glu His Tyr Arg Leu Asp Glu Asn Asn Lys Ile Leu Asp Asp Ile
                        340                 345                 350
        Asp Asn Val Gly Lys Glu Ile Arg Ser Ser Tyr Glu Asn Tyr Ser Lys
                        355                 360                 365
        Leu Ile Glu Glu Val Tyr Asn Asn Ser Leu Asn Ser Leu Lys Asp Tyr
                        370                 375                 380
        Ser Asn Ser Ile Lys Asp Glu Ile Glu Lys Ser Arg Glu Glu Thr Glu
        385                 390                 395                 400
        Glu Arg His Leu Ser Ser Glu Arg Glu Tyr Ile Asp Glu Tyr Leu Lys
                        405                 410                 415
        Gly Tyr Ser Glu Lys Leu Glu Ser Gln Val Ser Asp Lys Ile Asn Ile
                        420                 425                 430
        Leu Asn Asp Ala Lys Thr Asp Leu Asp Asn Met Leu Lys Ser Ser Phe
        435                 440                 445
        Asp Asp Leu Glu Ala Arg Phe Asn Glu Ser Met Thr Lys Phe Glu Glu
                        450                 455                 460
        Ser Ser Asn Asn Arg Val Phe Lys Thr Leu Gln Asp Ile Glu Lys Lys
        465                 470                 475                 480
        Ala Asp Asp Val Ile Tyr Gly Asn Asn Tyr Ile Tyr Lys Ile Glu Asp
                        485                 490                 495
        Lys Val Lys Asp Phe Tyr Gly Lys Ile Asp Thr Lys Leu Leu His Phe
                        500                 505                 510
        Ala Asp Arg Tyr Asp Thr Leu Glu Lys Lys Ile Tyr Asp Leu Glu Ser
                        515                 520                 525
        Asn Gln Asn Tyr Ile Phe Arg Leu Glu Asp Lys Ile Arg Asp Leu Asn
                        530                 535                 540
        Glu Lys Leu Asp Asp Arg Ile Thr Asn Val Asn Glu Arg Tyr Asp Asn
        545                 550                 555                 560
        Leu Arg Lys Ser Phe Asp Asp Lys Phe Val His Ile Glu Ser Ala Val
                        565                 570                 575
```

```
Leu Asn Asn Glu Gln Val Gln Lys Leu Arg Asp Asp Phe Ile Ile Phe
            580                 585                 590

Lys Asp Val Leu Lys Ala Asn Arg Asp Asn Ile Pro Glu Leu Phe
    595                 600                 605

Asn Lys Glu Lys Glu Lys Phe Glu Glu Leu Phe Asn Ser Phe Ala Asn
            610                 615                 620

Asp Ile Ile Ser Lys Leu Asp Thr Ser Asn Ala Asn Ile Glu Glu Phe
625                 630                 635                 640

Lys Asn Thr Met Tyr Asp Glu Lys Asn Ser Ile Leu Glu Asn Met Glu
            645                 650                 655

Ser Phe Arg Tyr Glu Leu Asp Glu Leu Lys Asn Asn Asp Ser Ile Glu
            660                 665                 670

Ala Leu Glu Ala Glu Lys Ala Arg Leu Glu Asp Thr Phe Asn Ser Phe
            675                 680                 685

Arg Glu Glu Phe Glu Arg Leu Tyr Asp Leu Glu Ser Glu Val Tyr Asn
            690                 695                 700

Leu Lys Ser Asn Leu Asp Gly Val Asp Ser Asn Leu Arg Ser Asp Val
705                 710                 715                 720

Asp Lys Leu Phe Asp Glu Val Ser Glu Phe Lys Tyr Ala Leu Glu Glu
            725                 730                 735

Lys Ile Asp Ile Leu Glu Asp Asn Thr Val Ser Arg Asp Leu Phe Asp
            740                 745                 750

Asp Asp Arg Glu Lys Leu Tyr Ser Leu Tyr Asp Glu Leu Glu Ala Gly
            755                 760                 765

Asn Lys Asp Phe Lys Asp Leu Met Asp Lys Arg Ile Ser Tyr Phe Glu
            770                 775                 780

Asp Thr Trp Ser Asp Pro Asn Lys Ala Leu Lys Leu Tyr Glu Asn Ala
785                 790                 795                 800

Leu Thr Pro Glu Val Asp Asn Leu Lys Ser Glu Ile Leu Ser Asn Val
            805                 810                 815

Lys Asp Gln Val Asn Glu Ile Glu Lys Asn Leu Ser Val Trp Lys Asp
            820                 825                 830

Asp Asn Leu Ser Leu Leu Leu Glu Gln Leu Lys Glu Ala Lys Glu Asn
            835                 840                 845

Ile Asp Asn Phe Ile Glu Ser Ser Lys Asp Lys Lys Asn Gly Ile Ile
850                 855                 860

Ala Lys Met Ile Ser Ser Ile Lys Glu Glu Ile Leu Gly Lys Glu Ser
865                 870                 875                 880

Glu Ile Asn Thr Arg Leu Glu Glu Lys Leu Ser Ser Val Asn Glu Arg
            885                 890                 895

Ile Ala Asp Leu Glu Asn Arg Leu Thr Ser Asp Val Ser Arg Phe Asn
            900                 905                 910

Asn Met Ile Ser Glu Ala Val Asp Lys Tyr Glu Asp Glu Leu Lys Asn
            915                 920                 925

Ile Glu Ser Tyr Arg Leu Glu Glu Asn Glu Ser Ile Met Arg Asn Leu
            930                 935                 940

Glu Asp Ile Gly Arg Asn Ile Ile Ser Asn Tyr Asp Asn Tyr Ser Lys
945                 950                 955                 960

Met Leu Asp Ser Val Tyr Glu Asn Asn Lys Asn Ala Leu Asp Glu Tyr
            965                 970                 975

Ser Asn Ser Leu Arg Ile Glu Ile Glu Lys Ala Arg Val Asp Thr Asn
            980                 985                 990
```

```
Lys Gly Tyr Ile Asp Glu Tyr Leu Ser Glu Tyr Ser Ser Lys Val Glu
            995                 1000                1005

Ala Asp Ile Lys Glu Arg Leu Glu Glu Leu Lys Asn Lys Tyr Asn
    1010                1015                1020

Leu Asp Val Met Ile Asn Asp Ser Phe Asn Asn Leu Asn Gln Ser Ile
1025                1030                1035                1040

Asn Asn Ala Val Ser Lys Met Ile Glu Asp Ser Asp Ser Lys Leu Arg
            1045                1050                1055

Asp Val Ile Asp Asn Leu Glu Val Gln Ile Asn Asp Leu Ile Ala Asn
    1060                1065                1070

Lys Glu Glu Glu Ile Val Ser Arg Ile Ser Ala Tyr Glu Thr Asp Leu
    1075                1080                1085

Lys Asn Glu Gln Tyr Ser Ser Leu Glu Asp Ile Lys Asn Glu Leu Leu
    1090                1095                1100

Gly Leu Tyr Asn Glu Phe Lys Glu Asn Val Asn Tyr Asp Asn Leu Lys
1105                1110                1115                1120

Asp Ile Ser Glu Lys Leu Asp Ser Ile Glu Thr Ser Leu Leu Glu Val
            1125                1130                1135

Asn Thr Gln Leu Glu Asn Lys Ala Lys Asp Ile Ser Asp Arg Ile Asp
            1140                1145                1150

Leu Glu Lys Glu Glu Leu Tyr Ala Ser Val Asn Lys Leu Ser Ser Glu
            1155                1160                1165

Phe Glu Asp Phe Lys Ser Asn Ile Asp Asp Arg Phe Lys Thr Gln Val
            1170                1175                1180

Ser Asp Phe Val Ser Asn Asn Glu His Ile Leu Ser Leu Phe Gly Glu
1185                1190                1195                1200

Tyr Ser Glu Lys Ile Ser Ser Val Thr Asn Ile Leu Glu Asp Ile Glu
            1205                1210                1215

Asn Val Lys Val Ser Leu Ile Glu Glu Ile Asn Lys Val Lys Glu Glu
            1220                1225                1230

Ile Asp Asn Lys Tyr Ser Ser Leu Thr Lys Asp Phe Asp Lys Ser Ile
            1235                1240                1245

Asp Asp Ile Lys Asp Ala Val Leu Asp Lys Asn Asn Ile Leu Gln Tyr
    1250                1255                1260

Tyr Ile Asn Glu Lys Glu Leu Leu Trp Lys Glu Ile Asp Ala Leu Lys
1265                1270                1275                1280

Ala Thr Phe Ala Ser Met Lys Asp Asn Ile Leu Asn Ala Asn Glu Ala
            1285                1290                1295

Val Ala Lys Tyr Ala Pro Ser Ile Ile Asp Ser Glu Lys Val Arg Ile
            1300                1305                1310

Gln Ser Val Ile Asp Asp Val Phe Glu Thr Leu Ser Ala Lys Ile Asn
            1315                1320                1325

Asn Asn Glu Asp Ser Ile Ser Asn Leu Glu Ser Ser Phe Ser Glu Tyr
            1330                1335                1340

Lys Ser Leu Ile Ser Asp Ala Ile Asp Gly Phe Lys Asp Glu Ile Ser
1345                1350                1355                1360

Ser Ile Arg Asn Ser Asn Asn Tyr Asp Asp Leu Ile Glu Glu Arg Asn
            1365                1370                1375

Arg Leu Glu Glu Ser Phe Asn Ser Leu Lys Asp Asp Phe Ser Lys Ile
            1380                1385                1390

Glu Asp Leu Glu Lys Asp Leu His Leu Val Lys Ala Lys Leu Lys Gly
            1395                1400                1405

Asp Asp Ser Ser Leu Ile Asp Glu Val Met Arg Leu Ser Asp Glu Leu
```

Glu Ile Leu Lys Asp Asn Val Ser Asn Met Asn Asn Thr Asp Asn Asn
1425                1430                1435                1440

Val Asn Asp Asn Asn Asp Ile Asp Ala Ile Tyr Glu Asp Phe Lys Gln
            1445                1450                1455

Leu Asn Glu Ser Leu Glu Ser Phe Lys Glu Thr Val Ile Pro Gln Leu
        1460                1465                1470

Ser Thr Phe Ser Lys Leu Glu Asp Lys Ile Ser Glu Asn Arg Glu Glu
            1475                1480                1485

Ile Tyr Lys Tyr Ile Asn Ser Ile Met Tyr Ser Leu Pro Glu Ala Tyr
    1490                1495                1500

Ile Ser Arg Glu Glu Ile Ser Asn Leu Glu Asn Lys Leu Tyr Asp Ile
1505                1510                1515                1520

Phe Asn Asn Phe Asn Asp Gly Ile Val Ser Ile Lys Asn Asp Leu Val
                1525                1530                1535

Phe Tyr Ile Glu Lys Asp Thr Lys Asp Phe Lys Asp Arg Ile Glu Lys
            1540                1545                1550

Lys Asn Arg Val Leu
        1555

<210> SEQ ID NO 7
<211> LENGTH: 2256
<212> TYPE: DNA
<213> ORGANISM: Brachyspira hyodysenteriae

<400> SEQUENCE: 7
atgaaaaata ctattttaaa aattttaat aaaagagttt taatatttac actttgtttt      60
gaaatcattg ttattgtaat gacatccatg ttgggtgctc aggatatatc attacaaaag    120
aatattatat caaaaaataa aatcaattat ggtacggcat tagaacttca atatagagga    180
aaatatttag aggcttataa tcaatttaca aatatcatga atacagaaga tgatatgatc    240
attagagatt tactatata ttacggagct aaaagtgctt tgctaactaa tatgtataat    300
gaagcaatag attatatgc cttactaatg aaagaatatc cgcgttcatc attatatcct    360
tatgcagagc aatataaggc tctttctgag ttttatagag atgattatcc tataagcaat    420
ttttttaatg gtaaatctca aaaatggatt aaagaatttg ttggaataag agctttaaga    480
gatactgatg ataccaataa ggctagaatg atagcttatg aacttttaaa cagattcgga    540
ttaagcgaag ctgctatata ttataataat aatttccctg aagatatttc atcttttcca    600
aataatttaa aatttaaaac agcaaccata ctttatgaag caggatatag aaaagcatct    660
ttaaagcatt ttcagtattt atatgataat aatgcttata agcaagttc tacatattat    720 atggctagaa ttaaacagaa gtctggagac agaagagatc ctgcggcttt attcgatgag    780
tatttatcaa atcttaacaa taaatctcat agaagattag gtctttacta ttctgcagat    840
aattataata gattaaaaaa ttatgaaaaa tcaatagaac tttataatac ttttttgaaa    900
gaatatccta gagatgatta tgttcctaga atatataata gttttgttac tttgagtttg    960
aatagaaata atttagttca ggcaaaaact tatcttacta atgtaatgaa gagatttcct   1020
aaaagcagat atacagagct tgcattaaaa tcatatttaa gaaaggcatt caattaaat    1080 aataaaacag aaacttattt tgctactaag gctttagaag caagatatcc tagtttcaga   1140
catgattttg cattatcttg gaatatgtgg actgctgaag agtttggaga tattgaaaaa   1200
agagatgaat atttaatgaa aacacttctt acaagtaaaa gccattattt tataaaaggt   1260

-continued

```
gctttgagtc ttgccaataa tgaaatgata gctaatgttc agcttagcaa tacttattat   1320
ttaaatgaag ctaaaagata ttatgctgat tctaatttta ctaaatctat gcagatgctt   1380
aataagatac aatttttaaa ttatattgct acaggtaaag aagataatat aacaagagag   1440
gctagggcat tggctaaaaa tattcttatg cataatagat ttgtaaaaga tttatacgct   1500
aatagaagcg aggatgattt atttaatgaa ttatcacttc agactagaag agaagttaat   1560
aaagcaataa tattatacta ttatggcgat tatgataatg catatactga attcgataaa   1620
atatttaaaa agacacaggt aacatatcct ttattttatt ttgctgaaaa aatatttaaa   1680
gattcaggaa atacaaaaag gcttatacaa gtatcagcaa atataggaaa atattttgga   1740
tatccttaca gtgataatgt tgatttgctt cctgatgagt ttagaaagag agtttatcct   1800
agatattttg atgaatatgt tgtacctgaa gctaaatatt ataaaataga gcctgctttt   1860
gtatatgcta taatgcgtga agaaagttta tttgatccta aagctaaatc ttgggttgga   1920
gctatgggac ttatgcagtt aatgcctaca acagcagcag ctgaaaataa aaaggcaaga   1980
tatagatata atcctttaga tttaacagat cctaagcaga atattaattt aggagtttct   2040
catttaggct ggttattcag cagtcaaaag gctagcaatt atatattagt agcagcaagt   2100
tataatgcag gttcaggacg cggaagaaga tggaaagcag agtatggtac taataatatg   2160
tatcgtacag gaagattcat tgatattgaa gaaactgaat attatgtaga gagagttatt   2220
aaaagctatg aatattacag caagtattat aaggac                              2256

<210> SEQ ID NO 8
<211> LENGTH: 752
<212> TYPE: PRT
<213> ORGANISM: Brachyspira hyodysenteriae

<400> SEQUENCE: 8

Met Lys Asn Thr Ile Leu Lys Ile Phe Asn Lys Arg Val Leu Ile Phe
 1               5                  10                  15

Thr Leu Cys Phe Glu Ile Ile Val Ile Val Met Thr Ser Met Leu Gly
            20                  25                  30

Ala Gln Asp Ile Ser Leu Gln Lys Asn Ile Ile Ser Lys Asn Lys Ile
        35                  40                  45

Asn Tyr Gly Thr Ala Leu Glu Leu His Asn Arg Gly Lys Tyr Leu Glu
    50                  55                  60

Ala Tyr Asn Gln Phe Thr Asn Ile Met Asn Thr Glu Asp Asp Met Ile
65                  70                  75                  80

Ile Arg Asp Tyr Thr Ile Tyr Tyr Gly Ala Lys Ser Ala Leu Leu Thr
                85                  90                  95

Asn Met Tyr Asn Glu Ala Ile Asp Leu Tyr Ala Leu Leu Met Lys Glu
            100                 105                 110

Tyr Pro Arg Ser Ser Leu Tyr Pro Tyr Ala Glu Gln Tyr Lys Ala Leu
        115                 120                 125

Ser Glu Phe Tyr Arg Asp Asp Tyr Pro Ile Ser Asn Phe Phe Asn Gly
    130                 135                 140

Lys Ser Gln Lys Trp Ile Lys Glu Phe Val Gly Ile Arg Ala Leu Arg
145                 150                 155                 160

Asp Thr Asp Asp Thr Asn Lys Ala Arg Met Ile Ala Tyr Glu Leu Leu
                165                 170                 175

Asn Arg Phe Gly Leu Ser Glu Ala Ala Ile Tyr Tyr Asn Asn Asn Phe
            180                 185                 190

Pro Glu Asp Ile Ser Ser Phe Pro Asn Asn Leu Lys Phe Lys Thr Ala
```

```
                195                 200                 205
Thr Ile Leu Tyr Glu Ala Gly Tyr Arg Lys Ala Ser Leu Lys His Phe
210                 215                 220
Gln Tyr Leu Tyr Asp Asn Asn Ala Tyr Lys Ala Ser Ser Thr Tyr Tyr
225                 230                 235                 240
Met Ala Arg Ile Lys Gln Lys Ser Gly Asp Arg Arg Asp Ala Ala Ala
                245                 250                 255
Leu Phe Asp Glu Tyr Leu Ser Asn Leu Asn Asn Lys Ser His Arg Arg
                260                 265                 270
Leu Gly Leu Tyr Tyr Ser Ala Asp Asn Tyr Asn Arg Leu Lys Asn Tyr
                275                 280                 285
Glu Lys Ser Ile Glu Leu Tyr Asn Thr Phe Leu Lys Glu Tyr Pro Arg
290                 295                 300
Asp Asp Tyr Val Pro Arg Ile Tyr Asn Ser Phe Val Thr Leu Ser Leu
305                 310                 315                 320
Asn Arg Asn Asn Leu Val Gln Ala Lys Thr Tyr Leu Thr Asn Val Met
                325                 330                 335
Lys Arg Phe Pro Lys Ser Arg Tyr Thr Glu Leu Ala Leu Lys Ser Tyr
                340                 345                 350
Leu Arg Lys Ala Phe Lys Leu Asn Asn Lys Thr Glu Thr Tyr Phe Ala
                355                 360                 365
Thr Lys Ala Leu Glu Ala Arg Tyr Pro Ser Phe Arg His Asp Phe Ala
370                 375                 380
Leu Ser Trp Asn Met Trp Thr Ala Glu Glu Phe Gly Asp Ile Glu Lys
385                 390                 395                 400
Arg Asp Glu Tyr Leu Met Lys Thr Leu Leu Thr Ser Lys Ser His Tyr
                405                 410                 415
Phe Ile Lys Gly Ala Leu Ser Leu Ala Asn Asn Glu Met Ile Ala Asn
                420                 425                 430
Val Gln Leu Ser Asn Thr Tyr Tyr Leu Asn Glu Ala Lys Arg Tyr Tyr
                435                 440                 445
Ala Asp Ser Asn Phe Thr Lys Ser Met Gln Met Leu Asn Lys Ile Gln
450                 455                 460
Phe Leu Asn Tyr Ile Ala Thr Gly Lys Glu Asp Asn Ile Thr Arg Glu
465                 470                 475                 480
Ala Arg Ala Leu Ala Lys Asn Ile Leu Met His Asn Arg Phe Val Lys
                485                 490                 495
Asp Leu Tyr Ala Asn Arg Ser Glu Asp Asp Leu Phe Asn Glu Leu Ser
                500                 505                 510
Leu Gln Thr Arg Arg Glu Val Asn Lys Ala Ile Ile Leu Tyr Tyr Tyr
                515                 520                 525
Gly Asp Tyr Asp Asn Ala Tyr Thr Glu Phe Asp Lys Ile Phe Lys Lys
                530                 535                 540
Thr Gln Val Thr Tyr Pro Leu Phe Tyr Phe Ala Glu Lys Ile Phe Lys
545                 550                 555                 560
Asp Ser Gly Asn Thr Lys Arg Leu Ile Gln Val Ser Ala Asn Ile Gly
                565                 570                 575
Lys Tyr Phe Gly Tyr Pro Tyr Ser Asp Asn Val Asp Leu Leu Pro Asp
                580                 585                 590
Glu Phe Arg Lys Arg Val Tyr Pro Arg Tyr Phe Asp Glu Tyr Val Val
                595                 600                 605
Pro Glu Ala Lys Tyr Tyr Lys Ile Glu Pro Ala Phe Val Tyr Ala Ile
610                 615                 620
```

Met Arg Glu Glu Ser Leu Phe Asp Pro Lys Ala Lys Ser Trp Val Gly
625                 630                 635                 640

Ala Met Gly Leu Met Gln Leu Met Pro Thr Thr Ala Ala Ala Glu Asn
            645                 650                 655

Lys Lys Ala Arg Tyr Arg Tyr Asn Pro Leu Asp Leu Thr Asp Pro Lys
        660                 665                 670

Gln Asn Ile Asn Leu Gly Val Ser His Leu Gly Trp Leu Phe Ser Ser
    675                 680                 685

Gln Lys Ala Ser Asn Tyr Ile Leu Val Ala Ala Ser Tyr Asn Ala Gly
690                 695                 700

Ser Gly Arg Gly Arg Arg Trp Lys Ala Glu Tyr Gly Thr Asn Asn Met
705                 710                 715                 720

Tyr Arg Thr Gly Arg Phe Ile Asp Ile Glu Glu Thr Glu Tyr Tyr Val
                725                 730                 735

Glu Arg Val Ile Lys Ser Tyr Glu Tyr Tyr Ser Lys Tyr Tyr Lys Asp
            740                 745                 750

<210> SEQ ID NO 9
<211> LENGTH: 723
<212> TYPE: DNA
<213> ORGANISM: Brachyspira hyodysenteriae

<400> SEQUENCE: 9
atggaaacta gattgcttta caactttgaa acattagacg aatggcaacc aatatcaaat      60
gccagccgct ttatgtttag aggtgataga caaatgaaa atggtgttgt aatgaaatat     120
cctaatatga gattgttcgc tacaaaacca tatggtatgg gtaaccaaag ttataattca     180
actaattcat tatcagtaag tgtttctttt tcagaaaat cttataactt ctttgattta     240
gttccaacag tacaaaaaat cataccaggt aaagctcaaa cttttgatgt tgggtatgg      300 ggtggtaatt atgactatac tatggaaatg atatttgaag attatcgtgg ttatacttat     360
acattacctt taggatctat aagatatata ggttggagaa atatgagtac agcagtgcca     420
tctttcattc ctcaagaaga gccttatgtt cctagagcta aggtttaag atttatgaat      480 ttccgttct ggtcatcacc agaggaaaga gcagataact ttgtagtttt attggattac      540
ttccaaacag taacagatac attcagagaa gcttatgacg gatctgatat tgaaactaca     600
ttaggtcagg aagttggcgg aagatcttct gaacaatata cagaaggcgg agctaaagta     660
gtaggtgaag acggcggtaa cgctggagct gctactacag aacagccaca agaagcgcaa     720
caa                                                                   723

<210> SEQ ID NO 10
<211> LENGTH: 241
<212> TYPE: PRT
<213> ORGANISM: Brachyspira hyodysenteriae

<400> SEQUENCE: 10

Met Glu Thr Arg Leu Leu Tyr Asn Phe Glu Thr Leu Asp Glu Trp Gln
1               5                   10                  15

Pro Ile Ser Asn Ala Ser Arg Phe Met Phe Arg Gly Asp Arg Thr Asn
            20                  25                  30

Glu Asn Gly Val Val Met Lys Tyr Pro Asn Met Arg Leu Phe Ala Thr
        35                  40                  45

Lys Pro Tyr Gly Met Gly Asn Gln Ser Tyr Asn Ser Thr Asn Ser Leu
    50                  55                  60

-continued

Ser Val Ser Val Ser Phe Phe Arg Lys Ser Tyr Asn Phe Phe Asp Leu
65 70 75 80

Val Pro Thr Val Gln Lys Ile Ile Pro Gly Lys Ala Gln Thr Phe Asp
85 90 95

Val Trp Val Trp Gly Gly Asn Tyr Asp Tyr Thr Met Glu Met Ile Phe
100 105 110

Glu Asp Tyr Arg Gly Tyr Thr Tyr Thr Leu Pro Leu Gly Ser Ile Arg
115 120 125

Tyr Ile Gly Trp Arg Asn Met Ser Thr Ala Val Pro Ser Phe Ile Pro
130 135 140

Gln Glu Glu Pro Tyr Val Pro Arg Ala Lys Gly Leu Arg Phe Met Asn
145 150 155 160

Phe Arg Phe Trp Ser Ser Pro Glu Glu Arg Ala Asp Asn Phe Val Val
165 170 175

Leu Leu Asp Tyr Phe Gln Thr Val Thr Asp Thr Phe Arg Glu Ala Tyr
180 185 190

Asp Gly Ser Asp Ile Glu Thr Thr Leu Gly Gln Glu Val Gly Gly Arg
195 200 205

Ser Ser Glu Gln Tyr Thr Glu Gly Gly Ala Lys Val Val Gly Glu Asp
210 215 220

Gly Gly Asn Ala Gly Ala Ala Thr Thr Glu Gln Pro Gln Glu Ala Gln
225 230 235 240

Gln

<210> SEQ ID NO 11
<211> LENGTH: 3129
<212> TYPE: DNA
<213> ORGANISM: Brachyspira hyodysenteriae

<400> SEQUENCE: 11
atgattgaag aagaaagaag acaggttgct gaaatgtttg aaagcataca aaatgattct 60
atagatactg atttgagata tcttacagat tcattcagag atgatatcat aaaagtattt 120
gaagaatcta atgatgagtt cagaaaacgt gtagaagcta gaatagttca ttttgaagat 180
gcttatgctt cacctgatag aataaaagaa ttctataaag atgctatact ttctgaagtg 240
gacagcttga gaagtgatgc agaacagata cttatagatt taaatgataa ggtagaaaat 300
gcaaaagaac agatagaagt attagaaaat gatagagtaa aagacataat caataaaata 360
gatgaagcag aaaatgatat taattcttta ataaatacta taaaagctaa tattaaagaa 420
caagaaaatg agcttagaat gttgagccaa tctcagaaac atatatctca ggaagtagag 480
actgttcgca gagagagaga agctcttatg gatatggtta aaaactctga tataaatata 540
agaaacaagc ttgacagttt aacaagtgct gtatcagaag ctgcagagat tgcttcatct 600
aagatagctg aaaaagaagc agcattcagc agtaaagtta aagaagctga agaatatatt 660
aattcattgt ctgatagaat tacattagaa aataacagtg ctttagataa agctagagaa 720
gatattaata atttagttgc ttctttcaat gaatcagtta taaaagagac taatgatttg 780
gcacctcata taactaatac agttcagaat ttcattaata atgaaatgaa aaaatttgat 840
aaattctcag atgttagaag tgctatagaa ggcattgaga atgatattaa taacaagata 900
actgaagcat tcaataatat gaacaaagaa cttgaagata atattgttga atttagaaag 960
aaaatagata catatcagga agagtttatc agtgaattaa agatgtctgt aaatgtagag 1020
ggtgaaaaag ctgttgatga aattaagtct ttacataatg atgaagttgc taaattaaaa 1080

```
gagatgtatt taactactga aaaattctat acagatagac aagagaaaaa ccatgaagac    1140
ttctcaaaat tatttgaaga aacttataaa gactataatg aaaaaataga atcattatat    1200
gctcaattag atgatactaa acttcaaata agtacttctg ttgaagatgt tgttgctgat    1260
ttgaagcagg ctttaagcat aaaagatgag ttcttaactt cagttgaaaa taataaagaa    1320
aaacttgaag ctgttgaaga gcaaatgaat aatttacaga atgaatttgc tccttcagta    1380
gaaaaattga agacataat agaagaaaag gcattagaat acaagagaa atcaatgaa      1440 tactctcaag atatagaact tcaaggagat aagttcaatt ctagattgga gagttatct    1500 aataatgcta atctactat agaagataag gtaactgaat ttgattctat aatagaaaat    1560
atttctaata aaatggatac tttattagaa gaaaagaatt cagagttcga tgcattaaaa    1620
gcacattatg aaggactttc agaatcattg acagcattga agatactat atcagaagca    1680 gttaatgaaa aatagaaga agcaaatagc attatagagg aaaatgttca gactatagaa    1740
gaatcagcta tgaaaaata tgaaaaatac atagcaagac ttaattctaa tttagaacaa    1800
acattgtctc ttttaatgaa cgatgctaaa gaacatatac agaaagctaa agtgaaata    1860 attaaagctc atactgataa tttagatgag tatgatcaga gaattacaaa tatgaaagat    1920
attgtttcag ctttagaaga agatataact aaatattctt ctgagataga tgcaagactt    1980
gaaagtatta atttaagcta tgatgaaaaa acaaatgtta tacttaaaga tttttgaaaat   2040 agaactgatg atttgaaatt gaattaaat gatgcatctg aatctattga caaaatgctt    2100
gatttaaaaa ctaatgatat ttcttagag tatgaggcta tgaaatcaaa aatagatgat    2160
atagctaaag atatagaaaa atacatgaat actgttaaag tatttgataa tgctaaagaa    2220
atggcagatt ctataagaga tgacgtttct aagttgaatg ctttggttga ggatactaaa    2280
gctacaacaa ttgaaatgaa taagactatg tccgaatttg atagcttaaa gaaaatgcat    2340
caggaaatat taggatatgc agaaagtctt aaaaaggaaa aagacagctt gaaagatact    2400
caggaaaaag taaatatgtt aatggaaatg tctggtgaaa ttcaagagag attcgttaat    2460
atagcagaaa ataatgctat gatagagcat gctgaggaag gaatacaggt tgttatagat    2520
atagcatctc aaatagaaaa taaactttca ttcattaagg ataaggaaga gtatgcagat    2580
gatatattac agcaaataag aaaagctgaa gtagaaaccg aaactatttt agaaagagta    2640
gatagtataa aagaagctat ggttgaagtt gaagatacta gaaagaactt tatggataag    2700
atttattctt tagaaagaga tatggctaaa atagataaga atgataaaaa agttcagttg    2760
tttatttcta aattgaaga gataaatgat ataatagatg ccatacagga tcaaagagaa    2820
aatcttgttc gtatgaagaa tcagtatgat gattatgata agaacatagt taagaatttg    2880
gaaagagctg aatattttgt aagatattta gagactttac tagataatgc tgataaatat    2940
atgtctgata aaggttctaa gacttctaaa aaaggaacag ctgctaaat agatagtaag    3000 aaagaagagt ttataattag aatgtataaa gaaggttgga aaccagatga gatagttaaa    3060
aatagttcat attcaagaga tgaagttgaa agaactataa aagcatggaa agataagcaa    3120
tccagagga                                                           3129
```

<210> SEQ ID NO 12
<211> LENGTH: 1043
<212> TYPE: PRT
<213> ORGANISM: Brachyspira hyodysenteriae

<400> SEQUENCE: 12

Met Ile Glu Glu Glu Arg Arg Gln Val Ala Glu Met Phe Glu Ser Ile

```
            1               5               10              15
        Gln Asn Asp Ser Ile Asp Thr Asp Leu Arg Tyr Leu Thr Asp Ser Phe
                        20              25              30
        Arg Asp Asp Ile Ile Lys Val Phe Glu Glu Ser Asn Asp Glu Phe Arg
                    35              40              45
        Lys Arg Val Glu Ala Arg Ile Val His Phe Glu Asp Ala Tyr Ala Ser
                50              55              60
        Pro Asp Arg Ile Lys Glu Phe Tyr Lys Asp Ala Ile Leu Ser Glu Val
        65              70              75              80
        Asp Ser Leu Arg Ser Asp Ala Glu Gln Ile Leu Ile Asp Leu Asn Asp
                        85              90              95
        Lys Val Glu Asn Ala Lys Glu Gln Ile Glu Val Leu Glu Asn Asp Arg
                    100             105             110
        Val Lys Asp Ile Ile Asn Lys Ile Asp Glu Ala Glu Asn Asp Ile Asn
                115             120             125
        Ser Leu Ile Asn Thr Ile Lys Ala Asn Ile Lys Glu Gln Glu Asn Glu
            130             135             140
        Leu Arg Met Leu Ser Gln Ser Gln Lys His Ile Ser Gln Glu Val Glu
        145             150             155             160
        Thr Val Arg Arg Glu Arg Ala Leu Met Asp Met Val Lys Asn Ser
                        165             170             175
        Asp Ile Asn Ile Arg Asn Lys Leu Asp Ser Leu Thr Ser Ala Val Ser
                    180             185             190
        Glu Ala Ala Glu Ile Ala Ser Ser Lys Ile Ala Glu Lys Glu Ala Ala
                195             200             205
        Phe Ser Ser Lys Val Lys Glu Ala Glu Glu Tyr Ile Asn Ser Leu Ser
        210             215             220
        Asp Arg Ile Thr Leu Glu Asn Asn Ser Ala Leu Asp Lys Ala Arg Glu
        225             230             235             240
        Asp Ile Asn Asn Leu Val Ala Ser Phe Asn Glu Ser Val Ile Lys Glu
                        245             250             255
        Thr Asn Asp Leu Ala Pro His Ile Thr Asn Thr Val Gln Asn Phe Ile
                    260             265             270
        Asn Asn Glu Met Lys Lys Phe Asp Lys Phe Ser Asp Val Arg Ser Ala
                275             280             285
        Ile Glu Gly Ile Glu Asn Asp Ile Asn Asn Lys Ile Thr Glu Ala Phe
            290             295             300
        Asn Asn Met Asn Lys Glu Leu Glu Asp Asn Ile Val Glu Phe Arg Lys
        305             310             315             320
        Lys Ile Asp Thr Tyr Gln Glu Glu Phe Ile Ser Glu Leu Lys Met Ser
                        325             330             335
        Val Asn Val Glu Gly Glu Lys Ala Asp Glu Ile Lys Ser Leu His
                    340             345             350
        Asn Asp Glu Val Ala Lys Leu Lys Glu Met Tyr Leu Thr Thr Glu Lys
                355             360             365
        Phe Tyr Thr Asp Arg Gln Glu Lys Asn His Glu Asp Phe Ser Lys Leu
            370             375             380
        Phe Glu Glu Thr Tyr Lys Asp Tyr Asn Glu Lys Ile Glu Ser Leu Tyr
        385             390             395             400
        Ala Gln Leu Asp Asp Thr Lys Leu Gln Ile Ser Thr Ser Val Glu Asp
                        405             410             415
        Val Val Ala Asp Leu Lys Gln Ala Leu Ser Ile Lys Asp Glu Phe Leu
                    420             425             430
```

```
Thr Ser Val Glu Asn Asn Lys Glu Lys Leu Glu Ala Val Glu Glu Gln
        435                 440                 445

Met Asn Asn Leu Gln Asn Glu Phe Ala Pro Ser Val Glu Lys Leu Lys
        450                 455                 460

Asp Ile Glu Glu Lys Ala Leu Glu Leu Gln Glu Lys Ile Asn Glu
465                 470                 475                 480

Tyr Ser Gln Asp Ile Glu Leu Gln Gly Asp Lys Phe Asn Ser Arg Leu
                485                 490                 495

Glu Glu Leu Ser Asn Asn Ala Lys Ser Thr Ile Glu Asp Lys Val Thr
            500                 505                 510

Glu Phe Asp Ser Ile Ile Glu Asn Ile Ser Asn Lys Met Asp Thr Leu
        515                 520                 525

Leu Glu Glu Lys Asn Ser Glu Phe Asp Ala Leu Lys Ala His Tyr Glu
        530                 535                 540

Gly Leu Ser Glu Ser Leu Thr Ala Leu Lys Asp Thr Ile Ser Glu Ala
545                 550                 555                 560

Val Asn Glu Arg Ile Glu Ala Asn Ser Ile Glu Glu Asn Val
                565                 570                 575

Gln Thr Ile Glu Glu Ser Ala Asn Glu Lys Tyr Glu Lys Tyr Ile Ala
        580                 585                 590

Arg Leu Asn Ser Asn Leu Glu Gln Thr Leu Ser Leu Leu Met Asn Asp
        595                 600                 605

Ala Lys Glu His Ile Gln Lys Ala Lys Asp Glu Ile Ile Lys Ala His
        610                 615                 620

Thr Asp Asn Leu Asp Glu Tyr Asp Gln Arg Ile Thr Asn Met Lys Asp
625                 630                 635                 640

Ile Val Ser Ala Leu Glu Glu Asp Ile Thr Lys Tyr Ser Ser Glu Ile
                645                 650                 655

Asp Ala Arg Leu Glu Ser Ile Asn Leu Ser Tyr Asp Glu Lys Thr Asn
            660                 665                 670

Val Ile Leu Lys Asp Phe Glu Asn Arg Thr Asp Asp Leu Lys Leu Lys
        675                 680                 685

Leu Asn Asp Ala Ser Glu Ser Ile Asp Lys Met Leu Asp Leu Lys Thr
        690                 695                 700

Asn Asp Ile Ser Leu Glu Tyr Glu Ala Met Lys Ser Lys Ile Asp Asp
705                 710                 715                 720

Ile Ala Lys Asp Ile Glu Lys Tyr Met Asn Thr Val Lys Val Phe Asp
                725                 730                 735

Asn Ala Lys Glu Met Ala Asp Ser Ile Arg Asp Val Ser Lys Leu
            740                 745                 750

Asn Ala Leu Val Glu Asp Thr Lys Ala Thr Thr Ile Glu Met Asn Lys
        755                 760                 765

Thr Met Ser Glu Phe Asp Ser Leu Lys Lys Met His Gln Glu Ile Leu
        770                 775                 780

Gly Tyr Ala Glu Ser Leu Lys Lys Glu Lys Asp Ser Leu Lys Asp Thr
785                 790                 795                 800

Gln Glu Lys Val Asn Met Leu Met Glu Met Ser Gly Glu Ile Gln Glu
                805                 810                 815

Arg Phe Val Asn Ile Ala Glu Asn Asn Ala Met Ile Glu His Ala Glu
            820                 825                 830

Glu Gly Ile Gln Val Val Ile Asp Ile Ala Ser Gln Ile Glu Asn Lys
        835                 840                 845
```

```
Leu Ser Phe Ile Lys Asp Lys Glu Glu Tyr Ala Asp Asp Ile Leu Gln
        850                 855                 860

Gln Ile Arg Lys Ala Glu Val Glu Thr Glu Thr Ile Leu Glu Arg Val
865                 870                 875                 880

Asp Ser Ile Lys Glu Ala Met Val Glu Val Glu Asp Thr Arg Lys Asn
                885                 890                 895

Phe Met Asp Lys Ile Tyr Ser Leu Glu Arg Asp Met Ala Lys Ile Asp
                900                 905                 910

Lys Asn Asp Lys Lys Val Gln Leu Phe Ile Ser Lys Leu Glu Glu Ile
            915                 920                 925

Asn Asp Ile Ile Asp Ala Ile Gln Asp Gln Arg Glu Asn Leu Val Arg
        930                 935                 940

Met Lys Asn Gln Tyr Asp Asp Tyr Asp Lys Asn Ile Val Lys Asn Leu
945                 950                 955                 960

Glu Arg Ala Glu Tyr Phe Val Arg Tyr Leu Glu Thr Leu Leu Asp Asn
                965                 970                 975

Ala Asp Lys Tyr Met Ser Asp Lys Gly Ser Lys Thr Ser Lys Lys Gly
            980                 985                 990

Thr Ala Ala Lys Ile Asp Ser Lys Lys Glu Glu Phe Ile Ile Arg Met
        995                 1000                1005

Tyr Lys Glu Gly Trp Lys Pro Asp Glu Ile Val Lys Asn Ser Ser Tyr
    1010                1015                1020

Ser Arg Asp Glu Val Glu Arg Thr Ile Lys Ala Trp Lys Asp Lys Gln
1025                1030                1035                1040

Ser Arg Gly

<210> SEQ ID NO 13
<211> LENGTH: 729
<212> TYPE: DNA
<213> ORGANISM: Brachyspira hyodysenteriae

<400> SEQUENCE: 13
atgataaaaa aaattttaac tttaatcttt gtattaattt tggcagcttc atgttctact    60
aatgataaac atgttgtagt attagctttt agtaaacagc ttcatgctgt actttataat   120
gataatagtc agtctacaaa aacagcatca aaaacatata tacaaaaaga tgatattaca   180
actgtagcag atcctataaa agaaaaaaaa gaatatacaa atactcaagc acaagtaagt   240
aaaaaagcag aagaaaaaaa agaagaactt acaaataacg atgctttaga agaagaaaaa   300
cctcaagtta taaagcaaac tgaggttata cagaaagatg ataatgagat tcttcttact   360
gcaaatataa tatcttttga ttttgattct tatgaattaa aaaatgaata taatgaaggg   420
atagatgaaa tttgcaaata tttaaataat aatcgagata ttaatctaat aatagaagga   480
catagcgaca gtataggga ctcaaattat aatatatatt tatctgaaaa cagagcaaaa   540
gcgatatttg ataaattagt agataaagga atagataaag atagacttag atatataggga   600 tatggctcta ctcattcatc tgagtataat gataaagaca gaaaatgcca atttgttata   660
ataaataatt cagatgaaga gcaggaatac aaaaaagaaa acgaaactga tattatcaaa   720
ttaaaacaa                                                          729

<210> SEQ ID NO 14
<211> LENGTH: 243
<212> TYPE: PRT
<213> ORGANISM: Brachyspira hyodysenteriae

<400> SEQUENCE: 14
```

Met Ile Lys Lys Ile Leu Thr Leu Ile Phe Val Leu Ile Leu Ala Ala
1               5                   10                  15

Ser Cys Ser Thr Asn Asp Lys His Val Val Leu Ala Phe Ser Lys
            20                  25                  30

Gln Leu His Ala Val Leu Tyr Asn Asp Asn Ser Gln Ser Thr Lys Thr
            35                  40                  45

Ala Ser Lys Thr Tyr Ile Gln Lys Asp Asp Ile Thr Thr Val Ala Asp
            50                  55                  60

Pro Ile Lys Glu Lys Lys Glu Tyr Thr Asn Thr Gln Ala Gln Val Ser
65                  70                  75                  80

Lys Lys Ala Glu Glu Lys Lys Glu Glu Leu Thr Asn Asn Asp Ala Leu
                85                  90                  95

Glu Glu Glu Lys Pro Gln Val Ile Lys Gln Thr Glu Val Ile Gln Lys
            100                 105                 110

Asp Asp Asn Glu Ile Leu Leu Thr Ala Asn Ile Ile Ser Phe Asp Phe
            115                 120                 125

Asp Ser Tyr Glu Leu Lys Asn Glu Tyr Asn Glu Gly Ile Asp Glu Ile
            130                 135                 140

Cys Lys Tyr Leu Asn Asn Asn Arg Asp Ile Asn Leu Ile Ile Glu Gly
145                 150                 155                 160

His Ser Asp Ser Ile Gly Asp Ser Asn Tyr Asn Ile Tyr Leu Ser Glu
                165                 170                 175

Asn Arg Ala Lys Ala Ile Phe Asp Lys Leu Val Asp Lys Gly Ile Asp
            180                 185                 190

Lys Asp Arg Leu Arg Tyr Ile Gly Tyr Gly Ser Thr His Ser Ser Glu
            195                 200                 205

Tyr Asn Asp Lys Asp Arg Lys Cys Gln Phe Val Ile Ile Asn Asn Ser
            210                 215                 220

Asp Glu Glu Gln Glu Tyr Lys Lys Glu Asn Gly Thr Asp Ile Ile Lys
225                 230                 235                 240

Leu Lys Gln

<210> SEQ ID NO 15
<211> LENGTH: 2475
<212> TYPE: DNA
<213> ORGANISM: Brachyspira hyodysenteriae

<400> SEQUENCE: 15
atgaaattga ataataaagt tttatataaa ttcccaatat taatactgtt tataatatta      60
ttatcatgtt ctaatagtca ggaagaaata gagcaaaaag aaatagacag aggcggagca     120
ttaatagata aaataatata tgaagtaaga acagatatga caatagctat aaagatgtg      180 gcagacggca gagcagattt aatggcaagc ggaatagacg gaagtacata tttatcatta     240
ggcgaaagtg atttagagaa acttgatact tatgcagtac cttcaggttc atggtcatta     300
ttgtttaatc ccgtaccaaa taagctccca tacacagtta aacaagaga cggaaaaact     360 cattttaatc ctctagctat aaaagaagta agatttgcta tgaacttctt aattgataga     420
aaaaagcttg ttgatgaaat tttaagaggg gcaggacagc cttcatttac acaagcaaca     480
ccggggcagc cgggtactta tagatataat cttataccct caaaaatggg tatgacagaa     540
aacggtaatc aggaaaaagc tcttaatgat ataaataaag ctatggaaaa agctgctaat     600
ttaccagaga atagaggaaa attagtaaaa gaaaatggat ggtggaaata taatggaaaa     660
gtagtaacta ttaaatttgt tataagagtt gatgatccta caggaagact tccagctggt     720

```
aatgcaatat ctgatttaat agaaaaaaca ggaataaaag ttgagaaatt attgtatgac    780
agaaataaat ctactcaagt tgtatacggt tcagacccaa aagattatga atggaatatt    840
ataacagagg cttggggagc aggtgctact cgtgcttggt gggatgttac attaagacag    900
atgtatgtaa gggaaggcaa ttatatgcct ggtgctaatg tatctgagtt ttggaattat    960
gataataaag aagcttcaag aataagcgac aagaattcaa atggctggtt tttgactgcc   1020
gatgaatatt ggaatggtaa tatgcgtttg caggagattg gacttgaaga tgctgtcaga   1080
atatatttaa attctcagac tcagtttttt gtagcgaata agaaagatt caatagaaga   1140
atgctttacg gagtaggtga cggggttaat gattggtcta taagaagtgc tgatataaaa   1200
ccaaatagaa atggtgaaaa agtattaaga gttcttcagc attctgccca aggttcatta   1260
tttataagtc cttgggatcc tgtaggagta ggaggatttt ctgatgccta ttctgctata   1320
atgataggac cttgttctga tgcaggtgct acatttgaat cgccttccac tgctaagaca   1380
gaattcatac ttggtgaagc tgacaccaac agtttagaaa taggagtgag agcaggaaat   1440
aatggaatac ctgttggtac tgttaatgtt cctcaaaatg caataatgta taatccttat   1500
actcagaaat gggaagaggg tttaacagtt aaagttaatg ataaaggcga attagtttac   1560
acaaaatcgg ataatcttac tgcttatgtg aaatgtgatt ttaagcctag aagttttaaa   1620
tggcatcatg gcatagattc atctttggtt gatttgatgt atggaagcgt attcattgct   1680
aatataataa caaagactaa tgaaaacgat aaatatatg attctgctat ggctggaaga   1740
tatctttctg ctatggacgg agctgtagga agcattataa atgaggacgg aagttttact   1800
ttatacggaa attattattg gcctatggat atggacagac aaattgctgt tgctgctgta   1860
agtcctaaaa taggcaatcc taatagaaat actgttattc ctttcgagat aaatgaagct   1920
ataatgaaaa ttgttcttga aggctctaaa tctggaaatg tttatactat ttcacaggat   1980
cagtctttaa cttccataga tgttaaaaat cctacatgtg tatcagatat aaaagaaaaa   2040
ttaatagaaa tgcgtgattc tcagtatata cctgctggaa tagaagattt tataactaaa   2100
gaagatgcag taaagagata tcaagctgcc attgatttta tagataaata cggacatgct   2160
tatatatcaa atggtccttt ctttatttca agaaatagatt caaaggcaaa ttatatagaa   2220
ttaacagctt ttaaagatta tagctatact gctgattatt ggatagatag attatctacc   2280
aaaatgagca aatagaaga tattgatatg cctgctatag caaacagaaa caatgatatg   2340
aatatagata tttatgtttc ttcatataat tatcctgaca atgcattaga aatgccagat   2400
cctaatacaa cagtaaaagt attacttcaa ttacaaatgg agggcgaaaa agaatataat   2460
gcagttttta gaaaa                                                    2475
```

<210> SEQ ID NO 16
<211> LENGTH: 825
<212> TYPE: PRT
<213> ORGANISM: Brachyspira hyodysenteriae

<400> SEQUENCE: 16

Met Lys Leu Asn Asn Lys Val Leu Tyr Lys Phe Pro Ile Leu Ile Leu
 1               5                  10                  15

Phe Ile Ile Leu Leu Ser Cys Ser Asn Ser Gln Glu Glu Ile Glu Gln
            20                  25                  30

Lys Glu Ile Asp Arg Gly Gly Ala Leu Ile Asp Lys Ile Ile Tyr Glu
        35                  40                  45

Val Arg Thr Asp Met Thr Ile Ala Ile Lys Asp Val Ala Asp Gly Arg

-continued

```
                50                  55                  60
Ala Asp Leu Met Ala Ser Gly Ile Asp Gly Ser Thr Tyr Leu Ser Leu
 65                  70                  75                  80

Gly Glu Ser Asp Leu Glu Lys Leu Asp Thr Tyr Ala Val Pro Ser Gly
                 85                  90                  95

Ser Trp Ser Leu Leu Phe Asn Pro Val Pro Asn Lys Ala Pro Tyr Thr
                100                 105                 110

Val Thr Thr Arg Asp Gly Lys Thr His Phe Asn Pro Leu Ala Ile Lys
                115                 120                 125

Glu Val Arg Phe Ala Met Asn Phe Leu Ile Asp Arg Lys Lys Leu Val
                130                 135                 140

Asp Glu Ile Leu Arg Gly Ala Gly Gln Pro Ser Phe Thr Gln Ala Thr
145                 150                 155                 160

Pro Gly Gln Pro Gly Thr Tyr Arg Tyr Asn Leu Ile Pro Ser Lys Met
                165                 170                 175

Gly Met Thr Glu Asn Gly Asn Gln Glu Lys Ala Leu Asn Asp Ile Asn
                180                 185                 190

Lys Ala Met Glu Lys Ala Ala Asn Leu Pro Glu Asn Arg Gly Lys Leu
                195                 200                 205

Val Lys Glu Asn Gly Trp Trp Lys Tyr Asn Gly Glu Val Val Thr Ile
210                 215                 220

Lys Phe Val Ile Arg Val Asp Asp Pro Thr Gly Arg Leu Pro Ala Gly
225                 230                 235                 240

Asn Ala Ile Ser Asp Leu Ile Glu Lys Thr Gly Ile Lys Val Glu Lys
                245                 250                 255

Leu Leu Tyr Asp Arg Asn Lys Ser Thr Gln Val Val Tyr Gly Ser Asp
                260                 265                 270

Pro Lys Asp Tyr Glu Trp Asn Ile Ile Thr Glu Ala Trp Gly Ala Gly
                275                 280                 285

Ala Thr Arg Ala Trp Trp Asp Val Thr Leu Arg Gln Met Tyr Val Arg
290                 295                 300

Glu Gly Asn Tyr Met Pro Gly Ala Asn Val Ser Glu Phe Trp Asn Tyr
305                 310                 315                 320

Asp Asn Lys Glu Ala Ser Arg Ile Ser Asp Lys Asn Ser Asn Gly Trp
                325                 330                 335

Phe Leu Thr Ala Asp Glu Tyr Trp Asn Gly Asn Met Arg Leu Gln Glu
                340                 345                 350

Ile Gly Leu Glu Asp Ala Val Arg Ile Tyr Leu Asn Ser Gln Thr Gln
                355                 360                 365

Phe Phe Val Ala Asn Lys Glu Arg Phe Asn Arg Arg Met Leu Tyr Gly
                370                 375                 380

Val Gly Asp Gly Val Asn Asp Trp Ser Ile Arg Ser Ala Asp Ile Lys
385                 390                 395                 400

Pro Asn Arg Asn Gly Glu Lys Val Leu Arg Val Leu Gln His Ser Ala
                405                 410                 415

Gln Gly Ser Leu Phe Ile Ser Pro Trp Asp Pro Val Gly Val Gly Gly
                420                 425                 430

Phe Ser Asp Ala Tyr Ser Ala Ile Met Ile Gly Pro Cys Ser Asp Ala
                435                 440                 445

Gly Ala Thr Phe Glu Ser Pro Ser Thr Ala Lys Thr Glu Phe Ile Leu
                450                 455                 460

Gly Glu Ala Asp Thr Asn Ser Leu Glu Ile Gly Val Arg Ala Gly Asn
465                 470                 475                 480
```

Asn Gly Ile Pro Val Gly Thr Val Asn Val Pro Gln Asn Ala Ile Met
                485                 490                 495

Tyr Asn Pro Tyr Thr Gln Lys Trp Glu Gly Leu Thr Val Lys Val
            500                 505                 510

Asn Asp Lys Gly Glu Leu Val Tyr Thr Lys Ser Asp Asn Leu Thr Ala
        515                 520                 525

Tyr Val Lys Cys Asp Phe Lys Pro Arg Ser Phe Lys Trp His His Gly
    530                 535                 540

Ile Asp Ser Ser Leu Val Asp Leu Met Tyr Gly Ser Val Phe Ile Ala
545                 550                 555                 560

Asn Ile Ile Thr Lys Thr Asn Glu Asn Asp Lys Tyr Tyr Asp Ser Ala
                565                 570                 575

Met Ala Gly Arg Tyr Leu Ser Ala Met Asp Gly Ala Val Gly Ser Ile
            580                 585                 590

Ile Asn Glu Asp Gly Ser Phe Thr Leu Tyr Gly Asn Tyr Tyr Trp Pro
        595                 600                 605

Met Asp Met Asp Arg Gln Ile Ala Val Ala Ala Val Ser Pro Lys Ile
    610                 615                 620

Gly Asn Pro Asn Arg Asn Thr Val Ile Pro Phe Glu Ile Asn Glu Ala
625                 630                 635                 640

Ile Met Lys Ile Val Leu Glu Gly Ser Lys Ser Gly Asn Val Tyr Thr
                645                 650                 655

Ile Ser Gln Asp Gln Ser Leu Thr Ser Ile Asp Val Lys Asn Pro Thr
            660                 665                 670

Cys Val Ser Asp Ile Lys Glu Lys Leu Ile Glu Met Arg Asp Ser Gln
        675                 680                 685

Tyr Ile Pro Ala Gly Ile Glu Asp Phe Ile Thr Lys Glu Asp Ala Val
    690                 695                 700

Lys Arg Tyr Gln Ala Ala Ile Asp Phe Ile Asp Lys Tyr Gly His Ala
705                 710                 715                 720

Tyr Ile Ser Asn Gly Pro Phe Phe Ile Ser Arg Ile Asp Ser Lys Ala
                725                 730                 735

Asn Tyr Ile Glu Leu Thr Ala Phe Lys Asp Tyr Ser Tyr Thr Ala Asp
            740                 745                 750

Tyr Trp Ile Asp Arg Leu Ser Thr Lys Met Ser Arg Ile Glu Asp Ile
        755                 760                 765

Asp Met Pro Ala Ile Ala Asn Arg Asn Asn Asp Met Asn Ile Asp Ile
    770                 775                 780

Tyr Val Ser Ser Tyr Asn Tyr Pro Asp Asn Ala Leu Glu Met Pro Asp
785                 790                 795                 800

Pro Asn Thr Thr Val Lys Val Leu Leu Gln Leu Gln Met Glu Gly Glu
                805                 810                 815

Lys Glu Tyr Asn Ala Val Phe Arg Lys
            820                 825

<210> SEQ ID NO 17
<211> LENGTH: 1014
<212> TYPE: DNA
<213> ORGANISM: Brachyspira hyodysenteriae

<400> SEQUENCE: 17
gtggtctgca atatgaataa gaagaacatt atattattat tatctattat tatgatgctg      60
attgtatcat gtgaggaaaa aacagaaagt actgtgacaa tacaaaaata tccaataaga     120

```
gttggatata tgccagattt ttctggaagt tctgctgttg ctatagcaaa agaaagggt     180 tattttgatg aagaaaattt agatgttaca ttggttgagt ttttagatgg tccttctgaa    240
gtagaggaga tgcttttaaa aaatttagaa tttgcttata taggacatgg tgcacatgct    300
ttagctattg aaggtaaagt taatgtatta tttcctaatg gtttaagcag atctgaacaa    360
attatagtaa gaaatgcttc tcaaatagaa tctattaaag atttaagagg taaaaaagtt    420
ggaacacaat taggaacttc ttcagaaatt ttactttatt tggctcttca gtcattaggt    480
attaaagcag aagaagtaga tattataaat atggatggaa atactatagt atcatctata    540
gctgatggta ctattgatgc tgcttcagtg caagctccat atactttga aatattaaat      600 aatactgaaa acaatgtaaa gtctatagct acaactgttg attattctga tgtaggttct    660
tttcctagca gctggatagt tacaccttct tatcaaagta ataatacaga tatagttaat    720
agattttcaa gagctatact taaagctatg gactatagac aacttaatat gagtgaagct    780
gtgcaattgg ttgctaacat gaatagtaaa acagttgaag aagttgattt agaaagagaa    840
acaggagtat ggttttctgg taatgagata aagcaagcat atattaatgg tgatgctggt    900
aaatggtata aaacacagca gaatatattt atttatacta aaactattac aaataatatt    960
gatattaata attatgtgca gttaaaatac atggttgata atgtatttaa tgaa          1014
```

<210> SEQ ID NO 18
<211> LENGTH: 338
<212> TYPE: PRT
<213> ORGANISM: Brachyspira hyodysenteriae

<400> SEQUENCE: 18

```
Val Val Cys Asn Met Asn Lys Lys Asn Ile Ile Leu Leu Leu Ser Ile
 1               5                  10                  15

Ile Met Met Leu Ile Val Ser Cys Glu Glu Lys Thr Glu Ser Thr Val
            20                  25                  30

Thr Ile Gln Lys Tyr Pro Ile Arg Val Gly Tyr Met Pro Asp Phe Ser
        35                  40                  45

Gly Ser Ser Ala Val Ala Ile Ala Lys Glu Lys Gly Tyr Phe Asp Glu
    50                  55                  60

Glu Asn Leu Asp Val Thr Leu Val Glu Phe Leu Asp Gly Pro Ser Glu
65                  70                  75                  80

Val Glu Glu Met Leu Leu Lys Asn Leu Glu Phe Ala Tyr Ile Gly His
                85                  90                  95

Gly Ala His Ala Leu Ala Ile Glu Gly Lys Val Asn Val Leu Phe Pro
            100                 105                 110

Asn Gly Leu Ser Arg Ser Glu Gln Ile Ile Val Arg Asn Ala Ser Gln
        115                 120                 125

Ile Glu Ser Ile Lys Asp Leu Arg Gly Lys Lys Val Gly Thr Gln Leu
    130                 135                 140

Gly Thr Ser Ser Glu Ile Leu Leu Tyr Leu Ala Leu Gln Ser Leu Gly
145                 150                 155                 160

Ile Lys Ala Glu Glu Val Asp Ile Ile Asn Met Asp Gly Asn Thr Ile
                165                 170                 175

Val Ser Ser Ile Ala Asp Gly Thr Ile Asp Ala Ala Ser Val Gln Ala
            180                 185                 190

Pro Tyr Thr Phe Glu Ile Leu Asn Asn Thr Glu Asn Asn Val Lys Ser
        195                 200                 205

Ile Ala Thr Thr Val Asp Tyr Ser Asp Val Gly Ser Phe Pro Ser Ser
    210                 215                 220
```

```
Trp Ile Val Thr Pro Ser Tyr Gln Ser Asn Asn Thr Asp Ile Val Asn
225                 230                 235                 240

Arg Phe Ser Arg Ala Ile Leu Lys Ala Met Asp Tyr Arg Gln Leu Asn
            245                 250                 255

Met Ser Glu Ala Val Gln Leu Val Ala Asn Met Asn Ser Lys Thr Val
        260                 265                 270

Glu Glu Val Asp Leu Glu Arg Glu Thr Gly Val Trp Phe Ser Gly Asn
    275                 280                 285

Glu Ile Lys Gln Ala Tyr Ile Asn Gly Asp Ala Gly Lys Trp Tyr Lys
290                 295                 300

Thr Gln Gln Asn Ile Phe Ile Tyr Thr Lys Thr Ile Thr Asn Asn Ile
305                 310                 315                 320

Asp Ile Asn Asn Tyr Val Gln Leu Lys Tyr Met Val Asp Asn Val Phe
                325                 330                 335

Asn Glu

<210> SEQ ID NO 19
<211> LENGTH: 981
<212> TYPE: DNA
<213> ORGANISM: Brachyspira hyodysenteriae

<400> SEQUENCE: 19
atgaaaaaag ttttattagc tgtaacattt attttatat ttagtttttt aatatcatgc      60
ggtaagaaaa caaatgaaaa tgcaggtaaa ataagagtag catatcaccc aaatgtagga     120
ggagcttctg caataattac aggtatacag cagaattatt ttaaagatga aggtttggat     180
atagaacttg ttaaatttac aagcggacct acagaaatag cagctatggt ttcaggagat     240
atacaaatag gttatatagg ttttggagca catacattgg cagcagaagg aaaagttcaa     300
ataatagcta ctgacggaat agctgttgta gaaggtatta gaacattaaa aacttcaggc     360
ataaactctg ttgaaaaatt aaaaggcaga agtttaataa ctcaattagg tacatcagga     420
gaaactatta gatcaggtat tagcagga acaggagtta ataaaacaga tataaatata      480
cttaatgctg aagtttcaag tgctgttgca tcattcttgg ctaataaagt tgatgctata     540
tctgtatggc ctccttatac tgttgaaata gataatagaa ttggtataga gaatttgtat     600
attataaaac tcaggatgt aggagttgat tctactgcaa gctggatagt aactcctaac     660
tatttggaag ctaatactga tacagttata aaattcacaa gagcattata taaatcaatg     720
gattatagaa atcacatttt agatgaagct attacaaatg tatcaaatct tataggttta     780
gatatagcta cagtttcaca agagaaatac agttctgact ggatggattc tcaaacaatg     840
aaaagcagaa taaatgacgg aagcataagt aatatttata aaaaacaaat agactatttt     900
gtacagaata atagattaaa ttctgagcct gttcctgtag acaaatatgt aagaatcgac     960
attatagaaa aagcattaaa t                                               981

<210> SEQ ID NO 20
<211> LENGTH: 327
<212> TYPE: PRT
<213> ORGANISM: Brachyspira hyodysenteriae

<400> SEQUENCE: 20

Met Lys Lys Val Leu Leu Ala Val Thr Phe Ile Phe Ile Phe Ser Phe
1               5                   10                  15

Leu Ile Ser Cys Gly Lys Lys Thr Asn Glu Asn Ala Gly Lys Ile Arg
            20                  25                  30
```

Val Ala Tyr His Pro Asn Val Gly Gly Ala Ser Ala Ile Ile Thr Gly
         35                  40                  45

Ile Gln Gln Asn Tyr Phe Lys Asp Glu Gly Leu Asp Ile Glu Leu Val
 50                  55                  60

Lys Phe Thr Ser Gly Pro Thr Glu Ile Ala Ala Met Val Ser Gly Asp
 65                  70                  75                  80

Ile Gln Ile Gly Tyr Ile Gly Phe Gly Ala His Thr Leu Ala Ala Glu
                 85                  90                  95

Gly Lys Val Gln Ile Ile Ala Thr Asp Gly Ile Ala Val Val Glu Gly
            100                 105                 110

Ile Arg Thr Leu Lys Thr Ser Gly Ile Asn Ser Val Glu Lys Leu Lys
        115                 120                 125

Gly Arg Ser Leu Ile Thr Gln Leu Gly Thr Ser Gly Glu Thr Ile Ile
    130                 135                 140

Asp Gln Val Leu Ala Gly Thr Gly Val Asn Lys Thr Asp Ile Asn Ile
145                 150                 155                 160

Leu Asn Ala Glu Val Ser Ser Ala Val Ala Ser Phe Leu Ala Asn Lys
                165                 170                 175

Val Asp Ala Ile Ser Val Trp Pro Pro Tyr Thr Val Glu Ile Asp Asn
            180                 185                 190

Arg Ile Gly Ile Glu Asn Leu Tyr Ile Ile Lys Pro Gln Asp Val Gly
        195                 200                 205

Val Asp Ser Thr Ala Ser Trp Ile Val Thr Pro Asn Tyr Leu Glu Ala
    210                 215                 220

Asn Thr Asp Thr Val Ile Lys Phe Thr Arg Ala Leu Tyr Lys Ser Met
225                 230                 235                 240

Asp Tyr Arg Lys Ser His Leu Asp Glu Ala Ile Thr Asn Val Ser Asn
                245                 250                 255

Leu Ile Gly Leu Asp Ile Ala Thr Val Ser Gln Glu Lys Tyr Ser Ser
            260                 265                 270

Asp Trp Met Asp Ser Gln Thr Met Lys Ser Arg Ile Asn Asp Gly Ser
        275                 280                 285

Ile Ser Asn Ile Tyr Lys Lys Gln Ile Asp Tyr Phe Val Gln Asn Asn
    290                 295                 300

Arg Leu Asn Ser Glu Pro Val Pro Val Asp Lys Tyr Val Arg Ile Asp
305                 310                 315                 320

Ile Ile Glu Lys Ala Leu Asn
                325

<210> SEQ ID NO 21
<211> LENGTH: 1011
<212> TYPE: DNA
<213> ORGANISM: Brachyspira hyodysenteriae

<400> SEQUENCE: 21
atgaaaaaaa ctatgtttat ttctatttta tcaatggcag tgatatcttt aataatatcc      60
tgttcaggag gaaataaagc tcctgctgct tcagcagatg gtacacttga taaataaga     120 gttgcttatc ttgcagattt tgcaggaact tcttctgttg ctatagctca ggaaaaaggt    180
ttttttaaag aagaaaattt agatgttgaa ttagttaaat ttttaaatgg accttctgaa    240
gttgctgcta tgctctctgg agatatacaa tttgcatata taggacatgg tgcacattct    300
ctagctattc aaggtaaagt taatgtatta tttcctaatg gttaggtaa atctgaagaa    360 attatagttg gtaaatgggc caatgttaat gatttagcag gattaaaagg aaaaactata    420

-continued

```
ggtactcagc ttggtacttc tggagatata gtattggata ttgcattaag aaaagttgga      480
ctttccaaag aagatgttaa tgttgtcaat atggatgtaa gcggaatagt atcttctatg      540
attggtaaaa aagtagatgc agtttcttta tgggctcctt atactttga  ataactaaa       600 cagcttggag atgaagctgt tgtaattgct tctattacaa attatttaga tgaagctgta      660
tttcctagca gttggatagt tactcctgat tatcaaaata ataatcaaga catagtgaat      720
agattctcta aagctatatt taaagctatg gattatagaa gtgagaatat ggatgaggct      780
gttgaaattg tagctaaatt aaatggaact cctgttgatt ctgttgcttt agaaaaagaa      840
actgctatat ggcttagttc ttctgatata aaaaattctt atactgatgg aacagctgct      900
aaatggtatc aagctcagca gaaaatattt ttaaactcag aagtagttac tgaagaagta      960
gatgttaata attatgtaca gataaattat ataattgata atgtgcttaa a             1011
```

<210> SEQ ID NO 22
<211> LENGTH: 337
<212> TYPE: PRT
<213> ORGANISM: Brachyspira hyodysenteriae

<400> SEQUENCE: 22

```
Met Lys Lys Thr Met Phe Ile Ser Ile Leu Ser Met Ala Val Ile Ser
 1               5                  10                  15

Leu Ile Ile Ser Cys Ser Gly Gly Asn Lys Ala Pro Ala Ala Ser Ala
            20                  25                  30

Asp Gly Thr Leu Asp Lys Ile Arg Val Ala Tyr Leu Ala Asp Phe Ala
        35                  40                  45

Gly Thr Ser Ser Val Ala Ile Ala Gln Glu Lys Gly Phe Phe Lys Glu
    50                  55                  60

Glu Asn Leu Asp Val Glu Leu Val Lys Phe Leu Asn Gly Pro Ser Glu
65                  70                  75                  80

Val Ala Ala Met Leu Ser Gly Asp Ile Gln Phe Ala Tyr Ile Gly His
                85                  90                  95

Gly Ala His Ser Leu Ala Ile Gln Gly Lys Val Asn Val Leu Phe Pro
            100                 105                 110

Asn Gly Leu Gly Lys Ser Glu Glu Ile Ile Val Gly Lys Trp Ala Asn
        115                 120                 125

Val Asn Asp Leu Ala Gly Leu Lys Gly Lys Thr Ile Gly Thr Gln Leu
    130                 135                 140

Gly Thr Ser Gly Asp Ile Val Leu Asp Ile Ala Leu Arg Lys Val Gly
145                 150                 155                 160

Leu Ser Lys Glu Asp Val Asn Val Val Asn Met Asp Val Ser Gly Ile
                165                 170                 175

Val Ser Ser Met Ile Gly Lys Lys Val Asp Ala Val Ser Leu Trp Ala
            180                 185                 190

Pro Tyr Thr Phe Glu Ile Thr Lys Gln Leu Gly Asp Glu Ala Val Val
        195                 200                 205

Ile Ala Ser Ile Thr Asn Tyr Leu Asp Glu Ala Val Phe Pro Ser Ser
    210                 215                 220

Trp Ile Val Thr Pro Asp Tyr Gln Asn Asn Gln Asp Ile Val Asn
225                 230                 235                 240

Arg Phe Ser Lys Ala Ile Phe Lys Ala Met Asp Tyr Arg Ser Glu Asn
                245                 250                 255

Met Asp Glu Ala Val Glu Ile Val Ala Lys Leu Asn Gly Thr Pro Val
            260                 265                 270
```

Asp Ser Val Ala Leu Glu Lys Glu Thr Ala Ile Trp Leu Ser Ser
        275                 280                 285

Asp Ile Lys Asn Ser Tyr Thr Asp Gly Thr Ala Ala Lys Trp Tyr Gln
        290                 295                 300

Ala Gln Gln Lys Ile Phe Leu Asn Ser Glu Val Val Thr Glu Val
305                 310                 315                 320

Asp Val Asn Asn Tyr Val Gln Ile Asn Tyr Ile Ile Asp Asn Val Leu
                325                 330                 335

Lys

<210> SEQ ID NO 23
<211> LENGTH: 615
<212> TYPE: DNA
<213> ORGANISM: Brachyspira hyodysenteriae

<400> SEQUENCE: 23
atggcaagaa gaaaaaagaa aaatcatct cctttattaa tactatttat tttattaata      60
gcagcaggat actattatta taataatata tataataaaa agaaatatc aaaaacagaa    120
aagcccaaaa aagaaactat tacaagatac aatagagatg attggggaga ttgggctgat    180
gaagataatg acggacttaa tacaaggcat gaggtattag caagagcatc attagtaaaa    240
cctgtaatat ctaataacag agtaatatca ggaaaatggt atgataagtt tacaggaaaa    300
tattttacta atgcaaaaga tttagatata gatcatttag tgcctttaaa aaatgcacat    360
atcagcggtg ctagtaattg gagtaaagaa aagaaaaatg aatactacaa ttatatgaaa    420
aacgaaaatc atttggtagc tgtatcaaaa ggtgcaaatc gttctaaagg tgataaatcc    480
ccggtagaat ggctccctcc taatgaagaa tatcaatgcg aatatgtaag agaatggtat    540
aaaatcaaaa ccgattgggg gcttacaata gaagaaggtt ttgatgaagt ttcaaacaga    600
gtatgcaaag gaaaa                                                     615

<210> SEQ ID NO 24
<211> LENGTH: 205
<212> TYPE: PRT
<213> ORGANISM: Brachyspira hyodysenteriae

<400> SEQUENCE: 24

Met Ala Arg Arg Lys Lys Lys Ser Ser Pro Leu Leu Ile Leu Phe
1               5                   10                  15

Ile Leu Leu Ile Ala Ala Gly Tyr Tyr Tyr Asn Asn Ile Tyr Asn
                20                  25                  30

Lys Lys Glu Ile Ser Lys Thr Glu Lys Pro Lys Lys Glu Thr Ile Thr
        35                  40                  45

Arg Tyr Asn Arg Asp Asp Trp Gly Asp Trp Ala Asp Glu Asp Asn Asp
    50                  55                  60

Gly Leu Asn Thr Arg His Glu Val Leu Ala Arg Ala Ser Leu Val Lys
65                  70                  75                  80

Pro Val Ile Ser Asn Asn Arg Val Ile Ser Gly Lys Trp Tyr Asp Lys
                85                  90                  95

Phe Thr Gly Lys Tyr Phe Thr Asn Ala Lys Asp Leu Asp Ile Asp His
            100                 105                 110

Leu Val Pro Leu Lys Asn Ala His Ile Ser Gly Ala Ser Asn Trp Ser
        115                 120                 125

Lys Glu Lys Lys Asn Glu Tyr Tyr Asn Tyr Met Lys Asn Glu Asn His
    130                 135                 140

| Leu | Val | Ala | Val | Ser | Lys | Gly | Ala | Asn | Arg | Ser | Lys | Gly | Asp | Lys | Ser |
| --- | --- | --- | --- | --- | --- | --- | --- | --- | --- | --- | --- | --- | --- | --- | --- |
| 145 | | | | | 150 | | | | | 155 | | | | | 160 |

| Pro | Val | Glu | Trp | Leu | Pro | Pro | Asn | Glu | Glu | Tyr | Gln | Cys | Glu | Tyr | Val |
| --- | --- | --- | --- | --- | --- | --- | --- | --- | --- | --- | --- | --- | --- | --- | --- |
| | | | | 165 | | | | | 170 | | | | | 175 | |

| Arg | Glu | Trp | Tyr | Lys | Ile | Lys | Thr | Asp | Trp | Gly | Leu | Thr | Ile | Glu | Glu |
| --- | --- | --- | --- | --- | --- | --- | --- | --- | --- | --- | --- | --- | --- | --- | --- |
| | | | 180 | | | | | 185 | | | | | 190 | | |

| Gly | Phe | Asp | Glu | Val | Ser | Asn | Arg | Val | Cys | Lys | Gly | Lys |
| --- | --- | --- | --- | --- | --- | --- | --- | --- | --- | --- | --- | --- |
| | | 195 | | | | | 200 | | | | 205 | |

<210> SEQ ID NO 25
<211> LENGTH: 264
<212> TYPE: DNA
<213> ORGANISM: Brachyspira hyodysenteriae

<400> SEQUENCE: 25

```
atgaataaaa ttttttatga taaagcttgg gaagattatc tttattttca aaagaatgac        60
aaaaaaatat tacagaaaat taatgatttt ataaaagata tagaaagaaa tggcttatta       120
attggtatag gaaaaccaga gagattaaaa ggtgagttaa acggattgta ttcaaggcta       180
ataaatcaag aacatagatt agtatattat attgaagata taatttatt tatagttgga        240
tgtaaaacac attataaaaa taat                                              264
```

<210> SEQ ID NO 26
<211> LENGTH: 88
<212> TYPE: PRT
<213> ORGANISM: Brachyspira hyodysenteriae

<400> SEQUENCE: 26

| Met | Asn | Lys | Ile | Phe | Tyr | Asp | Lys | Ala | Trp | Glu | Asp | Tyr | Leu | Tyr | Phe |
| --- | --- | --- | --- | --- | --- | --- | --- | --- | --- | --- | --- | --- | --- | --- | --- |
| 1 | | | | 5 | | | | | 10 | | | | | 15 | |

| Gln | Lys | Asn | Asp | Lys | Lys | Ile | Leu | Gln | Lys | Ile | Asn | Asp | Phe | Ile | Lys |
| --- | --- | --- | --- | --- | --- | --- | --- | --- | --- | --- | --- | --- | --- | --- | --- |
| | | | 20 | | | | | 25 | | | | | 30 | | |

| Asp | Ile | Glu | Arg | Asn | Gly | Leu | Leu | Ile | Gly | Ile | Gly | Lys | Pro | Glu | Arg |
| --- | --- | --- | --- | --- | --- | --- | --- | --- | --- | --- | --- | --- | --- | --- | --- |
| | | 35 | | | | | 40 | | | | | 45 | | | |

| Leu | Lys | Gly | Glu | Leu | Asn | Gly | Leu | Tyr | Ser | Arg | Leu | Ile | Asn | Gln | Glu |
| --- | --- | --- | --- | --- | --- | --- | --- | --- | --- | --- | --- | --- | --- | --- | --- |
| | 50 | | | | | 55 | | | | | 60 | | | | |

| His | Arg | Leu | Val | Tyr | Tyr | Ile | Glu | Asp | Asn | Asn | Leu | Phe | Ile | Val | Gly |
| --- | --- | --- | --- | --- | --- | --- | --- | --- | --- | --- | --- | --- | --- | --- | --- |
| 65 | | | | | 70 | | | | | 75 | | | | | 80 |

| Cys | Lys | Thr | His | Tyr | Lys | Asn | Asn |
| --- | --- | --- | --- | --- | --- | --- | --- |
| | | | | 85 | | | |

<210> SEQ ID NO 27
<211> LENGTH: 1503
<212> TYPE: DNA
<213> ORGANISM: Brachyspira hyodysenteriae

<400> SEQUENCE: 27

```
gtgttaagga aattgatata tattattttt ttgcattcaa ttcttttaa ttttttatt         60
tttgcacaaa ctaatgaatc agctatatta aattcactc aatatatgga agaataaaa        120
tccataatac cagaaatgaa attaactgca tctcaagaaa gcaatgccta taataattta       180
acaaaagcaa aaagctccgg agacgttaaa tttgatttgc aggctggtgc tataggaatg       240
caaagccatt ttgatgaata caatttttta gcaacatcag attttaatta taatgggttt       300
agaataggtg caggattcag cggacttgta ccatactctg gaactagatg gtctgtagaa       360
attaaacatg acagtttttt cggcgacttt aatacaggag atatttcatt accggttgat       420
```

```
acgcctctag gtagaataaa tggaaaactt ccaaatttaa gtactaatga tttttaaatac     480 tattatccaa gcataaaaat tcaaatagct cagcctattt taagggattt ttttggtaaa     540
ttggatagat accctataaa agatgcagaa tatcagctta ccatagcaaa attaaaaaga     600
ataatagacg acaacagcgt attaacatct tatcagaaaa tttattatca atggataatg     660
gcaagaaaat taatagattt atatgatgat atgataagag aagcaagaag ttttgaaaat     720
caagtataca gaagatatac aagcggagtt atagataatg actcatatca gaatgcaaaa     780
agacaaacat taaaatatat agaagcaaga gataaatctg aattaatgct taaaaaaata     840
atgagaaata ttcaattctt tatacctgaa gaaaatatac agccaaatga agatgattgg     900
aatcagacat tagaaacctc tataaatgct aaaatagata tagtaccatt tttagaaagt     960
gctcagggac aaatggctta tcaattaaaa ttaagaagcg aatatgctat ttcagtaatg    1020
aaaaataatg ctctgcctga tttatctata gtaggaagcg tatcattatc aagtttagat    1080
gacagcggat atttaaatc tttttctacc atgactaatg ttgattattt tgtagggctt    1140
atgttttcct accccatagg cggacgtgat gctaaagcta aatggaaga tgcttatgct    1200 gctttgaatg ctgttacggc tgattttgat agggtgaaca gagattttga cgttcagata    1260
ggtacttatt atgatgagtt tgaggcatac aaaaaaatgc tagaaaataa aaaattggaa    1320
gttaatgcta tagtatcaag aataaatacg caaaatgcta aattcagaca aggaagactc    1380
cctatagatg aaataataaa tgcaaggctt gatttagcac aggcaagagc agaacttctt    1440
aatttgcagt atttaataat aagcactgtt atggattata attctctggt gctgcttaac    1500
aat                                                                  1503

<210> SEQ ID NO 28
<211> LENGTH: 501
<212> TYPE: PRT
<213> ORGANISM: Brachyspira hyodysenteriae

<400> SEQUENCE: 28

Val Leu Arg Lys Leu Ile Tyr Ile Ile Phe Leu His Ser Ile Leu Phe
 1               5                  10                  15

Asn Phe Phe Ile Phe Ala Gln Thr Asn Glu Ser Ala Ile Leu Asn Tyr
            20                  25                  30

Thr Gln Tyr Met Glu Arg Ile Lys Ser Ile Ile Pro Glu Met Lys Leu
        35                  40                  45

Thr Ala Ser Gln Glu Ser Asn Ala Tyr Asn Asn Leu Thr Lys Ala Lys
    50                  55                  60

Ser Ser Gly Asp Val Lys Phe Asp Leu Gln Ala Gly Ala Ile Gly Met
65                  70                  75                  80

Gln Ser His Phe Asp Glu Tyr Asn Phe Leu Ala Thr Ser Asp Phe Asn
                85                  90                  95

Tyr Asn Gly Phe Arg Ile Gly Ala Gly Phe Ser Gly Leu Val Pro Tyr
           100                 105                 110

Ser Gly Thr Arg Trp Ser Val Glu Ile Lys His Asp Ser Phe Phe Gly
       115                 120                 125

Asp Phe Asn Thr Gly Asp Ile Ser Leu Pro Val Asp Thr Pro Leu Gly
   130                 135                 140

Arg Ile Asn Gly Lys Leu Pro Asn Leu Ser Thr Asn Asp Phe Lys Tyr
145                 150                 155                 160

Tyr Tyr Pro Ser Ile Lys Ile Gln Ile Ala Gln Pro Ile Leu Arg Asp
                165                 170                 175
```

Phe Phe Gly Lys Leu Asp Arg Tyr Pro Ile Lys Asp Ala Glu Tyr Gln
            180                 185                 190

Leu Thr Ile Ala Lys Leu Lys Arg Ile Ile Asp Asp Asn Ser Val Leu
        195                 200                 205

Thr Ser Tyr Gln Lys Ile Tyr Tyr Gln Trp Ile Met Ala Arg Lys Leu
    210                 215                 220

Ile Asp Leu Tyr Asp Asp Met Ile Arg Glu Arg Ser Phe Glu Asn
225                 230                 235                 240

Gln Val Tyr Arg Arg Tyr Thr Ser Gly Val Ile Asp Asn Asp Ser Tyr
                245                 250                 255

Gln Asn Ala Lys Arg Gln Thr Leu Lys Tyr Ile Glu Ala Arg Asp Lys
            260                 265                 270

Ser Glu Leu Met Leu Lys Lys Ile Met Arg Asn Ile Gln Phe Phe Ile
        275                 280                 285

Pro Glu Glu Asn Ile Gln Pro Asn Glu Asp Asp Trp Asn Gln Thr Leu
    290                 295                 300

Glu Thr Ser Ile Asn Ala Lys Ile Asp Ile Val Pro Phe Leu Glu Ser
305                 310                 315                 320

Ala Gln Gly Gln Met Ala Tyr Gln Leu Lys Leu Arg Ser Glu Tyr Ala
                325                 330                 335

Ile Ser Val Met Lys Asn Asn Ala Leu Pro Asp Leu Ser Ile Val Gly
            340                 345                 350

Ser Val Ser Leu Ser Ser Leu Asp Asp Ser Gly Tyr Phe Lys Ser Phe
        355                 360                 365

Ser Thr Met Thr Asn Val Asp Tyr Phe Val Gly Leu Met Phe Ser Tyr
    370                 375                 380

Pro Ile Gly Gly Arg Asp Ala Lys Ala Lys Met Glu Asp Ala Tyr Ala
385                 390                 395                 400

Ala Leu Asn Ala Val Thr Ala Asp Phe Asp Arg Val Asn Arg Asp Phe
                405                 410                 415

Asp Val Gln Ile Gly Thr Tyr Tyr Asp Glu Phe Glu Ala Tyr Lys Lys
            420                 425                 430

Met Leu Glu Asn Lys Lys Leu Glu Val Asn Ala Ile Val Ser Arg Ile
        435                 440                 445

Asn Thr Gln Asn Ala Lys Phe Arg Gln Gly Arg Leu Pro Ile Asp Glu
    450                 455                 460

Ile Ile Asn Ala Arg Leu Asp Leu Ala Gln Ala Arg Ala Glu Leu Leu
465                 470                 475                 480

Asn Leu Gln Tyr Leu Ile Ile Ser Thr Val Met Asp Tyr Asn Ser Leu
                485                 490                 495

Val Leu Leu Asn Asn
            500

<210> SEQ ID NO 29
<211> LENGTH: 1386
<212> TYPE: DNA
<213> ORGANISM: Brachyspira hyodysenteriae

<400> SEQUENCE: 29
atggaaatac tactagttta tttatttgaa atatttataa ttattattct tattatgctc      60
tctgctttat tttctggaag tgagactgca tatacatcta ttgatgatgt tactttaatg     120
cgtttggtca gagagaaaaa aatcaaagaa gaagataaaa atattggga aaagtcaagt      180 tctatgatac ctaccctact tgttggtaat aacatagtta atatatcagc aagttccatt     240

```
ataactgtat ttgctgtaag gcttgctgac attctgccgc atgtatcaac aaatgtgatg    300
gttacaatat caactgccac aataacaata cttattatta tattcggaga aatacttcct    360
aaagtcttaa tgagagttaa tgctgaaaaa atgatgcctt atcttctata ttttatgaag    420
ttttgtcatt ttatattcaa gcctataact ttcttaatgg ataaagtaac tactttttata   480 atgaattatt ttgtacctaa agattaagaa gatgctgaaa aagaagtgc tttatcaagt     540 atggaagata tcactactat aatacatttg gggcataaag aaggaataat aaaagaatat    600
acacatgaaa tgcttacagg agtaatagat tttagaaata aaactgtaga agagataatg    660
acgccccgtg ttgatatggt atgtattgaa gctgaaacag atgtaaatga aataataaaa    720
cttactgtag aatcaggact ttcaagattt cctgtttatg aggaaacagt agatcatata    780
ataggtatat tccatacaag agctttattt aaagaatatg ttaaaggcgg cggaaagatg    840
aacaaagtaa aaagaaagc aatagattat ataatgcttc cctactttgt acctgaaact     900
aaaactataa gcagcttatt tagtgatatg caaaagaaaa aacttcagat ggtaattact    960
attgatgaat acggcggaac tgccggactt gttactatgg aagatataat agaagagata   1020
atgggtgata tagaagatga aagtgataaa aaagaagctg atgtaataag atttaaggga   1080
aaaagaatta taataaatgg aaatgcttct atagaagatg tcaacaaaac tttaaaatta   1140
gaattagagc atgaagaata tcaaactata gcaggatatg ttattgatat gcttgatcat   1200
atacctgaaa caaatgagag attcatatta aaaggatata gggtaagaat aatgaaagtt   1260
gaagacagaa gaatagttga atggaatttt actcctataa aatttgcaag aacaaatgaa   1320
agtgataata ttgatataca agagacatct gattcagaaa aaaatgattt agaaatttta   1380
aatgaa                                                               1386
```

<210> SEQ ID NO 30
<211> LENGTH: 462
<212> TYPE: PRT
<213> ORGANISM: Brachyspira hyodysenteriae

<400> SEQUENCE: 30

```
Met Glu Ile Leu Leu Val Tyr Leu Phe Glu Ile Phe Ile Ile Ile
  1               5                  10                  15

Leu Ile Met Leu Ser Ala Leu Phe Ser Gly Ser Glu Thr Ala Tyr Thr
                 20                  25                  30

Ser Ile Asp Asp Val Thr Leu Met Arg Leu Val Arg Glu Lys Lys Ile
             35                  40                  45

Lys Glu Glu Asp Lys Lys Tyr Trp Glu Lys Ser Ser Met Ile Pro
         50                  55                  60

Thr Leu Leu Val Gly Asn Asn Ile Val Asn Ile Ser Ala Ser Ser Ile
 65                  70                  75                  80

Ile Thr Val Phe Ala Val Arg Leu Ala Asp Ile Leu Pro His Val Ser
                 85                  90                  95

Thr Asn Val Met Val Thr Ile Ser Thr Ala Thr Ile Thr Ile Leu Ile
                100                 105                 110

Ile Ile Phe Gly Glu Ile Leu Pro Lys Val Leu Met Arg Val Asn Ala
            115                 120                 125

Glu Lys Met Met Pro Tyr Leu Leu Tyr Phe Met Lys Phe Cys His Phe
        130                 135                 140

Ile Phe Lys Pro Ile Thr Phe Leu Met Asp Lys Val Thr Thr Phe Ile
145                 150                 155                 160

Met Asn Tyr Phe Val Pro Lys Arg Leu Arg Asp Ala Glu Lys Arg Ser
```

```
                165                 170                 175
Ala Leu Ser Ser Met Glu Asp Ile Thr Thr Ile Ile His Leu Gly His
            180                 185                 190

Lys Glu Gly Ile Ile Lys Glu Tyr Thr His Glu Met Leu Thr Gly Val
        195                 200                 205

Ile Asp Phe Arg Asn Lys Thr Val Glu Glu Ile Met Thr Pro Arg Val
    210                 215                 220

Asp Met Val Cys Ile Glu Ala Glu Thr Asp Val Asn Glu Ile Ile Lys
225                 230                 235                 240

Leu Thr Val Glu Ser Gly Leu Ser Arg Phe Pro Val Tyr Glu Thr
            245                 250                 255

Val Asp His Ile Ile Gly Ile Phe His Thr Arg Ala Leu Phe Lys Glu
            260                 265                 270

Tyr Val Lys Gly Gly Lys Met Asn Lys Val Lys Lys Ala Ile
            275                 280                 285

Asp Tyr Ile Met Leu Pro Tyr Phe Val Pro Glu Thr Lys Thr Ile Ser
    290                 295                 300

Ser Leu Phe Ser Asp Met Gln Lys Lys Leu Gln Met Val Ile Thr
305                 310                 315                 320

Ile Asp Glu Tyr Gly Gly Thr Ala Gly Leu Val Thr Met Glu Asp Ile
            325                 330                 335

Ile Glu Glu Ile Met Gly Asp Ile Glu Asp Ser Asp Lys Lys Glu
            340                 345                 350

Ala Asp Val Ile Arg Phe Lys Gly Lys Arg Ile Ile Asn Gly Asn
            355                 360                 365

Ala Ser Ile Glu Asp Val Asn Lys Thr Leu Lys Leu Glu Leu Glu His
    370                 375                 380

Glu Glu Tyr Gln Thr Ile Ala Gly Tyr Val Ile Asp Met Leu Asp His
385                 390                 395                 400

Ile Pro Glu Thr Asn Glu Arg Phe Ile Leu Lys Gly Tyr Arg Val Arg
            405                 410                 415

Ile Met Lys Val Glu Asp Arg Arg Ile Val Glu Met Glu Phe Thr Pro
            420                 425                 430

Ile Lys Phe Ala Arg Thr Asn Glu Ser Asp Asn Ile Asp Ile Gln Glu
        435                 440                 445

Thr Ser Asp Ser Glu Lys Asn Asp Leu Glu Ile Leu Asn Glu
    450                 455                 460

<210> SEQ ID NO 31
<211> LENGTH: 1080
<212> TYPE: DNA
<213> ORGANISM: Brachyspira hyodysenteriae

<400> SEQUENCE: 31
atgaaagagt taggaatatc catttacccc tttcactcaa aaatggaaga taataaatat      60
tatatagatt tggcttctaa atacggattc gcaagatgtt ttatgtgtct gctttcagtt    120
gatagatcta aagatgaaat aataaatgaa ttttcaacta taataaatta tgctaaagaa    180
aaaggtataa aaactacttt agatatatct ccggctgtat tcaaacattt ggatatagat    240
tataaaaatc ttgactttt tcataaattg ggagcttggg gcgtaagatt agatttaggg    300
tttacaggta atgaagaaag tttaatgaca tatacgaat atgatttgaa aatagaatta    360
aatatgagca atgatacaga ttatcttgat aatataatga atattatcc taatactgat    420 aatttgatag gctgttataa tttctatcct catgcatata caggactaga cagaacactt    480
```

```
tttaaaagca gcatgaaacg ttttaaaaaa tattctataa gttcatctgc atttgttaat    540
gccaaagaag ctacttttgg accttggcct gtaagcgatg gtatttgcac attggaagaa    600
catagagata tgcctataga tgcacaggct atggaattat ttgctcttgg tgttgactgt    660
gttttcattg ctaactgtta tgcagatgaa atacttttta aaacattata taatatggat    720
aaaagattaa taacttttaa agtagaatta gttgattcta ttcctaaaga agaaaagagt    780
atagtattag atatgcttca tcaaaacaga ttagatgctt ctgctgatgt tataagatct    840
tcagatacaa gagcaaaata taagggacat aatttcaaaa tatttaatgc tgtttccgat    900
ataaaaagag gagatatatt aatagattca tcagaatacg gcagttatac cggagaaatg    960
cagatagctt tgaaagattt aaaaaatacc ggaagaacta atgtagtagg cagaattaaa   1020
gatgaatatt tatttctgct agattatata agtccggcta aaagatttat tataagagaa   1080
```

<210> SEQ ID NO 32
<211> LENGTH: 360
<212> TYPE: PRT
<213> ORGANISM: Brachyspira hyodysenteriae

<400> SEQUENCE: 32

```
Met Lys Glu Leu Gly Ile Ser Ile Tyr Pro Phe His Ser Lys Met Glu
1               5                   10                  15

Asp Asn Lys Tyr Tyr Ile Asp Leu Ala Ser Lys Tyr Gly Phe Ala Arg
            20                  25                  30

Cys Phe Met Cys Leu Leu Ser Val Asp Arg Ser Lys Asp Glu Ile Ile
        35                  40                  45

Asn Glu Phe Ser Thr Ile Ile Asn Tyr Ala Lys Glu Lys Gly Ile Lys
    50                  55                  60

Thr Thr Leu Asp Ile Ser Pro Ala Val Phe Lys His Leu Asp Ile Asp
65                  70                  75                  80

Tyr Lys Asn Leu Asp Phe Phe His Lys Leu Gly Ala Trp Gly Val Arg
                85                  90                  95

Leu Asp Leu Gly Phe Thr Gly Asn Glu Glu Ser Leu Met Thr Tyr Asn
            100                 105                 110

Glu Tyr Asp Leu Lys Ile Glu Leu Asn Met Ser Asn Asp Thr Asp Tyr
        115                 120                 125

Leu Asp Asn Ile Met Lys Tyr Tyr Pro Asn Thr Asp Asn Leu Ile Gly
    130                 135                 140

Cys Tyr Asn Phe Tyr Pro His Ala Tyr Thr Gly Leu Asp Arg Thr Leu
145                 150                 155                 160

Phe Lys Ser Ser Met Lys Arg Phe Lys Lys Tyr Ser Ile Ser Ser Ser
                165                 170                 175

Ala Phe Val Asn Ala Lys Glu Ala Thr Phe Gly Pro Trp Pro Val Ser
            180                 185                 190

Asp Gly Ile Cys Thr Leu Glu Glu His Arg Asp Met Pro Ile Asp Ala
        195                 200                 205

Gln Ala Met Glu Leu Phe Ala Leu Gly Val Asp Cys Val Phe Ile Ala
    210                 215                 220

Asn Cys Tyr Ala Asp Glu Asn Thr Phe Lys Thr Leu Tyr Asn Met Asp
225                 230                 235                 240

Lys Arg Leu Ile Thr Phe Lys Val Glu Leu Val Asp Ser Ile Pro Lys
                245                 250                 255

Glu Glu Lys Ser Ile Val Leu Asp Met Leu His Gln Asn Arg Leu Asp
            260                 265                 270
```

```
Ala Ser Ala Asp Val Ile Arg Ser Ser Asp Thr Arg Ala Lys Tyr Lys
        275                 280                 285

Gly His Asn Phe Lys Ile Phe Asn Ala Val Ser Asp Ile Lys Arg Gly
    290                 295                 300

Asp Ile Leu Ile Asp Ser Ser Glu Tyr Gly Ser Tyr Thr Gly Glu Met
305                 310                 315                 320

Gln Ile Ala Leu Lys Asp Leu Lys Asn Thr Gly Arg Thr Asn Val Val
                325                 330                 335

Gly Arg Ile Lys Asp Glu Tyr Leu Phe Leu Leu Asp Tyr Ile Ser Pro
            340                 345                 350

Ala Lys Arg Phe Ile Ile Arg Glu
        355                 360

<210> SEQ ID NO 33
<211> LENGTH: 2574
<212> TYPE: DNA
<213> ORGANISM: Brachyspira hyodysenteriae

<400> SEQUENCE: 33
```

| | | | | | |
|---|---|---|---|---|---|
| ttgatgaaga | aatacaagcc | tgaaacaaaa | caagaattag | aacaattggt | atatactgac | 60 |
| ggaataaaac | tctatgatgt | agatacgagt | cttataacag | atatgagcga | gctttttcat | 120 |
| aacagcacca | gaaagatttt | tgaaggcata | aagattgggg | acgtttctaa | tgttgaggat | 180 |
| atgtcctata | tgtttgccca | tatgagttat | gatagttatg | aaaaccgttc | taaagctaag | 240 |
| tttaatcata | atcttaataa | ttggaatgta | tctaaagtta | agcatatgag | ttttatgttt | 300 |
| tattattgtc | aggattttaa | tcagcccttta | gataaatggg | acgtttctaa | tgttcaggat | 360 |
| acatttagaa | tgtttgataa | ttgtaaaaaa | ttcaatcagc | ctttaaatag | ctggaatgta | 420 |
| tctaatgtaa | caaatatgag | cggtatgttt | caggtagcag | aaagtttcaa | tcagccttta | 480 |
| gacaagtggg | acgtttcaaa | agttacaact | atgagggcta | tgtttaatta | tgctaaagct | 540 |
| tttaatcaag | atataagtaa | ttggaatgtt | agtaaagttg | aagatatggg | ttatatgttt | 600 |
| agtatatgcg | ttaattttaa | tcagcctatt | aatgattggg | acgtatctaa | agtaaaaact | 660 |
| atggaaggta | tgtttagaag | tgcttttaaa | ttcaatcagc | ctttagataa | atggaatact | 720 |
| tcaaaggttg | aaaatatgaa | tcagatgttt | aatgaggctt | taaaatttaa | tcagccttta | 780 |
| aatagctgga | atgtttccaa | tgtaaaaact | atggaatgta | tgtttcgcgg | tactgaagct | 840 |
| tttaatcagc | ctttggataa | atgggataca | aaaaaattaa | aaacaatgtt | tggaatgttt | 900 |
| gactttgctg | aaggttataa | tagttttgac | tcattagcaa | actgggattt | aaataaagta | 960 |
| tcagaaatga | gtaatttatg | ttttaaaagg | tatgaagaac | ttcctttaag | aattaaagca | 1020 |
| tatcttcagg | catttatgg | ttcttataaa | gattatttaa | ctgttacaaa | agataatgtc | 1080 |
| aaagaaatat | atgatcttat | ttcaaaagac | acaaataaaa | aagttttgtc | atttaaaaag | 1140 |
| agattagaaa | gcgagtttag | tgaggaactt | tcatctgtta | cagataatta | taatttcaaa | 1200 |
| tctatagaag | aagcagaaaa | gtatgttgaa | aataattata | ataaaaaaga | tgataagaaa | 1260 |
| gttagcttta | taaatgatta | taaagttttg | ataaaagata | aatcaagaga | agttgaaaat | 1320 |
| aaagttttaa | aatatatata | tttggaatat | ttgctcccttа | aaagagatgt | taaaaaatta | 1380 |
| gtgcagattg | ataatatagt | taatttactt | gataaagaat | catttataaa | atttattaaa | 1440 |
| aatgttatg | atgaaactaa | taagaaaca | gccgctttta | tttatggcat | atacggagga | 1500 |
| gatgaggcag | taaaaaatat | atataaaaaa | gaaaaagaca | ctaaactttc | actattaata | 1560 |

-continued

```
attaaattaa atatagaaag taaatatgca cttagaatat tatatgaaat atattcaaat   1620
acaaaaaaat ctgaagttag ttatgaagct gataaattga ttgatgaagt aatggaaaaa   1680
atggatatta gttataatga attccaatta agatattcat ctgatttagg atttaattct   1740
aaaggtgaaa aagaattgaa taaagattat aaattaattt tgaatagcga ttattctttg   1800 agtcttttg atataaaaaa taataaggaa cttaaaaaag cccctcaaaa tcttaatgaa    1860
gatttaaaag aagaaataac aaaattaaga aaagaaattc cttattttat gaaaaacact   1920
gcttctcttt tagctgtttt attagcaagc ggtgaaaaat acagttatga tttattcaaa   1980
gagattttta ttgataatgc cattatgaat agatttgctt catctttaat atggaatcta   2040
tatgacaaag attctaattt tataacaact ttcagatatt caggcgatgg aagttattca   2100
aactgtgaag atgaagaagt aaaaattaat gataatagtt ttgtaagttt agcaagccct   2160
gtggaaatgg atgatgaaac tatagataaa tggagaaaac agcttgaaga ttatgagata   2220
gcacagccaa taagtcaatt aactgtcata aaattagata aagataattt gaaaagcgaa   2280
gtagaaaaaa tagataattt agaaatagct tatggtactt tcaaggcttt cggtgaaaga   2340
tatgaaatgt atagcgagta tataggttat gatgttgtta aaagttattc attagaatca   2400
aagaacggag acactttcac tatagacgct gatgttaatt caaaaactga ttttcatgac   2460
agagtaaaaa ttaatattaa ttttgataat gaaaatggtg aggaagtaag taaaagattt   2520
atttatactt tgttagtatt aatgatttgg gattttagat aacagatttt attt          2574
```

<210> SEQ ID NO 34
<211> LENGTH: 858
<212> TYPE: PRT
<213> ORGANISM: Brachyspira hyodysenteriae

<400> SEQUENCE: 34

```
Leu Met Lys Lys Tyr Lys Pro Glu Thr Lys Gln Glu Leu Glu Gln Leu
  1               5                  10                  15

Val Tyr Thr Asp Gly Ile Lys Leu Tyr Asp Val Asp Thr Ser Leu Ile
             20                  25                  30

Thr Asp Met Ser Glu Leu Phe His Asn Ser Thr Arg Lys Asp Phe Glu
         35                  40                  45

Gly Ile Glu Asp Trp Asp Val Ser Asn Val Glu Asp Met Ser Tyr Met
     50                  55                  60

Phe Ala His Met Ser Tyr Asp Ser Tyr Glu Asn Arg Ser Lys Ala Lys
 65                  70                  75                  80

Phe Asn His Asn Leu Asn Asn Trp Asn Val Ser Lys Val Lys His Met
                 85                  90                  95

Ser Phe Met Phe Tyr Tyr Cys Gln Asp Phe Asn Gln Pro Leu Asp Lys
            100                 105                 110

Trp Asp Val Ser Asn Val Gln Asp Thr Phe Arg Met Phe Asp Asn Cys
        115                 120                 125

Lys Lys Phe Asn Gln Pro Leu Asn Ser Trp Asn Val Ser Asn Val Thr
    130                 135                 140

Asn Met Ser Gly Met Phe Gln Val Ala Glu Ser Phe Asn Gln Pro Leu
145                 150                 155                 160

Asp Lys Trp Asp Val Ser Lys Val Thr Thr Met Arg Ala Met Phe Asn
                165                 170                 175

Tyr Ala Lys Ala Phe Asn Gln Asp Ile Ser Asn Trp Asn Val Ser Lys
            180                 185                 190

Val Glu Asp Met Gly Tyr Met Phe Ser Ile Cys Val Asn Phe Asn Gln
```

```
            195                 200                 205
Pro Ile Asn Asp Trp Asp Val Ser Lys Val Lys Thr Met Glu Gly Met
210                 215                 220

Phe Arg Ser Ala Phe Lys Phe Asn Gln Pro Leu Asp Lys Trp Asn Thr
225                 230                 235                 240

Ser Lys Val Glu Asn Met Asn Gln Met Phe Asn Glu Ala Leu Lys Phe
                245                 250                 255

Asn Gln Pro Leu Asn Ser Trp Asn Val Ser Asn Val Lys Thr Met Glu
                260                 265                 270

Cys Met Phe Arg Gly Thr Glu Ala Phe Asn Gln Pro Leu Asp Lys Trp
                275                 280                 285

Asp Thr Lys Lys Leu Lys Thr Met Phe Gly Met Phe Asp Phe Ala Glu
290                 295                 300

Gly Tyr Asn Ser Phe Asp Ser Leu Ala Asn Trp Asp Leu Asn Lys Val
305                 310                 315                 320

Ser Glu Met Ser Asn Leu Cys Phe Lys Arg Tyr Glu Leu Pro Leu
                325                 330                 335

Arg Ile Lys Ala Tyr Leu Gln Ala Phe Tyr Gly Ser Tyr Lys Asp Tyr
                340                 345                 350

Leu Thr Val Thr Lys Asp Asn Val Lys Glu Ile Tyr Asp Leu Ile Ser
                355                 360                 365

Lys Asp Thr Asn Lys Lys Val Leu Ser Phe Lys Lys Arg Leu Glu Ser
370                 375                 380

Glu Phe Ser Glu Glu Leu Ser Ser Val Thr Asp Asn Tyr Asn Phe Lys
385                 390                 395                 400

Ser Ile Glu Glu Ala Glu Lys Tyr Val Glu Asn Asn Tyr Asn Lys Lys
                405                 410                 415

Asp Asp Lys Lys Val Ser Phe Ile Asn Asp Tyr Lys Val Leu Ile Lys
                420                 425                 430

Asp Lys Ser Arg Glu Val Glu Asn Lys Val Leu Lys Tyr Ile Tyr Leu
                435                 440                 445

Glu Tyr Leu Leu Leu Lys Arg Asp Val Lys Lys Leu Val Gln Ile Asp
450                 455                 460

Asn Ile Val Asn Leu Leu Asp Lys Glu Ser Phe Ile Lys Phe Ile Lys
465                 470                 475                 480

Asn Val Tyr Asp Glu Thr Asn Lys Glu Thr Ala Ala Phe Ile Tyr Gly
                485                 490                 495

Ile Tyr Gly Gly Asp Glu Ala Val Lys Asn Ile Tyr Lys Lys Glu Lys
                500                 505                 510

Asp Thr Lys Leu Ser Leu Leu Ile Ile Lys Leu Asn Ile Glu Ser Lys
                515                 520                 525

Tyr Ala Leu Arg Ile Leu Tyr Glu Ile Tyr Ser Asn Thr Lys Lys Ser
530                 535                 540

Glu Val Ser Tyr Glu Ala Asp Lys Leu Ile Asp Glu Val Met Glu Lys
545                 550                 555                 560

Met Asp Ile Ser Tyr Asn Glu Phe Gln Leu Arg Tyr Ser Ser Asp Leu
                565                 570                 575

Gly Phe Asn Ser Lys Gly Glu Lys Glu Leu Asn Lys Asp Tyr Lys Leu
                580                 585                 590

Ile Leu Asn Ser Asp Tyr Ser Leu Ser Leu Phe Asp Ile Lys Asn Asn
                595                 600                 605

Lys Glu Leu Lys Lys Ala Pro Gln Asn Leu Asn Glu Asp Leu Lys Glu
610                 615                 620
```

```
Glu Ile Thr Lys Leu Arg Lys Glu Ile Pro Tyr Phe Met Lys Asn Thr
625                 630                 635                 640

Ala Ser Leu Leu Ala Val Leu Leu Ala Ser Gly Glu Lys Tyr Ser Tyr
            645                 650                 655

Asp Leu Phe Lys Glu Ile Phe Ile Asp Asn Ala Ile Met Asn Arg Phe
        660                 665                 670

Ala Ser Ser Leu Ile Trp Asn Leu Tyr Asp Lys Asp Ser Asn Phe Ile
    675                 680                 685

Thr Thr Phe Arg Tyr Ser Gly Asp Ser Tyr Ser Asn Cys Glu Asp
690                 695                 700

Glu Glu Val Lys Ile Asn Asp Asn Ser Phe Val Ser Leu Ala Ser Pro
705                 710                 715                 720

Val Glu Met Asp Asp Glu Thr Ile Asp Lys Trp Arg Lys Gln Leu Glu
            725                 730                 735

Asp Tyr Glu Ile Ala Gln Pro Ile Ser Gln Leu Thr Val Ile Lys Leu
        740                 745                 750

Asp Lys Asp Asn Leu Lys Ser Glu Val Glu Lys Ile Asp Asn Leu Glu
    755                 760                 765

Ile Ala Tyr Gly Thr Phe Lys Ala Phe Gly Arg Tyr Glu Met Tyr
770                 775                 780

Ser Glu Tyr Ile Gly Tyr Asp Val Val Lys Ser Tyr Ser Leu Glu Ser
785                 790                 795                 800

Lys Asn Gly Asp Thr Phe Thr Ile Asp Ala Asp Val Asn Ser Lys Thr
            805                 810                 815

Asp Phe His Asp Arg Val Lys Ile Asn Ile Asn Phe Asp Asn Glu Asn
        820                 825                 830

Gly Glu Glu Val Ser Lys Arg Phe Ile Tyr Thr Leu Leu Val Leu Met
    835                 840                 845

Ile Trp Asp Phe Arg Leu Thr Asp Leu Phe
850                 855

<210> SEQ ID NO 35
<211> LENGTH: 2100
<212> TYPE: DNA
<213> ORGANISM: Brachyspira hyodysenteriae

<400> SEQUENCE: 35
atgagaataa aacttctagc ggttatagta ttattttaa tgactatatc gctttcatac      60
actttcgaca aaactccgta ttatgtaaac acagaaactt atgactcata cagagagtta     120
ttgagagggg tgcattatta taatcaggaa agatatgatg catccatagc tagttttaga     180
aactctctta atacaaatcc tactgataag ttcataagat attggtatag taagtctta      240 tacaaagccg atatatgtc cttagctatt aatgaatggc ttaatattac gagaatgggt      300
tatgaagatc ctataatact ttctaaaatt aataaatatg attctgcaaa tgttaatgaa     360
gagagagaaa atattttgag taattttatt tatttgaaag cattctctac aaatcttaat     420
tttagaaaaa atattaatca gcctatacaa ataaaagtaa tgtctgatgg aagtttatat     480
gttttggatt atagtgattc ttcattaaag aaatttgata ttaatggaaa tctaataggt     540
aaaatatccc atggaaaaag attagaaaaa cagcagacta gctggtggag aaatttactt     600
cagtttgcag caaaagttta tccttatgaa aaattagaaa atcctagagg ttttgatata     660
gatgcaaacg gatatatata tatagccaat actaaaaaag ataaaatatt aaatatgat      720 gctaatcata attatattac aaatattggg gtatccggtg taagtaatgg tcagcttctt     780
```

```
ggaccttcat ctgttgctgt tgatagagaa ggaaatttat atgtttctga tacaggaaat    840
aatagaatag ttatatttga tatagaagga aatttcttat atagttttgg aaaacttggt    900
gaaaataatg gagagttctt ttctcctgcg ggcatagcgg ttgatgacaa atatatttat    960
gttgctgata tgggtaataa aagaatacag caatttgatt tgagcggaaa ttatattcag   1020
agtataaagc ataatttatt taatgagcct agaggtttat cttttgctaa agatggaaat   1080
ctttatatag ctgatggaag taaggttttt tattataata tagctgaatc agattttaca   1140
atatttaata attccgaaag atatacagta actcctactt ctattgctga gggacctgat   1200
ggaaatatat atcttactga tttatgtct ggaagaattg atgtatatac tagaaaagaa   1260
gaatattacg ctaatttaga tgtatttgta gacagagaat atttaaatag attccctgtt   1320
gttgtagctt ctgttacagt gagagataga gctatgaacc ctgtagttgg attaactcct   1380
gaaaatttct ttgttacaga gaatgcaggt gttgctcata aagttggttt ttatgatgct   1440
cctgaattgc atgaatatag attcgtgtat ttaatagaag atagtcttgc tgctaaacct   1500
tatgagagca gaattaaaga agagattagt aattttacta tgagcttaac taataatgat   1560
gaagttttag ttatacatta taatgatcag gtttacaagt ctgataatta tgatgctaga   1620
aatttaagaa tacttgaaaa tgctaatgct ttccatttta caggcggaat atctgctttg   1680
gatgatgctt attatgaagc tataagactt tcaggaaata gttttaagaa aactgctatt   1740
atacattttt cagtaactag tcctgacgac agagtatttg atatgatgaa ctttaatgat   1800
gtagcaagtt ttgctaaaaa caatgcagtt tcattaaacc aagtttatat cggtacaaat   1860
aaatctaatt atttcttaga tttaatgact gagaatactt acggttatat tatagatgct   1920
gattattcta taaattatac tgctgagctt aatagaatga aaaatataaa ttttggaaga   1980
tatttcatat actataacag ttttagaaat ttagctcagt caggacagtt tagggctttg   2040
aatgttaagg ttcaatatag agatatgtat ggtgaagaag aagttggtta tgtagtgcca   2100
```

<210> SEQ ID NO 36
<211> LENGTH: 700
<212> TYPE: PRT
<213> ORGANISM: Brachyspira hyodysenteriae

<400> SEQUENCE: 36

Met Arg Ile Lys Leu Leu Ala Val Ile Val Leu Phe Leu Met Thr Ile
1               5                   10                  15

Ser Leu Ser Tyr Thr Phe Asp Lys Thr Pro Tyr Tyr Val Asn Thr Glu
            20                  25                  30

Thr Tyr Asp Ser Tyr Arg Glu Leu Leu Arg Gly Val His Tyr Tyr Asn
        35                  40                  45

Gln Glu Arg Tyr Asp Ala Ser Ile Ala Ser Phe Arg Asn Ser Leu Asn
    50                  55                  60

Thr Asn Pro Thr Asp Lys Phe Ile Arg Tyr Trp Tyr Ser Lys Ser Leu
65                  70                  75                  80

Tyr Lys Ala Gly Tyr Met Ser Leu Ala Ile Asn Glu Trp Leu Asn Ile
                85                  90                  95

Thr Arg Met Gly Tyr Glu Asp Pro Ile Ile Leu Ser Lys Ile Asn Lys
            100                 105                 110

Tyr Asp Ser Ala Asn Val Asn Glu Glu Arg Glu Asn Ile Leu Ser Asn
        115                 120                 125

Phe Ile Tyr Leu Lys Ala Phe Ser Thr Asn Leu Asn Phe Arg Lys Asn
    130                 135                 140

-continued

```
Ile Asn Gln Pro Ile Gln Ile Lys Val Met Ser Asp Gly Ser Leu Tyr
145                 150                 155                 160

Val Leu Asp Tyr Ser Asp Ser Leu Lys Lys Phe Asp Ile Asn Gly
            165                 170                 175

Asn Leu Ile Gly Lys Ile Ser His Gly Lys Arg Leu Glu Lys Gln Gln
            180                 185                 190

Thr Ser Trp Trp Arg Asn Leu Leu Gln Phe Ala Ala Lys Val Tyr Pro
            195                 200                 205

Tyr Glu Lys Leu Glu Asn Pro Arg Gly Phe Asp Ile Asp Ala Asn Gly
210                 215                 220

Tyr Ile Tyr Ile Ala Asn Thr Lys Lys Asp Lys Ile Leu Lys Tyr Asp
225                 230                 235                 240

Ala Asn His Asn Tyr Ile Thr Asn Ile Gly Val Ser Gly Val Ser Asn
            245                 250                 255

Gly Gln Leu Leu Gly Pro Ser Ser Val Ala Val Asp Arg Glu Gly Asn
            260                 265                 270

Leu Tyr Val Ser Asp Thr Gly Asn Asn Arg Ile Val Ile Phe Asp Ile
            275                 280                 285

Glu Gly Asn Phe Leu Tyr Ser Phe Gly Lys Leu Gly Glu Asn Asn Gly
290                 295                 300

Glu Phe Phe Ser Pro Ala Gly Ile Ala Val Asp Asp Lys Tyr Ile Tyr
305                 310                 315                 320

Val Ala Asp Met Gly Asn Lys Arg Ile Gln Gln Phe Asp Leu Ser Gly
            325                 330                 335

Asn Tyr Ile Gln Ser Ile Lys His Asn Leu Phe Asn Glu Pro Arg Gly
            340                 345                 350

Leu Ser Phe Ala Lys Asp Gly Asn Leu Tyr Ile Ala Asp Gly Ser Lys
            355                 360                 365

Val Phe Tyr Tyr Asn Ile Ala Glu Ser Asp Phe Thr Ile Phe Asn Asn
370                 375                 380

Ser Glu Arg Tyr Thr Val Thr Pro Thr Ser Ile Ala Glu Gly Pro Asp
385                 390                 395                 400

Gly Asn Ile Tyr Leu Thr Asp Phe Met Ser Gly Arg Ile Asp Val Tyr
            405                 410                 415

Thr Arg Lys Glu Glu Tyr Tyr Ala Asn Leu Asp Val Phe Val Asp Arg
            420                 425                 430

Glu Tyr Leu Asn Arg Phe Pro Val Val Ala Ser Val Thr Val Arg
            435                 440                 445

Asp Arg Ala Met Asn Pro Val Val Gly Leu Thr Pro Glu Asn Phe Phe
            450                 455                 460

Val Thr Glu Asn Ala Gly Val Ala His Lys Val Gly Phe Tyr Asp Ala
465                 470                 475                 480

Pro Glu Leu His Glu Tyr Arg Phe Val Tyr Leu Ile Glu Asp Ser Leu
            485                 490                 495

Ala Ala Lys Pro Tyr Glu Ser Arg Ile Lys Glu Ile Ser Asn Phe
            500                 505                 510

Thr Met Ser Leu Thr Asn Asn Asp Glu Val Leu Val Ile His Tyr Asn
            515                 520                 525

Asp Gln Val Tyr Lys Ser Asp Asn Tyr Asp Ala Arg Asn Leu Arg Ile
            530                 535                 540

Leu Glu Asn Ala Asn Ala Phe His Phe Thr Gly Gly Ile Ser Ala Leu
545                 550                 555                 560
```

```
Asp Asp Ala Tyr Tyr Glu Ala Ile Arg Leu Ser Gly Asn Ser Phe Lys
                565                 570                 575

Lys Thr Ala Ile Ile His Phe Ser Val Thr Ser Pro Asp Arg Val
            580                 585                 590

Phe Asp Met Met Asn Phe Asn Asp Val Ala Ser Phe Ala Lys Asn Asn
        595                 600                 605

Ala Val Ser Leu Asn Gln Val Tyr Ile Gly Thr Asn Lys Ser Asn Tyr
    610                 615                 620

Phe Leu Asp Leu Met Thr Glu Asn Thr Tyr Gly Tyr Ile Ile Asp Ala
625                 630                 635                 640

Asp Tyr Ser Ile Asn Tyr Thr Ala Glu Leu Asn Arg Met Lys Asn Ile
                645                 650                 655

Asn Phe Gly Arg Tyr Phe Ile Tyr Tyr Asn Ser Phe Arg Asn Leu Ala
            660                 665                 670

Gln Ser Gly Gln Phe Arg Ala Leu Asn Val Lys Val Gln Tyr Arg Asp
        675                 680                 685

Met Tyr Gly Glu Glu Val Gly Tyr Val Val Pro
    690                 695                 700
```

<210> SEQ ID NO 37
<211> LENGTH: 711
<212> TYPE: DNA
<213> ORGANISM: Brachyspira hyodysenteriae

<400> SEQUENCE: 37

```
atgatagaat caatacaaag aatacatgcc agaataggcg agattcagga tactttttaat    60
aaattaggtt ttgctcctat taatactcag attcctacta aaccttttgc tgaacattta   120
aatgaagcta tggcagaaaa caaagtcaat aatattgatg ttctatagt taatgataca   180
aataaaaagt tagataatgg aaaagtaatt aatggagata cttcttctga tgctttcaaa   240
ggaaatatat catttggtgt ttatgatagt aatacaaata attttgctaa agctataaat   300
gcttataaaa aagcttcagt agaaagtttc cctactaaat atgatgatat aattaaagag   360
gcagcagaga atattctttt gcctgaaaat ttaataaaag cggttataaa gcaggaatca   420
aactatgtgc ctaatgctgt aagtcataaa ggtgctgttg gtttgatgca gataatgccg   480
caaacaggtg ttggcttagg tattactgat acagaaatgc ttaaagatcc atacactaat   540
ataatggctg gaagcagata tttatcacag atgttaaaca gatatgatgg aagacttgat   600
ttatctttat ctgcttataa tgccggacct gctttggtag acagattaca gagaatccct   660
aatatagagg aaactcaaaa ctatgttaaa aacattatag gatatataaa g            711
```

<210> SEQ ID NO 38
<211> LENGTH: 237
<212> TYPE: PRT
<213> ORGANISM: Brachyspira hyodysenteriae

<400> SEQUENCE: 38

```
Met Ile Glu Ser Ile Gln Arg Ile His Ala Arg Ile Gly Glu Ile Gln
1               5                   10                  15

Asp Thr Phe Asn Lys Leu Gly Phe Ala Pro Ile Asn Thr Gln Ile Pro
            20                  25                  30

Thr Lys Pro Phe Ala Glu His Leu Asn Glu Ala Met Ala Glu Asn Lys
        35                  40                  45

Val Asn Asn Ile Asp Gly Ser Ile Val Asn Asp Thr Asn Lys Lys Leu
    50                  55                  60
```

```
Asp Asn Gly Lys Val Ile Asn Gly Asp Thr Ser Ser Asp Ala Phe Lys
 65                  70                  75                  80

Gly Asn Ile Ser Phe Gly Val Tyr Asp Ser Asn Thr Asn Asn Phe Ala
                 85                  90                  95

Lys Ala Ile Asn Ala Tyr Lys Lys Ala Ser Val Glu Ser Phe Pro Thr
            100                 105                 110

Lys Tyr Asp Asp Ile Ile Lys Glu Ala Ala Glu Lys Tyr Ser Leu Pro
        115                 120                 125

Glu Asn Leu Ile Lys Ala Val Ile Lys Gln Glu Ser Asn Tyr Val Pro
    130                 135                 140

Asn Ala Val Ser His Lys Gly Ala Val Gly Leu Met Gln Ile Met Pro
145                 150                 155                 160

Gln Thr Gly Val Gly Leu Gly Ile Thr Asp Thr Glu Met Leu Lys Asp
                165                 170                 175

Pro Tyr Thr Asn Ile Met Ala Gly Ser Arg Tyr Leu Ser Gln Met Leu
            180                 185                 190

Asn Arg Tyr Asp Gly Arg Leu Asp Leu Ser Leu Ser Ala Tyr Asn Ala
        195                 200                 205

Gly Pro Ala Leu Val Asp Arg Leu Gln Arg Ile Pro Asn Ile Glu Glu
    210                 215                 220

Thr Gln Asn Tyr Val Lys Asn Ile Ile Gly Tyr Ile Lys
225                 230                 235

<210> SEQ ID NO 39
<211> LENGTH: 258
<212> TYPE: DNA
<213> ORGANISM: Brachyspira hyodysenteriae

<400> SEQUENCE: 39
atgaaaatag ttttaatga aagagcttgg caggaatata tagagtgggt atcagaagat      60
aaaaaaatag taaaaaaaat taacgacttg attaagata taataagaaa tccttgtgat     120
ggaataggaa aagcagaaaa attaaaatat gataaaaaag atctttactc tagaagaata    180
aataaagaac atagattagt atatcatata gaaaataatc aattaataat aacatcttgt    240
aaataccatt atgataag                                                  258

<210> SEQ ID NO 40
<211> LENGTH: 86
<212> TYPE: PRT
<213> ORGANISM: Brachyspira hyodysenteriae

<400> SEQUENCE: 40

Met Lys Ile Val Phe Asn Glu Arg Ala Trp Gln Glu Tyr Ile Glu Trp
  1               5                  10                  15

Val Ser Glu Asp Lys Lys Ile Val Lys Lys Ile Asn Asp Leu Ile Lys
             20                  25                  30

Asp Ile Ile Arg Asn Pro Cys Asp Gly Ile Gly Lys Ala Glu Lys Leu
         35                  40                  45

Lys Tyr Asp Lys Lys Asp Leu Tyr Ser Arg Arg Ile Asn Lys Glu His
     50                  55                  60

Arg Leu Val Tyr His Ile Glu Asn Asn Gln Leu Ile Ile Thr Ser Cys
 65                  70                  75                  80

Lys Tyr His Tyr Asp Lys
                 85

<210> SEQ ID NO 41
```

<211> LENGTH: 2646
<212> TYPE: DNA
<213> ORGANISM: Brachyspira hyodysenteriae

<400> SEQUENCE: 41

```
gtggagattt tagtgaattt tattaagaaa aattgtatta ttttattttc atttctttta     60
cttgctgcag ctttattaat atctgcagag agtgactttg aaaatttaca aacagcaaga    120
aatatagctg tatatgaagg gcttacaata aaccgtatag atgttacagg tgaagtaagg    180
cttacaaagg aacaaataat aaacaatttt cctataaaag ccggcagtaa atttcaaaga    240
acagaaataa atgcagccat aaaaaaacta tttgatacgc agttattcga tagagtggca    300
atagatgcaa acagagaaga tgacggagta gttttaaata ttgtagtagc tgaaagattc    360
ataataaaag atatagaata tataggaaat aaaagattaa gcagaacagc acttaatgat    420
gccgtaaaac caattatgaa agcaggtgat ccttatatac ctcagaaatt aaatgatgct    480
gttaatgcta taataacaaa ttatcaagat aaaggatatt tgaaagctta tgttgagcct    540
aaagtaatag aaaataaaga tacttctgat gttttaatac aaatgaacat agtagaaggt    600
aatgaagtta aggttgctaa tataagattc catggtaata cacattttac tgataatgaa    660
cttaaaagac agatgtcaac aaaagaaaat ggatttatga ctcttggaaa atttaatgag    720
tttacatttg atggagacaa agataaaatt gttaaatact atgcagatag aggttactat    780
agagccaaag ttgataatgt aaagttcaca tatcaatgga gaaatcctga aataaaaaat    840
gaacaggatt taataataga tatatatgtt acagagggag ataaatatta tttcggagat    900
ataggattta aaggaaactt tataatacct tctgaaaata tacaaaaaga tataaaatca    960
aaaaaaggtg ctttatataa ttacacatat catatggcag actatcaggg tatacaaaat   1020
aaatattctg aaagaggtta tatattcaga caagttatac ctgtaattac agtaaatgaa   1080
gaaaataaaa tagtaaatat aatgtatgat attgttgaaa atgataaagt gcatatagaa   1140
aatattacta tagcaggaaa tacaaaaact aaagattttg ttatagaaag atatatagat   1200
ataaaacccg gagaagtatt caatactgca aaaatacaaa gagttcaaga gagattatat   1260
aatactcaat tctttgataa tattaattta ggagtaaaac ctggttctgc tgaaggactt   1320
atggaattaa atttaagtgt aactgaagga agaacagcta tggtatcagg aggaggcggt   1380
ttctccactg gttccggatt taaggtattt gcttctatta gagaaaataa cttcttagga   1440
agaggattgc agttaggatt aagcggagaa tttggagagc agcagaaacg tatagctgtt   1500
aactttgctg agccttattt acttaatctg cctatatatt tgggtgtgga tttatcatac   1560
ttcaatgaag gtgtaaacac tggttatcaa ataggaaccg atggtaattt tggtatacct   1620
aaatactcat actatactag acatggtttt gaaggtatag taagactagg ttattacttt   1680
gctgattatt attctacatt cataacattt gataccatag tacagcagta tcagcaatgg   1740
catgaccaag gagctactgc tgccggtcct aattatgttc ttagtgatat aaaaaaatat   1800
ttaactcata gagttaataa aaaagatgga tcattccaaa gatgggaaag tgattggttt   1860
acaacattca ttgtttcata ttctttactt agagatagca gaaacgatta tttgaaccct   1920
actagaggaa gtttcttgag aggtatggta gatttctatt ttggacacac ccagcttaca   1980
agattgagtg ctacaggatt cttggctgta cctgctacag aatggctgtc atttgcattc   2040
tatggagaat taggacaaat aattgctact cctggacttg ctttgcaaaa tgatgctgat   2100
gttctttatt atcttaaccc atttgaagat gtaaggggat gggatacttc caaatatact   2160
atatttaaga aaaacagagg attatcaact tatgatatgt taggagccaa cggttcagac   2220
```

```
ggtaaaccta ctactgactc ttggagttac ggtagagcaa aagtaagatt ctttgctgaa    2280
cttcgtatac ctataatacc taaaactctt ggattcgtta ctttccttga tgcaggacaa    2340
ttatggatgc catacagtac aggttggaat caggacggag atgctcattc atatccttct    2400
caatttatga atattaaaga tatatttgat ccttctcaat atatatattc tgtaggaata    2460
ggattcagac ttacaatacc tatattcaat ataagattct atattgctaa aagattcgtt    2520
tacaataaag aagatgttgg atttggtaaa ggatttcaag attttgaagg agatactttc    2580
actcctcttg gtgcttggtt cggaagagga tggggaattg catttactat gaaccaccca    2640
ttctat                                                                2646
```

<210> SEQ ID NO 42
<211> LENGTH: 882
<212> TYPE: PRT
<213> ORGANISM: Brachyspira hyodysenteriae

<400> SEQUENCE: 42

```
Val Glu Ile Leu Val Asn Phe Ile Lys Lys Asn Cys Ile Ile Leu Phe
 1               5                  10                  15

Ser Phe Leu Leu Leu Ala Ala Leu Leu Ile Ser Ala Glu Ser Asp
            20                  25                  30

Phe Glu Asn Leu Gln Thr Ala Arg Asn Ile Ala Val Tyr Glu Gly Leu
        35                  40                  45

Thr Ile Asn Arg Ile Asp Val Thr Gly Glu Val Arg Leu Thr Lys Glu
    50                  55                  60

Gln Ile Ile Asn Asn Phe Pro Ile Lys Ala Gly Ser Lys Phe Gln Arg
65                  70                  75                  80

Thr Glu Ile Asn Ala Ala Ile Lys Lys Leu Phe Asp Thr Gln Leu Phe
                85                  90                  95

Asp Arg Val Ala Ile Asp Ala Asn Arg Glu Asp Asp Gly Val Val Leu
            100                 105                 110

Asn Ile Val Val Ala Glu Arg Phe Ile Ile Lys Asp Ile Glu Tyr Ile
        115                 120                 125

Gly Asn Lys Arg Leu Ser Arg Thr Ala Leu Asn Asp Ala Val Lys Pro
    130                 135                 140

Ile Met Lys Ala Gly Asp Pro Tyr Ile Pro Gln Lys Leu Asn Asp Ala
145                 150                 155                 160

Val Asn Ala Ile Ile Thr Asn Tyr Gln Asp Lys Gly Tyr Leu Lys Ala
                165                 170                 175

Tyr Val Glu Pro Lys Val Ile Glu Asn Lys Asp Thr Ser Asp Val Leu
            180                 185                 190

Ile Gln Met Asn Ile Val Glu Gly Asn Glu Val Lys Val Ala Asn Ile
        195                 200                 205

Arg Phe His Gly Asn Thr His Phe Thr Asp Asn Glu Leu Lys Arg Gln
    210                 215                 220

Met Ser Thr Lys Glu Asn Gly Phe Met Thr Leu Gly Lys Phe Asn Glu
225                 230                 235                 240

Phe Thr Phe Asp Gly Asp Lys Asp Lys Ile Val Lys Tyr Tyr Ala Asp
                245                 250                 255

Arg Gly Tyr Tyr Arg Ala Lys Val Asp Asn Val Lys Phe Thr Tyr Gln
            260                 265                 270

Trp Arg Asn Pro Glu Ile Lys Asn Glu Gln Asp Leu Ile Ile Asp Ile
        275                 280                 285
```

-continued

Tyr Val Thr Glu Gly Asp Lys Tyr Tyr Phe Gly Asp Ile Gly Phe Lys
290                 295                 300

Gly Asn Phe Ile Ile Pro Ser Glu Asn Ile Gln Lys Asp Ile Lys Ser
305                 310                 315                 320

Lys Lys Gly Ala Leu Tyr Asn Tyr Thr Tyr His Met Ala Asp Tyr Gln
            325                 330                 335

Gly Ile Gln Asn Lys Tyr Ser Glu Arg Gly Tyr Ile Phe Arg Gln Val
            340                 345                 350

Ile Pro Val Ile Thr Val Asn Glu Asn Lys Ile Val Asn Ile Met
            355                 360                 365

Tyr Asp Ile Val Glu Asn Asp Lys Val His Ile Glu Asn Ile Thr Ile
370                 375                 380

Ala Gly Asn Thr Lys Thr Lys Asp Phe Val Ile Glu Arg Tyr Ile Asp
385                 390                 395                 400

Ile Lys Pro Gly Glu Val Phe Asn Thr Ala Lys Ile Gln Arg Val Gln
                405                 410                 415

Glu Arg Leu Tyr Asn Thr Gln Phe Phe Asp Asn Ile Asn Leu Gly Val
            420                 425                 430

Lys Pro Gly Ser Ala Glu Gly Leu Met Glu Leu Asn Leu Ser Val Thr
435                 440                 445

Glu Gly Arg Thr Ala Met Val Ser Gly Gly Gly Phe Ser Thr Gly
450                 455                 460

Ser Gly Phe Lys Val Phe Ala Ser Ile Arg Glu Asn Asn Phe Leu Gly
465                 470                 475                 480

Arg Gly Leu Gln Leu Gly Leu Ser Gly Glu Phe Gly Glu Gln Gln Lys
                485                 490                 495

Arg Ile Ala Val Asn Phe Ala Glu Pro Tyr Leu Leu Asn Leu Pro Ile
            500                 505                 510

Tyr Leu Gly Val Asp Leu Ser Tyr Phe Asn Glu Gly Val Asn Thr Gly
            515                 520                 525

Tyr Gln Ile Gly Thr Asp Gly Asn Phe Gly Ile Pro Lys Tyr Ser Tyr
530                 535                 540

Tyr Thr Arg His Gly Phe Glu Gly Ile Val Arg Leu Gly Tyr Tyr Phe
545                 550                 555                 560

Ala Asp Tyr Tyr Ser Thr Phe Ile Thr Phe Asp Thr Ile Val Gln Gln
                565                 570                 575

Tyr Gln Gln Trp His Asp Gln Gly Ala Thr Ala Gly Pro Asn Tyr
            580                 585                 590

Val Leu Ser Asp Ile Lys Lys Tyr Leu Thr His Arg Val Asn Lys Lys
595                 600                 605

Asp Gly Ser Phe Gln Arg Trp Glu Ser Asp Trp Phe Thr Thr Phe Ile
610                 615                 620

Val Ser Tyr Ser Leu Leu Arg Asp Ser Arg Asn Asp Tyr Leu Asn Pro
625                 630                 635                 640

Thr Arg Gly Ser Phe Leu Arg Gly Met Val Asp Phe Tyr Phe Gly His
                645                 650                 655

Thr Gln Leu Thr Arg Leu Ser Ala Thr Gly Phe Leu Ala Val Pro Ala
            660                 665                 670

Thr Glu Trp Leu Ser Phe Ala Phe Tyr Gly Glu Leu Gly Gln Ile Ile
            675                 680                 685

Ala Thr Pro Gly Leu Ala Leu Gln Asn Asp Ala Asp Val Leu Tyr Tyr
690                 695                 700

Leu Asn Pro Phe Glu Asp Val Arg Gly Trp Asp Thr Ser Lys Tyr Thr

```
              705                 710                 715                 720
Ile Phe Lys Lys Asn Arg Gly Leu Ser Thr Tyr Asp Met Leu Gly Ala
                    725                 730                 735

Asn Gly Ser Asp Gly Lys Pro Thr Thr Asp Ser Trp Ser Tyr Gly Arg
                740                 745                 750

Ala Lys Val Arg Phe Phe Ala Glu Leu Arg Ile Pro Ile Ile Pro Lys
                755                 760                 765

Thr Leu Gly Phe Val Thr Phe Leu Asp Ala Gly Gln Leu Trp Met Pro
            770                 775                 780

Tyr Ser Thr Gly Trp Asn Gln Asp Gly Asp Ala His Ser Tyr Pro Ser
785                 790                 795                 800

Gln Phe Met Asn Ile Lys Asp Ile Phe Asp Pro Ser Gln Tyr Ile Tyr
                    805                 810                 815

Ser Val Gly Ile Gly Phe Arg Leu Thr Ile Pro Ile Phe Asn Ile Arg
                820                 825                 830

Phe Tyr Ile Ala Lys Arg Phe Val Tyr Asn Lys Glu Asp Val Gly Phe
                835                 840                 845

Gly Lys Gly Phe Gln Asp Phe Glu Gly Asp Thr Phe Thr Pro Leu Gly
            850                 855                 860

Ala Trp Phe Gly Arg Gly Trp Gly Ile Ala Phe Thr Met Asn His Pro
865                 870                 875                 880

Phe Tyr

<210> SEQ ID NO 43
<211> LENGTH: 1308
<212> TYPE: DNA
<213> ORGANISM: Brachyspira hyodysenteriae

<400> SEQUENCE: 43
atgaaacgtt tatattttat tttatcagct ttattaataa ctgcttatag tgcatttagt      60
tatactgttg tagaagattt caatgatttt ttagttgatg aaaatcaatt aagaataagg     120
cttgacagat tcggagtatt ggcaggaaca gagaatttaa gatttatggt tggagtatca     180
ggagaaactg caggagtatt gcttgataat ttagacagag gtactaaagg aggaataaat     240
acattcagac cggcagcaat agcaggattt ggatataaaa cagaaagttt tggtataggt     300
gtaggttatc agtttaaata tatatcagga agctggcagt cgcatactcc tataataaca     360
gcaacagctt tgaatgataa cttgagaatc aatgtacctg ttacaatagg agtaggaagc     420
ggaaatgtta atgacggaga tatagcagtt tcaacagata ctagaataga atattataca     480
ggaaacaata tattcagcag aataagagtt aatcttaaat atggtatgta tagattaaaa     540
gctaatgaaa gcagaagcgg agatttgaca ggaagcggaa atataaatat gggtactgta     600
agtggaactg taggcgagaa tggtaaatat ggatttctta agatactac agcacattct     660
ataggaatag atgtaagagg ttatttata gcggcaacag atcctgtatt agtagagcct     720
cagataagag tattatatca aggttctata gcggatttta caggtacttc atataaagta     780
acaacaccca ctgaactaa agaaggagga gcaggattcg gactctataa tatagatgct     840
tcaaatccta taggtgcttt ttcaataggt gatacaggtt caatacaatc agtgccttat     900
tatgatttta ctgctcataa tatatgtttt acaggtgaag agcttcaat agagatagga     960
ggtacagaat attatcttac aaagccgcag ttttaggaa atccgttcc tgtgggttt    1020
actgctgaaa gtgagtttat tacattgtat ttggagcctg ctttatcatt ctctatgatt    1080
acaggaggaa ttaattctta tgcaagcagt gctaagcctg taagaatacc gcctttattt    1140
```

-continued

```
tattcggttg gatatttggt atatggagaa ttatatataa ctcctaaacc taatttagaa    1200
tggtattttg aggctcagat tggaagtgct acaactattg atagtatagg agatagtaaa    1260
cagggaggtt tagctttcaa tggaagtacc ggtatcactt ggaagttt                1308
```

<210> SEQ ID NO 44
<211> LENGTH: 436
<212> TYPE: PRT
<213> ORGANISM: Brachyspira hyodysenteriae

<400> SEQUENCE: 44

```
Met Lys Arg Leu Tyr Phe Ile Leu Ser Ala Leu Leu Ile Thr Ala Tyr
 1               5                   10                  15

Ser Ala Phe Ser Tyr Thr Val Val Glu Asp Phe Asn Asp Phe Leu Val
                20                  25                  30

Asp Glu Asn Gln Leu Arg Ile Arg Leu Asp Arg Phe Gly Val Leu Ala
            35                  40                  45

Gly Thr Glu Asn Leu Arg Phe Met Val Gly Val Ser Gly Glu Thr Ala
        50                  55                  60

Gly Val Leu Leu Asp Asn Leu Asp Arg Gly Thr Lys Gly Gly Ile Asn
    65                  70                  75                  80

Thr Phe Arg Pro Ala Ala Ile Ala Gly Phe Gly Tyr Lys Thr Glu Ser
                85                  90                  95

Phe Gly Ile Gly Val Gly Tyr Gln Phe Lys Tyr Ile Ser Gly Ser Trp
            100                 105                 110

Gln Ser His Thr Pro Ile Ile Thr Ala Thr Ala Leu Asn Asp Asn Leu
        115                 120                 125

Arg Ile Asn Val Pro Val Thr Ile Gly Val Gly Ser Gly Asn Val Asn
    130                 135                 140

Asp Gly Asp Ile Ala Val Ser Thr Asp Thr Arg Ile Glu Tyr Tyr Thr
145                 150                 155                 160

Gly Asn Asn Ile Phe Ser Arg Ile Arg Val Asn Leu Lys Tyr Gly Met
                165                 170                 175

Tyr Arg Leu Lys Ala Asn Glu Ser Arg Ser Gly Asp Leu Thr Gly Ser
            180                 185                 190

Gly Asn Ile Asn Met Gly Thr Val Ser Gly Thr Val Gly Glu Asn Gly
        195                 200                 205

Lys Tyr Gly Phe Leu Lys Asp Thr Thr Ala His Ser Ile Gly Ile Asp
    210                 215                 220

Val Arg Gly Tyr Phe Ile Ala Ala Thr Asp Pro Val Leu Val Glu Pro
225                 230                 235                 240

Gln Ile Arg Val Leu Tyr Gln Gly Ser Ile Ala Asp Phe Thr Gly Thr
                245                 250                 255

Ser Tyr Lys Val Thr Thr Pro Thr Gly Thr Lys Glu Gly Gly Ala Gly
            260                 265                 270

Phe Gly Leu Tyr Asn Ile Asp Ala Ser Asn Pro Ile Gly Ala Phe Ser
        275                 280                 285

Ile Gly Asp Thr Gly Ser Ile Gln Ser Val Pro Tyr Tyr Asp Phe Thr
    290                 295                 300

Ala His Asn Ile Met Phe Thr Gly Glu Gly Ala Ser Ile Glu Ile Gly
305                 310                 315                 320

Gly Thr Glu Tyr Tyr Leu Thr Lys Pro Gln Phe Leu Gly Ile Ser Val
                325                 330                 335

Pro Val Gly Phe Thr Ala Glu Ser Glu Phe Ile Thr Leu Tyr Leu Glu
```

```
                    340               345               350
Pro Ala Leu Ser Phe Ser Met Ile Thr Gly Gly Ile Asn Ser Tyr Ala
                355               360               365

Ser Ser Ala Lys Pro Val Arg Ile Pro Pro Leu Phe Tyr Ser Val Gly
            370               375               380

Tyr Leu Val Tyr Gly Glu Leu Tyr Ile Thr Pro Lys Pro Asn Leu Glu
385               390               395               400

Trp Tyr Phe Glu Ala Gln Ile Gly Ser Ala Thr Thr Ile Asp Ser Ile
                405               410               415

Gly Asp Ser Lys Gln Gly Gly Leu Ala Phe Asn Gly Ser Thr Gly Ile
            420               425               430

Thr Trp Lys Phe
        435

<210> SEQ ID NO 45
<211> LENGTH: 2367
<212> TYPE: DNA
<213> ORGANISM: Brachyspira hyodysenteriae

<400> SEQUENCE: 45
atgaaatata aacctacaag caggaaagaa ttaaaagatt tagtaacaga tgaaagtatt      60
tatttgggtg atattgatac tagcttaata actgatatgt caaacttatt tgattttttt    120
aatagagata attatgacgg tatagaaaat tgggatactt ctaatgtaga aaatatggct    180
ggtatgtttt ctgctaatag gaattttaat aaagatatta gtaaatggaa tgtatctaaa    240
gtgaaaaata cagcttatat gttttcttg gctgaaaaat ttaatcagcc tttgaatgat    300
tgggacgtta gtaatgtaat aaatatgaat agcatgttta tgaatgctaa aagttttaat    360
cagcctatta ataattggaa tgtaagtaaa gttcaaagta tgagcaatat gtttaatcgt    420
gccgaaagtt ttaatcaaaa tataaatgat tggaatgtaa gtaatgtaga aaatatgaat    480
catatgtttt catctgccta taaattcaat cagccttat ttaaatggga tacttctaaa    540
gtaaaagaga tggctggtat gttttcatta gcttatgcat ttaatcagcc tcttaacaat    600
tggaatgtaa gcaatgttac taatatgagg tgcatgttta tgtttgcaag agattttaat    660
aagcctatta ataattggaa tacaaaaaaa ttaaaagatg caggaagtat gttctcaaat    720
acatcggcat tcaatcagaa tttagatgat tggaatattg ataatctttc agatatgagt    780
aattttaata agattctaa attagaatta acatttaaat tcaaaattta tttatatgct    840
ttaactttag aaaaagaaga aaaaaataat ttacatgatt ttataaaaaa caatgtaaaa    900
aagatatatg aaattataga aaatcataaa acaagaagg ttaatcttct aaaagatat    960 ttaataaata atttttatag tgaattaaaa gaattaatac cagattatat tgaaagtttt   1020
aatagcatag aagaagttta taattatata gacaaaaatt ataataaaaa agatgataaa   1080
aaagtaaaat ttatagatga tataaaaatt gaaatatag ataaagaat aataaaatat   1140 atttacttat catatttaga attaaaaaga gaagcctaca gaataaagca aatagattat   1200
attataaatt taattgataa aaaatctttt ataaatgcaa ttaaaacgat atacacaagc   1260
accaataaag aaacatctct aattatgtac ggaatatacg gaggagatga ggcattaaga   1320
gagatttaca aaaagaaaa agattcaaaa ttatgtttac ttgtatttc tatcaataaa   1380 aacagtaaat atgctattaa tatgctttat aatgtattta agaaaagtaa aaatatgaa   1440 gtaaagagag cagcagaaaa aattattgag gatatagcaa agaaaataa tttgagcgtt   1500 tatgaatttg gattaaaaac tataccaaat tttggattca atataaacgg tgaaaaaata   1560
```

```
ataaataata atcaatataa aataattttg aaaaacgatt atactataga gttttttgat    1620
atcaaagaaa ataaaatatt aaagcaaata cctaaatatt ttgataatag taccaaagaa    1680
gaaattaaat atataaaaac agaaattcca aatattataa aaaatcaaag cagaaattta    1740
ataaaaattt tattaacagg taaaaagtac tatttcaatt tttttaaaga aatatttatt    1800
gataatccaa taatgaataa atttgcaatt aatttagttt ggaatttatt tgatgaaaat    1860
aacaatttta taacgacatt taggtattca ggcgacggaa gttatacaaa ctacgatgat    1920
aatacagtga atataaatga taattatttt gtaagtttat caagccctat agaaatggaa    1980
gaaaaaatta tatcaaaatg gaaaaaacat cttgaagatt atgaattatc acagcctata    2040
atgcagttta caaatataaa aataaataat ttagaagaag cattaaaaaa attagaaaat    2100
atagaaataa gctacggtac aataaaagca ttttctcaaa agtatgatat gaatactgaa    2160
tgtaaaagct attacgaaat taacggatat tcatttgaag actcatacaa taatcaagat    2220
ttttatataa gaacaaaaat tatcaatact gaaaccaatt ataatgataa aataaaaatt    2280
aatatagagt ttaacaatgc tagcaacaga tttatatata cttggcttat acttttaata    2340 tgggattttta gattaactga aatattt                                      2367

<210> SEQ ID NO 46
<211> LENGTH: 789
<212> TYPE: PRT
<213> ORGANISM: Brachyspira hyodysenteriae

<400> SEQUENCE: 46

Met Lys Tyr Lys Pro Thr Ser Arg Lys Glu Leu Lys Asp Leu Val Thr
 1               5                  10                  15

Asp Glu Ser Ile Tyr Leu Gly Asp Ile Asp Thr Ser Leu Ile Thr Asp
             20                  25                  30

Met Ser Asn Leu Phe Asp Phe Asn Arg Asp Asn Tyr Asp Gly Ile
         35                  40                  45

Glu Asn Trp Asp Thr Ser Asn Val Glu Asn Met Ala Gly Met Phe Ser
     50                  55                  60

Ala Asn Arg Asn Phe Asn Lys Asp Ile Ser Lys Trp Asn Val Ser Lys
 65                  70                  75                  80

Val Lys Asn Thr Ala Tyr Met Phe Phe Leu Ala Glu Lys Phe Asn Gln
                 85                  90                  95

Pro Leu Asn Asp Trp Asp Val Ser Asn Val Ile Asn Met Asn Ser Met
            100                 105                 110

Phe Met Asn Ala Lys Ser Phe Asn Gln Pro Ile Asn Asn Trp Asn Val
        115                 120                 125

Ser Lys Val Gln Ser Met Ser Asn Met Phe Asn Arg Ala Glu Ser Phe
    130                 135                 140

Asn Gln Asn Ile Asn Asp Trp Asn Val Ser Val Glu Asn Met Asn
145                 150                 155                 160

His Met Phe Ser Ser Ala Tyr Lys Phe Asn Gln Pro Leu Phe Lys Trp
                165                 170                 175

Asp Thr Ser Lys Val Lys Glu Met Ala Gly Met Phe Ser Leu Ala Tyr
            180                 185                 190

Ala Phe Asn Gln Pro Leu Asn Asn Trp Asn Val Ser Asn Val Thr Asn
        195                 200                 205

Met Arg Cys Met Phe Met Phe Ala Arg Asp Phe Asn Lys Pro Ile Asn
    210                 215                 220
```

-continued

```
Asn Trp Asn Thr Lys Lys Leu Lys Asp Ala Gly Ser Met Phe Ser Asn
225                 230                 235                 240

Thr Ser Ala Phe Asn Gln Asn Leu Asp Asp Trp Asn Ile Asp Asn Leu
            245                 250                 255

Ser Asp Met Ser Asn Phe Asn Lys Asp Ser Lys Leu Glu Leu Thr Phe
        260                 265                 270

Lys Phe Lys Ile Tyr Leu Tyr Ala Leu Thr Leu Glu Lys Glu Glu Lys
    275                 280                 285

Asn Asn Leu His Asp Phe Ile Lys Asn Asn Val Lys Lys Ile Tyr Glu
290                 295                 300

Ile Ile Glu Asn His Lys Asn Lys Lys Val Asn Leu Leu Lys Arg Tyr
305                 310                 315                 320

Leu Ile Asn Asn Phe Tyr Ser Glu Leu Lys Glu Leu Ile Pro Asp Tyr
                325                 330                 335

Ile Glu Ser Phe Asn Ser Ile Glu Glu Val Tyr Asn Tyr Ile Asp Lys
            340                 345                 350

Asn Tyr Asn Lys Lys Asp Asp Lys Lys Val Lys Phe Ile Asp Asp Ile
            355                 360                 365

Lys Ile Glu Asn Ile Asp Lys Arg Ile Lys Tyr Ile Tyr Leu Ser
370                 375                 380

Tyr Leu Glu Leu Lys Arg Glu Ala Tyr Arg Ile Lys Gln Ile Asp Tyr
385                 390                 395                 400

Ile Ile Asn Leu Ile Asp Lys Lys Ser Phe Ile Asn Ala Ile Lys Thr
                405                 410                 415

Ile Tyr Thr Ser Thr Asn Lys Glu Thr Ser Leu Ile Met Tyr Gly Ile
            420                 425                 430

Tyr Gly Gly Asp Glu Ala Leu Arg Glu Ile Tyr Lys Lys Glu Lys Asp
        435                 440                 445

Ser Lys Leu Cys Leu Leu Val Phe Ser Ile Asn Lys Asn Ser Lys Tyr
    450                 455                 460

Ala Ile Asn Met Leu Tyr Asn Val Phe Lys Lys Ser Lys Lys Tyr Glu
465                 470                 475                 480

Val Lys Glu Thr Ala Glu Lys Ile Ile Glu Asp Ile Ala Lys Glu Asn
                485                 490                 495

Asn Leu Ser Val Tyr Glu Phe Gly Leu Lys Thr Ile Pro Asn Phe Gly
            500                 505                 510

Phe Asn Ile Asn Gly Glu Lys Ile Ile Asn Asn Gln Tyr Lys Ile
        515                 520                 525

Ile Leu Lys Asn Asp Tyr Thr Ile Glu Phe Phe Asp Ile Lys Glu Asn
530                 535                 540

Lys Ile Leu Lys Gln Ile Pro Lys Tyr Phe Asp Asn Ser Thr Lys Glu
545                 550                 555                 560

Glu Ile Lys Tyr Ile Lys Thr Glu Ile Pro Asn Ile Ile Lys Asn Gln
                565                 570                 575

Ser Arg Asn Leu Ile Lys Ile Leu Leu Thr Gly Lys Lys Tyr Tyr Phe
            580                 585                 590

Asn Phe Phe Lys Glu Ile Phe Ile Asp Asn Pro Ile Met Asn Lys Phe
        595                 600                 605

Ala Ile Asn Leu Val Trp Asn Leu Phe Asp Glu Asn Asn Phe Ile
        610                 615                 620

Thr Thr Phe Arg Tyr Ser Gly Asp Gly Ser Tyr Thr Asn Tyr Asp Asp
625                 630                 635                 640

Asn Thr Val Asn Ile Asn Asp Asn Tyr Phe Val Ser Leu Ser Ser Pro
```

```
                      645                 650                 655
Ile Glu Met Glu Glu Lys Ile Ile Ser Lys Trp Lys Lys His Leu Glu
                660                 665                 670

Asp Tyr Glu Leu Ser Gln Pro Ile Met Gln Phe Thr Asn Ile Lys Ile
            675                 680                 685

Asn Asn Leu Glu Glu Ala Leu Lys Lys Leu Glu Asn Ile Glu Ile Ser
        690                 695                 700

Tyr Gly Thr Ile Lys Ala Phe Ser Gln Lys Tyr Asp Met Asn Thr Glu
705                 710                 715                 720

Cys Lys Ser Tyr Tyr Glu Ile Asn Gly Tyr Ser Phe Glu Asp Ser Tyr
                725                 730                 735

Asn Asn Gln Asp Phe Tyr Ile Arg Thr Lys Ile Ile Asn Thr Glu Thr
            740                 745                 750

Asn Tyr Asn Asp Lys Ile Lys Ile Asn Ile Glu Phe Asn Asn Ala Ser
        755                 760                 765

Asn Arg Phe Ile Tyr Thr Trp Leu Ile Leu Leu Ile Trp Asp Phe Arg
770                 775                 780

Leu Thr Glu Ile Phe
785

<210> SEQ ID NO 47
<211> LENGTH: 729
<212> TYPE: DNA
<213> ORGANISM: Brachyspira hyodysenteriae

<400> SEQUENCE: 47
atgataaaaa aaattttaac tttaatcttt gtattaattt tggcagcttc atgttctact      60
aatgataaac atgttgtagt attagctttt agtaaacagc ttcatgctgt actttataat    120
gataatagtc agtctacaaa aacagcatca aaaacatata tacaaaaaga tgatattaca    180
actgtagcag atcctataaa agaaaaaaaa gaatatacaa atactcaagc acaagtaagt    240 aaaaagcag aagaaaaaaa agaagaactt acaaataacg atgctttaga agaagaaaaa     300
cctcaagtta taaagcaaac tgaggttata cagaaagatg ataatgagat tcttcttact    360
gcaaatataa tatcttttga ttttgattct tatgaattaa aaaatgaata taatgaaggg    420
atagatgaaa tttgcaaata tttaaataat aatcgagata ttaatctaat aatagaagga    480
catagcgaca gtataggga ctcaaattat aatatatatt tatctgaaaa cagagcaaaa      540
gcgatatttg ataaattagt agataaagga atagataaag atagacttag atatataggga    600 tatggctcta ctcattcatc tgagtataat gataaagaca gaaatgcca atttgttata     660 ataaataatt cagatgaaga gcaggaatac aaaaaagaaa acgaaactga tattatcaaa    720
ttaaaacaa                                                           729

<210> SEQ ID NO 48
<211> LENGTH: 243
<212> TYPE: PRT
<213> ORGANISM: Brachyspira hyodysenteriae

<400> SEQUENCE: 48

Met Ile Lys Lys Ile Leu Thr Leu Ile Phe Val Leu Ile Leu Ala Ala
1               5                   10                  15

Ser Cys Ser Thr Asn Asp Lys His Val Val Val Leu Ala Phe Ser Lys
                20                  25                  30

Gln Leu His Ala Val Leu Tyr Asn Asp Asn Ser Gln Ser Thr Lys Thr
            35                  40                  45
```

```
Ala Ser Lys Thr Tyr Ile Gln Lys Asp Asp Ile Thr Thr Val Ala Asp
    50                  55                  60

Pro Ile Lys Glu Lys Glu Tyr Thr Asn Thr Gln Ala Gln Val Ser
65                  70                  75                  80

Lys Lys Ala Glu Glu Lys Lys Glu Glu Leu Thr Asn Asn Asp Ala Leu
                85                  90                  95

Glu Glu Glu Lys Pro Gln Val Ile Lys Gln Thr Glu Val Ile Gln Lys
            100                 105                 110

Asp Asp Asn Glu Ile Leu Leu Thr Ala Asn Ile Ile Ser Phe Asp Phe
        115                 120                 125

Asp Ser Tyr Glu Leu Lys Asn Glu Tyr Asn Glu Gly Ile Asp Glu Ile
    130                 135                 140

Cys Lys Tyr Leu Asn Asn Asn Arg Asp Ile Asn Leu Ile Ile Glu Gly
145                 150                 155                 160

His Ser Asp Ser Ile Gly Asp Ser Asn Tyr Asn Ile Tyr Leu Ser Glu
                165                 170                 175

Asn Arg Ala Lys Ala Ile Phe Asp Lys Leu Val Asp Lys Gly Ile Asp
            180                 185                 190

Lys Asp Arg Leu Arg Tyr Ile Gly Tyr Gly Ser Thr His Ser Ser Glu
        195                 200                 205

Tyr Asn Asp Lys Asp Arg Lys Cys Gln Phe Val Ile Ile Asn Asn Ser
    210                 215                 220

Asp Glu Glu Gln Glu Tyr Lys Lys Glu Asn Glu Thr Asp Ile Ile Lys
225                 230                 235                 240

Leu Lys Gln
```

<210> SEQ ID NO 49
<211> LENGTH: 969
<212> TYPE: DNA
<213> ORGANISM: Brachyspira hyodysenteriae

<400> SEQUENCE: 49

```
atgaaaaaaa ttattttatt aatatttata ttattaaata tatcatgcag aaatatcatt      60
acaatagcag aaaataaaaa aaatatagat aatgtaaata atgtacatat agaagaaaat     120
gaatacttat atgctcttga aatagataaa gccaatcctc aaaatatgga agaagcatta     180
aaaagatatg cagcagatca taatggaaaa tataaattaa tattcacagg tacatcaaca     240
aaaaaatatg atgtttggac ttcaataagt caaatgcttg aagatatttc tttaaaaaac     300
ataaaaatag aaatatcgat tgtaaatgta attttttccaa atggtaaaat acctgatttt     360
ttatttggag gaaatgctgt aaataaatca atagtaaaaa taacatttcc aaatagcata     420
actgaaaatag gcgaatacag tatttttttgt ccagaattaa cggaaataac acttccaagt     480
aatttaagaa caataggcag aagaggatta ataggatgcg aaagtttaaa aatactgaaa     540
cttcctaatt cattaaaaac aataggagaa ttatcattaa atggatgcgg atttgccagt     600
attgtaattc ctgattctgt aacttctata ggtaaaagtg cttttgccga ttgtgagaat     660
ttagtaaata taaaattacc aaataattta gaaacaatac tgatagtat gcttgaaagc     720
tgcggatcca ttaatacaat aactatacca gcatctgtaa aaaaaataga aaattctgta     780
ttttttttact gcaaaaactt tgaaaacatt agattttttaa atggtaatct tcaatcaatg     840
acagtaggaa aagatatatt tgcaggctgc cctttaaaaa atgtttatat acctaaaaac     900
agcagtgcat cagatgaaga atggagaaat actttaggca ttaaatcaac tgtaaagatt     960
```

```
                                                                   969
ataagagaa
```

<210> SEQ ID NO 50
<211> LENGTH: 323
<212> TYPE: PRT
<213> ORGANISM: Brachyspira hyodysenteriae

<400> SEQUENCE: 50

```
Met Lys Lys Ile Ile Leu Leu Ile Phe Ile Leu Leu Asn Ile Ser Cys
 1               5                  10                  15

Arg Asn Ile Ile Thr Ile Ala Glu Asn Lys Lys Asn Ile Asp Asn Val
            20                  25                  30

Asn Asn Val His Ile Glu Glu Asn Glu Tyr Leu Tyr Ala Leu Glu Ile
        35                  40                  45

Asp Lys Ala Asn Pro Gln Asn Met Glu Glu Ala Leu Lys Arg Tyr Ala
    50                  55                  60

Ala Asp His Asn Gly Lys Tyr Lys Leu Ile Phe Thr Gly Thr Ser Thr
65                  70                  75                  80

Lys Lys Tyr Asp Val Trp Thr Ser Ile Ser Gln Met Leu Glu Asp Ile
                85                  90                  95

Ser Leu Lys Asn Ile Lys Ile Glu Ile Ser Ile Val Asn Val Ile Phe
            100                 105                 110

Pro Asn Gly Lys Ile Pro Asp Phe Leu Phe Gly Gly Asn Ala Val Asn
        115                 120                 125

Lys Ser Ile Val Lys Ile Thr Phe Pro Asn Ser Ile Thr Glu Ile Gly
    130                 135                 140

Glu Tyr Ser Ile Phe Cys Pro Glu Leu Thr Glu Ile Thr Leu Pro Ser
145                 150                 155                 160

Asn Leu Arg Thr Ile Gly Arg Arg Gly Leu Ile Gly Cys Glu Ser Leu
                165                 170                 175

Lys Ile Leu Lys Leu Pro Asn Ser Leu Lys Thr Ile Gly Glu Leu Ser
            180                 185                 190

Leu Asn Gly Cys Gly Phe Ala Ser Ile Val Ile Pro Asp Ser Val Thr
        195                 200                 205

Ser Ile Gly Lys Ser Ala Phe Ala Asp Cys Gly Asn Leu Val Asn Ile
    210                 215                 220

Lys Leu Pro Asn Asn Leu Glu Thr Ile Pro Asp Ser Met Leu Glu Ser
225                 230                 235                 240

Cys Gly Ser Ile Asn Thr Ile Thr Ile Pro Ala Ser Val Lys Lys Ile
                245                 250                 255

Glu Asn Ser Val Phe Phe Tyr Cys Lys Asn Phe Glu Asn Ile Arg Phe
            260                 265                 270

Leu Asn Gly Asn Leu Gln Ser Met Thr Val Gly Lys Asp Ile Phe Ala
        275                 280                 285

Gly Cys Pro Leu Lys Asn Val Tyr Ile Pro Lys Asn Ser Ser Ala Ser
    290                 295                 300

Asp Glu Glu Trp Arg Asn Thr Leu Gly Ile Lys Ser Thr Val Lys Ile
305                 310                 315                 320

Ile Arg Glu
```

<210> SEQ ID NO 51
<211> LENGTH: 564
<212> TYPE: DNA
<213> ORGANISM: Brachyspira hyodysenteriae

<400> SEQUENCE: 51

```
atgcatattt ctggtgattc tcctttagat aggaaagttg gagatgctag ttattatttt    60
gctactgttc aacattgctg ggggtgggct acttggaaaa gagcttggaa atattttgat   120
gtaactatgg aaagtataaa ttttgaagat gtaaaaaaaa caattagaaa agatacaaa    180 gattttaata taaagattact ctggcaaaga tggtttccta gaataaaaaa agagcattct   240
tctgtatggg attatcaatg gacttactgt attatctcaa aaaatggaat atgcattaat   300
ccaagtataa atttaacttc taatatagga tttggagaag attctaccca cactacaaat   360
gaaaatgatg aaaatataaa tagtaaaaca taccctatgg atactgaaaa tattattcat   420
cctaaagaaa taaatgtgat gaaagagct gattttgaaa tagctattaa agatttaat    480 ataaaaccttt ctctttaac atctaatata accagagaag ttaaaagaat tataaaacaa   540
ataaaaaact tatttatcaa aaaa                                          564
```

<210> SEQ ID NO 52
<211> LENGTH: 188
<212> TYPE: PRT
<213> ORGANISM: Brachyspira hyodysenteriae

<400> SEQUENCE: 52

```
Met His Ile Ser Gly Asp Ser Pro Leu Asp Arg Lys Val Gly Asp Ala
1               5                   10                  15

Ser Tyr Tyr Phe Ala Thr Val Gln His Cys Trp Gly Trp Ala Thr Trp
            20                  25                  30

Lys Arg Ala Trp Lys Tyr Phe Asp Val Thr Met Glu Ser Ile Asn Phe
        35                  40                  45

Glu Asp Val Lys Lys Thr Ile Arg Lys Arg Tyr Lys Asp Phe Asn Ile
    50                  55                  60

Lys Asp Tyr Trp Gln Arg Trp Phe Pro Arg Ile Lys Lys Glu His Ser
65                  70                  75                  80

Ser Val Trp Asp Tyr Gln Trp Thr Tyr Cys Ile Ile Ser Lys Asn Gly
                85                  90                  95

Ile Cys Ile Asn Pro Ser Ile Asn Leu Thr Ser Asn Ile Gly Phe Gly
            100                 105                 110

Glu Asp Ser Thr His Thr Thr Asn Glu Asn Asp Glu Asn Ile Asn Ser
        115                 120                 125

Lys Thr Tyr Pro Met Asp Thr Glu Asn Ile Ile His Pro Lys Glu Ile
    130                 135                 140

Lys Cys Asp Glu Arg Ala Asp Phe Glu Ile Ala Ile Lys Arg Phe Asn
145                 150                 155                 160

Ile Lys Pro Phe Ser Leu Thr Ser Asn Ile Thr Arg Glu Val Lys Arg
                165                 170                 175

Ile Ile Lys Gln Ile Lys Asn Leu Phe Ile Lys Lys
            180                 185
```

<210> SEQ ID NO 53
<211> LENGTH: 396
<212> TYPE: DNA
<213> ORGANISM: Brachyspira hyodysenteriae

<400> SEQUENCE: 53

```
atgtttaata ctcctatatt attaattatt tttaaaagaa aatatactgc attaaaagtt    60
ttagatacaa taagaaatgt aaaacccaaa aaattatata tagcagctga tggctggaga   120
aatgaagaag aaaaaacaaa atgtattgat acaagagaag ctgtattaga agctgtagat   180
```

```
tgggaatgcg aagtaaaaac tttatttcaa gataaaaatt taggatgctg ttatggtcct    240
gtaaatgctg taaattggtt atttgaaaat gaagaacaag gaataatact tgaagatgat    300
gttatagctg aaacttcttt ttttattatt gcgagaaatt acttaactat tataaagata    360
atgaaaaaat tatgcatatt tctggtgatt ctcctt                              396
```

<210> SEQ ID NO 54
<211> LENGTH: 132
<212> TYPE: PRT
<213> ORGANISM: Brachyspira hyodysenteriae

<400> SEQUENCE: 54

```
Met Phe Asn Thr Pro Ile Leu Leu Ile Ile Phe Lys Arg Lys Tyr Thr
1               5                   10                  15

Ala Leu Lys Val Leu Asp Thr Ile Arg Asn Val Lys Pro Lys Lys Leu
            20                  25                  30

Tyr Ile Ala Ala Asp Gly Trp Arg Asn Glu Glu Lys Thr Lys Cys
        35                  40                  45

Ile Asp Thr Arg Glu Ala Val Leu Glu Ala Val Asp Trp Glu Cys Glu
    50                  55                  60

Val Lys Thr Leu Phe Gln Asp Lys Asn Leu Gly Cys Cys Tyr Gly Pro
65                  70                  75                  80

Val Asn Ala Val Asn Trp Leu Phe Glu Asn Glu Gln Gly Ile Ile
                85                  90                  95

Leu Glu Asp Asp Val Ile Ala Glu Thr Ser Phe Phe Ile Ile Ala Arg
            100                 105                 110

Asn Tyr Leu Thr Ile Ile Lys Ile Met Lys Lys Leu Cys Ile Phe Leu
        115                 120                 125

Val Ile Leu Leu
    130
```

<210> SEQ ID NO 55
<211> LENGTH: 825
<212> TYPE: DNA
<213> ORGANISM: Brachyspira hyodysenteriae

<400> SEQUENCE: 55

```
atgaatgata ttattaaagt gataaatata ttaaacgata taccagaacc ttttctgta     60 gatggaataa taaaaacttt tgaagcaagc tctaaagatt ttataaaaag ttttgctgtt   120 tattttata aggaaggcag tgaagaagca agattatggt atacatctaa aaataaatta   180
gttattaatg ataaaaaaaa taatagagaa tatactctat tgccagagg taataaattt   240 ggttatataa tagttaatgc agataaaaat aaagatgaaa tggaagtact tattaattat   300
ctatcaataa tattatatag tgaaaaactt tcattttgg caaatagaga caaacttaca   360
ggtttataca atcgcggata taataaaaa tatttgcagg agaaagaaac tacaaatgaa   420
atatattcta tagtaatagt agatttagat aaattcaaac attataatga tacttacgga   480
cataatatag gagatcatgt attaaaatta atttcaaagg taatgaaaga ttctttaaaa   540
aatataaaat ataaatctgt attggcaaga tatggaggag aagaattat tatagtaatt   600 gatgttaata taaaaatga tctttttaat gctatggaag aaataagaaa ctcaataata   660
gaaactgatt tatctacaga agaatattct ctaaaagcaa cagcatcttt aggaggtgct   720
ataaaagagg aaaatacaac tttaagaact tttataaata agcagatca atcattatat   780 aatgccaaag aaacaggaag aaataaatcc gttatattag atttt                   825
```

<210> SEQ ID NO 56
<211> LENGTH: 275
<212> TYPE: PRT
<213> ORGANISM: Brachyspira hyodysenteriae

<400> SEQUENCE: 56

Met Asn Asp Ile Ile Lys Val Ile Asn Ile Leu Asn Asp Ile Pro Glu
1               5                   10                  15

Pro Phe Ser Val Asp Gly Ile Ile Lys Thr Phe Glu Ala Ser Ser Lys
            20                  25                  30

Asp Phe Ile Lys Ser Phe Ala Val Tyr Phe Tyr Lys Glu Gly Ser Glu
        35                  40                  45

Glu Ala Arg Leu Trp Tyr Thr Ser Lys Asn Lys Leu Val Ile Asn Asp
    50                  55                  60

Lys Lys Asn Asn Arg Glu Tyr Thr Leu Phe Ala Arg Gly Asn Lys Phe
65                  70                  75                  80

Gly Tyr Ile Ile Val Asn Ala Asp Lys Asn Lys Asp Glu Met Glu Val
                85                  90                  95

Leu Ile Asn Tyr Leu Ser Ile Ile Leu Tyr Ser Glu Lys Leu Ser Phe
            100                 105                 110

Leu Ala Asn Arg Asp Lys Leu Thr Gly Leu Tyr Asn Arg Gly Tyr Ile
        115                 120                 125

Ile Lys Tyr Leu Gln Glu Lys Glu Thr Thr Asn Glu Ile Tyr Ser Ile
    130                 135                 140

Val Ile Val Asp Leu Asp Lys Phe Lys His Tyr Asn Asp Thr Tyr Gly
145                 150                 155                 160

His Asn Ile Gly Asp His Val Leu Lys Leu Ile Ser Lys Val Met Lys
                165                 170                 175

Asp Ser Leu Lys Asn Ile Lys Tyr Lys Ser Val Leu Ala Arg Tyr Gly
            180                 185                 190

Gly Glu Glu Phe Ile Ile Val Ile Asp Val Asn Asn Lys Asn Asp Leu
        195                 200                 205

Phe Asn Ala Met Glu Glu Ile Arg Asn Ser Ile Ile Glu Thr Asp Leu
    210                 215                 220

Ser Thr Glu Glu Tyr Ser Leu Lys Ala Thr Ala Ser Leu Gly Gly Ala
225                 230                 235                 240

Ile Lys Glu Glu Asn Thr Thr Leu Arg Thr Phe Ile Asn Lys Ala Asp
                245                 250                 255

Gln Ser Leu Tyr Asn Ala Lys Glu Thr Gly Arg Asn Lys Ser Val Ile
            260                 265                 270

Leu Asp Phe
        275

<210> SEQ ID NO 57
<211> LENGTH: 1815
<212> TYPE: DNA
<213> ORGANISM: Brachyspira hyodysenteriae

<400> SEQUENCE: 57
atgaaaaata tttttaaata tgcttccatt ataggatgca cttttgcctc gcttaatttt      60
gcggctgatt atatagatta taaagtaaaa aacggcgata ctttatttgg aatagctttc     120
gctcatgata tgagtgcaaa tgaattttta aagttaata atataaaaga tcctgataaa     180
tataatctta gagtaggaga aactttaaaa gtaaaagata aaggttatac tcttgtatat     240
gactctgata taaagttttt cggcttgaaa ggagaagaag gaaactcata caaagattat     300

-continued

```
aaagtaaaaa acggggatac tttatttggt atagcatttg cccatggaat gactgctaat    360
gaatttctag ctataaataa tattaaagat gccaataaat ataatcttag agtaggacaa    420
actcttaaag tagcaaataa tcaaaaagaa aataatgctt cttcaaataa tataaataat    480
agtgataata cagaaaatta tgatacttat aaagtgcaaa gcggtgatac tttatacgga    540
atagctttct ctcatggtat gacagcaagc gaatttttaa agattaataa tatagatgat    600
cctgataaat ataaactata tgtaggtaaa actatgtatg ttaaatcatc taaaaaagaa    660
aataatttaa acacaaataa tgaaaaagat acaggaaaag aaatagaata ctatactgta    720
aaaagcggcg ataccttata cggaatagct tttcaaaatg atattagcgt aaatgatttt    780
ctaagaatta acaatataga tgatccttta aaatacaaat taagaacagg cgaaaaatta    840
aaaatatatg caagagaaaa tgcctcaaat acacaaagca aaactataaa aacatataga    900
gtaaaaaacg gagatactct tggagagata gcattaagaa attctatgtc tttgaaagat    960
cttcttcaat taaataatct aaaaaataat tatgtgctta aagtaggaga tactttaaaa   1020
atatatgata atattaatat aacaagttct tcaacatcaa caacatacag aactttggaa   1080
aattataaag taaaaagcgg tgatacttta agcggaatag ctctagcaag aggaatggat   1140
ctagtagaat tatactccat aaataatata aatgacaaat atattttgaa agttggagat   1200
aatcttaaag tatatgctaa ccctaaaaaa acaactactt tagtaatatc aaattataaa   1260
gttcaaagcg gagatagttt atactcaata gcaaaaaaac ataaaatgga tttaagagat   1320
ttaatgcagc ttaataatat aaaaaatgct aatgaatata aattatatgt cggcgccaat   1380
ctaaaagtaa aaacagcaaa aatggtgcct tattctttta atgatgattc tatattacct   1440
gacagctctt ttatatggcc ttataaagga ataataattt caggatatgg agtagcttct   1500
gataaacttg caaacagagg tgtgaatata ttaggagatg taggagacaa agttgtagct   1560
tctgatgacg gaatcgtaga atatgctgat aatataagag gattcggtac tgttataata   1620
cttaaacata aaaacggata taatacttct tatgctcatc tttctaagat aaatgttaaa   1680
cttggagata tagtaaagaa aggagattat ataggagaca ttggcgatac tggtatgata   1740
gatagaagcg aactatattt taagatttct tatcagggaa gatcaataga tcctgttaaa   1800
cttcttccta aaagt                                                    1815
```

<210> SEQ ID NO 58
<211> LENGTH: 605
<212> TYPE: PRT
<213> ORGANISM: Brachyspira hyodysenteriae

<400> SEQUENCE: 58

```
Met Lys Asn Ile Phe Lys Tyr Ala Ser Ile Ile Gly Cys Thr Phe Ala
1               5                   10                  15

Ser Leu Asn Phe Ala Ala Asp Tyr Ile Asp Tyr Lys Val Lys Asn Gly
            20                  25                  30

Asp Thr Leu Phe Gly Ile Ala Phe Ala His Asp Met Ser Ala Asn Glu
        35                  40                  45

Phe Leu Lys Val Asn Asn Ile Lys Asp Pro Asp Lys Tyr Asn Leu Arg
    50                  55                  60

Val Gly Glu Thr Leu Lys Val Lys Asp Lys Gly Tyr Thr Leu Val Tyr
65                  70                  75                  80

Asp Ser Asp Asn Lys Val Phe Gly Leu Lys Gly Glu Glu Gly Asn Ser
                85                  90                  95
```

-continued

```
Tyr Lys Asp Tyr Lys Val Lys Asn Gly Asp Thr Leu Phe Gly Ile Ala
                100                 105                 110
Phe Ala His Gly Met Thr Ala Asn Glu Phe Leu Ala Ile Asn Asn Ile
            115                 120                 125
Lys Asp Ala Asn Lys Tyr Asn Leu Arg Val Gly Gln Thr Leu Lys Val
        130                 135                 140
Ala Asn Asn Gln Lys Glu Asn Asn Ala Ser Ser Asn Asn Ile Asn Asn
145                 150                 155                 160
Ser Asp Asn Thr Glu Asn Tyr Asp Thr Tyr Lys Val Gln Ser Gly Asp
                165                 170                 175
Thr Leu Tyr Gly Ile Ala Phe Ser His Gly Met Thr Ala Ser Glu Phe
            180                 185                 190
Leu Lys Ile Asn Asn Ile Asp Asp Pro Asp Lys Tyr Lys Leu Tyr Val
        195                 200                 205
Gly Lys Thr Met Tyr Val Lys Ser Ser Lys Lys Glu Asn Asn Leu Asn
            210                 215                 220
Thr Asn Asn Glu Lys Asp Thr Gly Lys Glu Ile Glu Tyr Tyr Thr Val
225                 230                 235                 240
Lys Ser Gly Asp Thr Leu Tyr Gly Ile Ala Phe Gln Asn Asp Ile Ser
                245                 250                 255
Val Asn Asp Phe Leu Arg Ile Asn Asn Ile Asp Asp Pro Leu Lys Tyr
            260                 265                 270
Lys Leu Arg Thr Gly Glu Lys Leu Lys Ile Tyr Ala Arg Glu Asn Ala
        275                 280                 285
Ser Asn Thr Gln Ser Lys Thr Ile Lys Thr Tyr Arg Val Lys Asn Gly
            290                 295                 300
Asp Thr Leu Gly Glu Ile Ala Leu Arg Asn Ser Met Ser Leu Lys Asp
305                 310                 315                 320
Leu Leu Gln Leu Asn Asn Leu Lys Asn Asn Tyr Val Leu Lys Val Gly
                325                 330                 335
Asp Thr Leu Lys Ile Tyr Asp Asn Ile Asn Ile Thr Ser Ser Ser Thr
            340                 345                 350
Ser Thr Thr Tyr Arg Thr Leu Glu Asn Tyr Lys Val Lys Ser Gly Asp
        355                 360                 365
Thr Leu Ser Gly Ile Ala Leu Ala Arg Gly Met Asp Leu Val Glu Leu
            370                 375                 380
Tyr Ser Ile Asn Asn Ile Asn Asp Lys Tyr Ile Leu Lys Val Gly Asp
385                 390                 395                 400
Asn Leu Lys Val Tyr Ala Asn Pro Lys Lys Thr Thr Thr Leu Val Ile
                405                 410                 415
Ser Asn Tyr Lys Val Gln Ser Gly Asp Ser Leu Tyr Ser Ile Ala Lys
            420                 425                 430
Lys His Lys Met Asp Leu Arg Asp Leu Met Gln Leu Asn Asn Ile Lys
        435                 440                 445
Asn Ala Asn Glu Tyr Lys Leu Tyr Val Gly Ala Asn Leu Lys Val Lys
            450                 455                 460
Thr Ala Lys Met Val Pro Tyr Ser Phe Asn Asp Ser Ile Leu Pro
465                 470                 475                 480
Asp Ser Ser Phe Ile Trp Pro Tyr Lys Gly Ile Ile Ser Gly Tyr
                485                 490                 495
Gly Val Ala Ser Asp Lys Leu Ala Asn Arg Gly Val Asn Ile Leu Gly
            500                 505                 510
Asp Val Gly Asp Lys Val Val Ala Ser Asp Asp Gly Ile Val Glu Tyr
```

```
                515                 520                 525

Ala Asp Asn Ile Arg Gly Phe Gly Thr Val Ile Ile Leu Lys His Lys
        530                 535                 540

Asn Gly Tyr Asn Thr Ser Tyr Ala His Leu Ser Lys Ile Asn Val Lys
545                 550                 555                 560

Leu Gly Asp Ile Val Lys Lys Gly Asp Tyr Ile Gly Asp Ile Gly Asp
                565                 570                 575

Thr Gly Met Ile Asp Arg Ser Glu Leu Tyr Phe Lys Ile Ser Tyr Gln
        580                 585                 590

Gly Arg Ser Ile Asp Pro Val Lys Leu Leu Pro Lys Ser
        595                 600                 605

<210> SEQ ID NO 59
<211> LENGTH: 1068
<212> TYPE: DNA
<213> ORGANISM: Brachyspira hyodysenteriae

<400> SEQUENCE: 59
atgattagaa atattaaata tatttcatt atatatttat tagctatttc ctgctctaat      60
tatagagtta ctgatccatt ctccattcaa aataatagta ataataacat aagcattata    120
cctgaatatg tagatgctca atatttcatc aaagcagatt acactgaaca gcaaatagaa    180 gaataatga ataaatattt ccagaatttt ggagaatata taatattttt aaatgatact    240
aaagataata tagataaaaa taaaacaata gaaacaataa ataaagtagt taataaacct    300
gcttatttac ataacggagc tgctgttgat ttaagcagaa ctgatataac agaaatagca    360
caaagtgcat ttaatgcaaa taaaaattta atagaagtta agcttcctaa ctcattaaaa    420 actataaaatt catcagcatt tcaatcatgc gaaagattaa aatatataaa tctagtaagc    480
tctataaccg atatacaatc tgctgcattt caagactgta tgtctttaga aattattaat    540
ataacatcaa aagtaaaaac tatagctaat aatgcattta aaaattgtgt tacttttaaga    600 gaagtaatac ttcctgaagg attaacttca atagcagatg gagcattcaa ttactgtaca    660
tcattagaat caattaattt tccatcaact ttacaaacta taggcacagc agcattttac    720
agctgtaaat cattaaaaag tataaaatta atcaaggat taactaccat aaatgataat    780
gcttttaatc tttgctcatc attaacagct ataagcttac ctaatagtat aacaagcctt    840
ttaaatcctt cagaaggtaa ggttttttct gattgtaaaa tgcttaaaaa tgttgaatat    900
cttgatacag atcccgtaaa aatacttaaa gaaatgata cattcagagg ttcacctgta    960
accgatttat accttcctaa tgtggcagaa gatcctaaaa atggaagctg ggataatttt   1020
ttaggtgttg cttggacaac tattcattat ggaaaatcta tgcctagg                1068

<210> SEQ ID NO 60
<211> LENGTH: 356
<212> TYPE: PRT
<213> ORGANISM: Brachyspira hyodysenteriae

<400> SEQUENCE: 60

Met Ile Arg Asn Ile Lys Tyr Ile Phe Ile Ile Tyr Leu Leu Ala Ile
1               5                  10                  15

Ser Cys Ser Asn Tyr Arg Val Thr Asp Pro Phe Ser Ile Gln Asn Asn
                20                  25                  30

Ser Asn Asn Asn Ile Ser Ile Ile Pro Glu Tyr Val Asp Ala Gln Tyr
        35                  40                  45

Phe Ile Lys Ala Asp Tyr Thr Glu Gln Gln Ile Glu Glu Ile Met Asn
```

```
                50                  55                  60
Lys Tyr Phe Gln Asn Phe Gly Glu Tyr Ile Ile Phe Leu Asn Asp Thr
 65                  70                  75                  80

Lys Asp Asn Ile Asp Lys Asn Lys Thr Ile Glu Thr Ile Asn Lys Val
                 85                  90                  95

Val Asn Lys Pro Ala Tyr Leu His Asn Gly Ala Ala Val Asp Leu Ser
            100                 105                 110

Arg Thr Asp Ile Thr Glu Ile Ala Gln Ser Ala Phe Asn Ala Asn Lys
        115                 120                 125

Asn Leu Ile Glu Val Lys Leu Pro Asn Ser Leu Lys Thr Ile Asn Ser
    130                 135                 140

Ser Ala Phe Gln Ser Cys Glu Arg Leu Lys Tyr Ile Asn Leu Val Ser
145                 150                 155                 160

Ser Ile Thr Asp Ile Gln Ser Ala Phe Gln Asp Cys Met Ser Leu
            165                 170                 175

Glu Ile Ile Asn Ile Thr Ser Lys Val Lys Thr Ile Ala Asn Asn Ala
                180                 185                 190

Phe Lys Asn Cys Val Thr Leu Arg Glu Val Ile Leu Pro Glu Gly Leu
            195                 200                 205

Thr Ser Ile Ala Asp Gly Ala Phe Asn Tyr Cys Thr Ser Leu Glu Ser
    210                 215                 220

Ile Asn Phe Pro Ser Thr Leu Gln Thr Ile Gly Thr Ala Phe Tyr
225                 230                 235                 240

Ser Cys Lys Ser Leu Lys Ser Ile Lys Leu Asn Gln Gly Leu Thr Thr
                245                 250                 255

Ile Asn Asp Asn Ala Phe Asn Leu Cys Ser Ser Leu Thr Ala Ile Ser
            260                 265                 270

Leu Pro Asn Ser Ile Thr Ser Leu Leu Asn Pro Ser Glu Gly Lys Val
        275                 280                 285

Phe Ser Asp Cys Lys Met Leu Lys Asn Val Glu Tyr Leu Asp Thr Asp
    290                 295                 300

Pro Val Lys Ile Leu Lys Glu Asn Asp Thr Phe Arg Gly Ser Pro Val
305                 310                 315                 320

Thr Asp Leu Tyr Leu Pro Asn Val Ala Glu Asp Pro Lys Asn Gly Ser
                325                 330                 335

Trp Asp Asn Phe Leu Gly Val Ala Trp Thr Thr Ile His Tyr Gly Lys
            340                 345                 350

Ser Met Pro Arg
        355

<210> SEQ ID NO 61
<211> LENGTH: 1296
<212> TYPE: DNA
<213> ORGANISM: Brachyspira hyodysenteriae

<400> SEQUENCE: 61
atggatataa ttataataat agtgttaata cttttaaatg gtattttgc catgtcggaa      60 attgcagtaa tttctgctag aaaatcttct cttatgaaag acagcaaaga aggaaataaa    120
ggtgcaaaga ctgcattagc tttagcagat aatcctgaca aattttatc tacaatacaa    180 ataggtataa ctttaatagg tatattaaca ggtatttact caggcgatac agttgccaaa    240
gaagtttcaa atttacttgt aaaaataaat gtaccattaa attatgcttc tttaatagct    300
caggtattgg tggtagcatt ggtaacatat cttacattga tattcggaga gcttgtgcct    360
```

```
aaaagaatag gaatggtaat gcctgaaaga atagcaaaag tggttgcagc tcctatgaca    420
atacttgcaa agataggtgc tccttttgtg tggatattat caaatagcgc attgcttgtt    480
tcaagagttt tgggtataaa agatgataaa agtcctgtta ctgaagagga aataaaatct    540
atgatagaag agggcagaca aggggggagaa gttaaggaga tagaacagaa tattatagag    600
agggctttct ttttgggaga tagaaaaata gaatctataa tgacacatag aaatgatatg    660 gtattttag atataaatat gagtaatgat gagataaaaa agatagtatc aaacattct    720 ttttctgctt atcctgttgt tgataaaaat ttggataata ttgtaggagt tgtaagagta    780
actgatatat tcgataaatt aaatacttca aaggctaaaa tagaaaagtt tgtgaagaaa    840
gctaattact ttcataacaa tatggaagtt tatttggttc ttgaagagat gaaaagaat    900 aatactaaaa taggtcttgt atcagatgag tttgggaata tagacggaat gattactcaa    960
agcgatatat tcgaggcttt agtgggttct gtaacagaag gaaaagacag taaggatatt    1020
agaaagagaa agagcggaag ttggtttgta gatggtcaat gtcctatgta tgatttctta    1080
gagtattttg aaatagaaga tgaaaatgct tctaataatt ataatactat aagcggtttg    1140
attttagaat tattacagca tgtacctagt gaaggagaat ctttagaatg gaagaattta    1200
aatttagaag ttgttgatat ggacggtgct agaatagata aggttatagt aaataaaata    1260
gaaaaaactg atgaaagaa tgattcagac actgaa                             1296
```

<210> SEQ ID NO 62
<211> LENGTH: 432
<212> TYPE: PRT
<213> ORGANISM: Brachyspira hyodysenteriae

<400> SEQUENCE: 62

Met Asp Ile Ile Ile Ile Ile Val Leu Ile Leu Leu Asn Gly Ile Phe
1               5                   10                  15

Ala Met Ser Glu Ile Ala Val Ile Ser Ala Arg Lys Ser Ser Leu Met
            20                  25                  30

Lys Asp Ser Lys Glu Gly Asn Lys Gly Ala Lys Thr Ala Leu Ala Leu
        35                  40                  45

Ala Asp Asn Pro Asp Lys Phe Leu Ser Thr Ile Gln Ile Gly Ile Thr
    50                  55                  60

Leu Ile Gly Ile Leu Thr Gly Ile Tyr Ser Gly Asp Thr Val Ala Lys
65                  70                  75                  80

Glu Val Ser Asn Leu Leu Val Lys Ile Asn Val Pro Leu Asn Tyr Ala
                85                  90                  95

Ser Leu Ile Ala Gln Val Leu Val Val Ala Leu Val Thr Tyr Leu Thr
            100                 105                 110

Leu Ile Phe Gly Glu Leu Val Pro Lys Arg Ile Gly Met Val Met Pro
        115                 120                 125

Glu Arg Ile Ala Lys Val Val Ala Ala Pro Met Thr Ile Leu Ala Lys
    130                 135                 140

Ile Gly Ala Pro Phe Val Trp Ile Leu Ser Asn Ser Ala Leu Leu Val
145                 150                 155                 160

Ser Arg Val Leu Gly Ile Lys Asp Asp Lys Ser Pro Val Thr Glu Glu
                165                 170                 175

Glu Ile Lys Ser Met Ile Glu Glu Gly Arg Gln Gly Gly Glu Val Lys
            180                 185                 190

Glu Ile Glu Gln Asn Ile Ile Glu Arg Ala Phe Phe Leu Gly Asp Arg
        195                 200                 205

```
Lys Ile Glu Ser Ile Met Thr His Arg Asn Asp Met Val Phe Leu Asp
            210                 215                 220

Ile Asn Met Ser Asn Asp Glu Ile Lys Lys Ile Val Ser Lys His Ser
225                 230                 235                 240

Phe Ser Ala Tyr Pro Val Val Asp Lys Asn Leu Asp Asn Ile Val Gly
                245                 250                 255

Val Val Arg Val Thr Asp Ile Phe Asp Lys Leu Asn Thr Ser Lys Ala
            260                 265                 270

Lys Ile Glu Lys Phe Val Lys Lys Ala Asn Tyr Phe His Asn Asn Met
                275                 280                 285

Glu Val Tyr Leu Val Leu Glu Glu Met Lys Lys Asn Asn Thr Lys Ile
290                 295                 300

Gly Leu Val Ser Asp Glu Phe Gly Asn Ile Asp Gly Met Ile Thr Gln
305                 310                 315                 320

Ser Asp Ile Phe Glu Ala Leu Val Gly Ser Val Thr Glu Gly Lys Asp
                325                 330                 335

Ser Lys Asp Ile Arg Lys Arg Lys Ser Gly Ser Trp Phe Val Asp Gly
            340                 345                 350

Gln Cys Pro Met Tyr Asp Phe Leu Glu Tyr Phe Glu Ile Glu Asp Glu
                355                 360                 365

Asn Ala Ser Asn Asn Tyr Asn Thr Ile Ser Gly Leu Ile Leu Glu Leu
370                 375                 380

Leu Gln His Val Pro Ser Glu Gly Glu Ser Leu Glu Trp Lys Asn Leu
385                 390                 395                 400

Asn Leu Glu Val Val Asp Met Asp Gly Ala Arg Ile Asp Lys Val Ile
                405                 410                 415

Val Asn Lys Ile Glu Lys Thr Asp Glu Lys Asn Asp Ser Asp Thr Glu
            420                 425                 430

<210> SEQ ID NO 63
<211> LENGTH: 2940
<212> TYPE: DNA
<213> ORGANISM: Brachyspira hyodysenteriae

<400> SEQUENCE: 63
atgcgaatct ttatcttgtt attatttaca ttgattttta atgtatgttt atatgctcag      60
gatactaatg taaataatac agcagcaaca ataatacta ctgcagcaac caataatgta     120
ggcgaaagtg caataatgca gataaataga tttgatgcta aaagaaatcc tgtatcattt     180
attaatttag ttaattttac accatattat gtattgcagg aatatgctag ggttaataat     240
atagaaattt atccctatga tactgaaagt acattaagag caagaatcat tgaaagacaa     300
gtaaatataa acaggaagt tattaataat aaagatgaaa tacgcgaagt agcaagaaca     360
actataaata gaggcggtgc tcaggtagaa cttataggtg cagattttgc tgaaagatat     420
accatagatg aagcaggtga agagcttata tcattatatg gtaatgttac catgaaaatg     480
tataataata cattagttgc tgataaggtt gtttatagct aaaaacagg agaagttttt     540 gcttcaggaa atttaactgt agcatctgaa ggaagtactt tcaaaggtga atggtttatg     600
cttaatagag aaagtaaaag aggcatacta ttcggcggaa atacgaaatt catgagtttt     660
acagttgaag gcgtataat taaatttaat gaccaagatt ttttgctga aaacagcagt     720 gtgagttttt cacgtcttac tcctatagcg catgattttt tagcgagtag agtttatctt     780
tgggatacta aaaagatgat ggttttcaat agtatctata gggtaggaag acagcctgta     840
ttttattttc cattatttat acagaataat tttggtactg gtataatatc ttctttttggg     900
```

```
cagtctttga gagaaggtgt ttatattcaa aattataaga tatttaattt atatggtgtg    960
cagcataaga taagattcga tgcctatcag aaattaggtt ttttattagg agatgaaata   1020
aggtatacaa gtcagtatca ggatttagca cttgatgcta tgtttgcttt tggaaggcag   1080
tattatttat ttgattccta tattacttca agtgtaggat ttggtacaag gtatgttaac   1140
tattttggat caggtgaagg cggaaagttt gtaccaagat ataaatttca atatgatcat   1200
accattcaat tatataatag tcaaaatata aatagttata ttacaggaaa gttaaattta   1260
aatagcgact tatatttcag atctgatttt tacaatcaaa gaggacagtt tgatatatta   1320
acatttttta catcacttac aggaaatttg caggacatag gagattctta tcctgaaaat   1380
tatattgaaa attctgttta tcttaataat aatatttacg gacttaattt aaaagttggt   1440
gcagaatggg atttagaatc tgttagaaat atatcggttg atgttaatac taatttcgac   1500
tattatatgc ctaaaccata taaacttgta cttccttctg tagaagctag ttacaattct   1560
atatttggaa atgagacatc ttattacttt ccaaatctta acattaacta atttttaaga   1620
gctaattata atcatactat aaattataag acttctgaag gtattgcttt ttataacaat   1680
cctatgcttg actcacaatt aaatgataaa cttgctgaaa gagataatct taatttacat   1740
ggtgatatat caagagcttt tactaatgat tttttaagat ttgtacctag ctttaatatg   1800
gaatactcat atcaaaatag tatagatcct aaagcagaag atttgattta tgataaagat   1860
aatacttact ttggtatagg cacaggaatg aattttttcta tgttttttacc ttacagtata   1920 ttgccatatg atttcacaag atattttgaa cctactgtta gatgggatac aacatataca   1980
ttgggatata gatttaaaga aaaatacatt gatacagatt ataaagattc tcaattcggt   2040
gaatttaata atcatagctt tacaactaga ttttctatgg gcggaaccgg atacagctta   2100
ttttatttgc ctgatttgaa tctcaatatg gaaacattta taactacagg ttatgatttt   2160
atacctagtt ataattcaga aacaagaact tatcaagttg aattttctac aaataaaatg   2220
cttacaactg aagtaggtgc ttcagcaaga ctttttatata atcaatctta tgtttcttat   2280
gatataacta gaaatttatt aggaactaat ttaacagcaa atagaataaa tgcatatttt   2340
cactttccta taccttaggg taaaattaca gattggattt taataaaaaa caataaaaga   2400
cctttctttg atggtatagt taatgatttt aatttatatt ttggttttgc ctttactcat   2460
gattttataa attatagata taatactacc gcatttacat ttggtataga gcttcaggtt   2520
ttggaacaat ggaaatttag aatagcaact actagtgcaa atgagaatgc atatagatat   2580
ataaaatctt atgcagaaaa agaaaatcaa acttgggtta atccttttttg ggatatcata   2640 aattcattca atttctctga cagtaaaaaa agaactgaaa gtttatttaa attaaaatct   2700
atagaagcta gtgtttggca tgaattagac ggatggcaga ttcaggctac atttgctgta   2760
agaccttcta ctctccctc tgatattact tcaggttcag taaaaggagt ttattggaac   2820
aaggagtttt ggattgaatt tactcttaca gactttccta atgttggatt gcctaagaaa   2880
gaatataatc ttaatagtac tattaccgat ttacaagata gtgctgctgt tactactcca   2940
```

<210> SEQ ID NO 64
<211> LENGTH: 980
<212> TYPE: PRT
<213> ORGANISM: Brachyspira hyodysenteriae

<400> SEQUENCE: 64

Met Arg Ile Phe Ile Leu Leu Leu Phe Thr Leu Ile Phe Asn Val Cys
 1               5                   10                  15

```
Leu Tyr Ala Gln Asp Thr Asn Val Asn Asn Thr Ala Ala Thr Asn Asn
            20                  25                  30

Thr Thr Ala Ala Thr Asn Asn Val Gly Glu Ser Ala Ile Met Gln Ile
        35                  40                  45

Asn Arg Phe Asp Ala Lys Arg Asn Pro Val Ser Phe Ile Asn Leu Val
 50                  55                  60

Asn Phe Thr Pro Tyr Tyr Val Leu Gln Glu Tyr Ala Arg Val Asn Asn
 65                  70                  75                  80

Ile Glu Ile Tyr Pro Tyr Asp Thr Glu Ser Thr Leu Arg Ala Arg Ile
                85                  90                  95

Ile Glu Arg Gln Val Asn Ile Lys Gln Glu Val Ile Asn Asn Lys Asp
            100                 105                 110

Glu Ile Arg Glu Val Ala Arg Thr Thr Ile Asn Arg Gly Gly Ala Gln
        115                 120                 125

Val Glu Leu Ile Gly Ala Asp Phe Ala Glu Arg Tyr Thr Ile Asp Glu
130                 135                 140

Ala Gly Glu Glu Leu Ile Ser Leu Tyr Gly Asn Val Thr Met Lys Met
145                 150                 155                 160

Tyr Asn Asn Thr Leu Val Ala Asp Lys Val Tyr Ser Leu Lys Thr
                165                 170                 175

Gly Glu Val Phe Ala Ser Gly Asn Leu Thr Val Ala Ser Glu Gly Ser
            180                 185                 190

Thr Phe Lys Gly Glu Trp Phe Met Leu Asn Arg Glu Ser Lys Arg Gly
        195                 200                 205

Ile Leu Phe Gly Gly Asn Thr Lys Phe Met Ser Phe Thr Val Glu Gly
            210                 215                 220

Arg Ile Ile Lys Phe Asn Asp Gln Asp Phe Ala Glu Asn Ser Ser
225                 230                 235                 240

Val Ser Phe Ser Arg Leu Thr Pro Ile Ala His Asp Phe Leu Ala Ser
                245                 250                 255

Arg Val Tyr Leu Trp Asp Thr Lys Lys Met Met Val Phe Asn Ser Ile
            260                 265                 270

Tyr Arg Val Gly Arg Gln Pro Val Phe Tyr Phe Pro Leu Phe Ile Gln
        275                 280                 285

Asn Asn Phe Gly Thr Gly Ile Ile Ser Ser Phe Gly Gln Ser Leu Arg
290                 295                 300

Glu Gly Val Tyr Ile Gln Asn Tyr Lys Ile Phe Asn Leu Tyr Gly Val
305                 310                 315                 320

Gln His Lys Ile Arg Phe Asp Ala Tyr Gln Lys Leu Gly Phe Leu Leu
                325                 330                 335

Gly Asp Glu Ile Arg Tyr Thr Ser Gln Tyr Gln Asp Leu Ala Leu Asp
            340                 345                 350

Ala Met Phe Ala Phe Gly Arg Gln Tyr Tyr Leu Phe Asp Ser Tyr Ile
        355                 360                 365

Thr Ser Ser Val Gly Phe Gly Thr Arg Tyr Val Asn Tyr Phe Gly Ser
            370                 375                 380

Gly Glu Gly Gly Lys Phe Val Pro Arg Tyr Lys Phe Gln Tyr Asp His
385                 390                 395                 400

Thr Ile Gln Leu Tyr Asn Ser Gln Asn Ile Asn Ser Tyr Ile Thr Gly
                405                 410                 415

Lys Leu Asn Leu Asn Ser Asp Leu Tyr Phe Arg Ser Asp Phe Tyr Asn
                420                 425                 430
```

```
Gln Arg Gly Gln Phe Asp Ile Leu Thr Phe Phe Thr Ser Leu Thr Gly
            435                 440                 445

Asn Leu Gln Asp Ile Gly Asp Ser Tyr Pro Glu Asn Tyr Ile Glu Asn
    450                 455                 460

Ser Val Tyr Leu Asn Asn Asn Ile Tyr Gly Leu Asn Leu Lys Val Gly
465                 470                 475                 480

Ala Glu Trp Asp Leu Glu Ser Val Arg Asn Ile Ser Val Asp Val Asn
                485                 490                 495

Thr Asn Phe Asp Tyr Tyr Met Pro Lys Pro Tyr Lys Leu Val Leu Pro
            500                 505                 510

Ser Val Glu Ala Ser Tyr Asn Ser Ile Phe Gly Asn Glu Thr Ser Tyr
        515                 520                 525

Tyr Phe Pro Asn Leu Asn Ile Asn Tyr Asn Leu Arg Ala Asn Tyr Asn
    530                 535                 540

His Thr Ile Asn Tyr Lys Thr Ser Glu Gly Ile Ala Phe Tyr Asn Asn
545                 550                 555                 560

Pro Met Leu Asp Ser Gln Leu Asn Asp Lys Leu Ala Glu Arg Asp Asn
                565                 570                 575

Leu Asn Leu His Gly Asp Ile Ser Arg Ala Phe Thr Asn Asp Phe Leu
            580                 585                 590

Arg Phe Val Pro Ser Phe Asn Met Glu Tyr Ser Tyr Gln Asn Ser Ile
        595                 600                 605

Asp Pro Lys Ala Glu Asp Leu Ile Tyr Asp Lys Asp Asn Thr Tyr Phe
    610                 615                 620

Gly Ile Gly Thr Gly Met Asn Phe Ser Met Phe Leu Pro Tyr Ser Ile
625                 630                 635                 640

Leu Pro Tyr Asp Phe Thr Arg Tyr Phe Glu Pro Thr Val Arg Trp Asp
                645                 650                 655

Thr Thr Tyr Thr Leu Gly Tyr Arg Phe Lys Glu Lys Tyr Ile Asp Thr
            660                 665                 670

Asp Tyr Lys Asp Ser Gln Phe Gly Glu Phe Asn Asn His Ser Phe Thr
        675                 680                 685

Thr Arg Phe Ser Met Gly Gly Thr Gly Tyr Ser Leu Phe Tyr Leu Pro
    690                 695                 700

Asp Leu Asn Leu Asn Met Glu Thr Phe Ile Thr Thr Gly Tyr Asp Phe
705                 710                 715                 720

Ile Pro Ser Tyr Asn Ser Glu Thr Arg Thr Tyr Gln Val Glu Phe Ser
                725                 730                 735

Thr Asn Lys Met Leu Thr Thr Glu Val Gly Ala Ser Ala Arg Leu Leu
            740                 745                 750

Tyr Asn Gln Ser Tyr Val Ser Tyr Asp Ile Thr Arg Asn Leu Leu Gly
        755                 760                 765

Thr Asn Leu Thr Ala Asn Arg Ile Asn Ala Tyr Phe His Phe Pro Ile
    770                 775                 780

Pro Leu Gly Lys Ile Thr Asp Trp Ile Leu Ile Lys Asn Asn Lys Arg
785                 790                 795                 800

Pro Phe Phe Asp Gly Ile Val Asn Asp Phe Asn Leu Tyr Phe Gly Phe
                805                 810                 815

Ala Phe Thr His Asp Phe Ile Asn Tyr Arg Tyr Asn Thr Thr Ala Phe
            820                 825                 830

Thr Phe Gly Ile Glu Leu Gln Val Leu Glu Gln Trp Lys Phe Arg Ile
        835                 840                 845

Ala Thr Thr Ser Ala Asn Glu Asn Ala Tyr Arg Tyr Ile Lys Ser Tyr
```

```
                   850                 855                 860
Ala Glu Lys Glu Asn Gln Thr Trp Val Asn Pro Phe Trp Asp Ile Ile
865                 870                 875                 880

Asn Ser Phe Asn Phe Ser Asp Ser Lys Lys Arg Thr Glu Ser Leu Phe
                885                 890                 895

Lys Leu Lys Ser Ile Glu Ala Ser Val Trp His Glu Leu Asp Gly Trp
            900                 905                 910

Gln Ile Gln Ala Thr Phe Ala Val Arg Pro Ser Thr Leu Pro Ser Asp
        915                 920                 925

Ile Thr Ser Gly Ser Val Lys Gly Val Tyr Trp Asn Lys Glu Phe Trp
    930                 935                 940

Ile Glu Phe Thr Leu Thr Asp Phe Pro Asn Val Gly Leu Pro Lys Lys
945                 950                 955                 960

Glu Tyr Asn Leu Asn Ser Thr Ile Thr Asp Leu Gln Asp Ser Ala Ala
                965                 970                 975

Val Thr Thr Pro
            980

<210> SEQ ID NO 65
<211> LENGTH: 1611
<212> TYPE: DNA
<213> ORGANISM: Brachyspira hyodysenteriae

<400> SEQUENCE: 65
atgtcagaga taaaacagt aagtaaagaa aagatagcta aatcatcatt aaaaatgtca      60
ttggtaacta ctgtaagcag agtattcgga cttgtaagag atcaaataca ggcggctttg     120
cttggtacta cattcatagc agatgctttt gcaataggat ttatacttcc aaatttattg     180
aggcgattat ttgctgaagg caatatggtt gcaagcttta tacctgtatt tacagagctt     240
gaaaagaaa aaggtattga agaatcaaag aaattttta gggcagtttt tacattattg       300
ggattaatac ttatagtagt tgtaggcatc ggaataataa tatctccttt gcttgtaaaa     360
atactttata atctgcaca taataatata gaagcactta atttggcatc ggatctatca     420
agaataatgt ttccttatct tctatttata tctttggcag ctttgatgca gggcgtactt     480
aatataagag gctattattc aatatcagct gcaagtccta tactttttaaa tactgtaatt    540
atatctatgg ctttgttctt taaattcttt ttacctaatt ttttttaataa tatgccttat    600
gtatttgcat ttgctgtgct gcttggtgga ttcgtacagt ttgcctatca aatgcctttt     660
gtacataaac aaggttttag tttcaagcct tattttcatt ttaaagaacc ctatgtcata     720
aagatgataa aattatttgc tcctggtatt ttcggagcta gtatatatca gataaatttg     780
cttgtttcta ctgcatttgc tggagctatt ggagagggca gggtttcagc tgttactttt     840
gctactagaa tacatgaatt tgttttgggc gtttttgctg tgagtgtggc aactgttatg     900
cttcctactt taagtaaatt aatagctgat aataaaaaag atgaagctgt tgaaaattta     960
ggatattctt taaggcttgt tgctttagtt actattcctg ctactttcgg atttgtggta    1020
cttggcagag aaattgtaag aatgatattt gaatatggag cttttttcttc aaaatctaca   1080
tatttagtat cgagtgcttt aagatattta tccatatcct tattctttgt ggcaagctat    1140
agaatacttg tacagtcatt ttatgctatg aaagatatga aaactcctgt atatgtggca    1200
ttttttaccct ttattattaa tgctgttagt aattatttat gtgtttatat atttaaattc   1260
gatattatag gaatatctat atcaagtgtt gttgcaaata ttgtatcttt ttgtatacta    1320
tatatattgc ttataaagag aatggcagtg aaatcgataa taaataaaaa aattgaggtt    1380
```

```
gtaaagacat tggctgctag tttatttatg gctgcttctg tctatggaat gaaatattat    1440
ttattataca gcaatgccga ttctaggata atttttataa ttaaagtatt tatagtgata    1500
ttattaggag ttgttgttta ttctataatg aacattatat taagaaatga tgattttgtt    1560
tcctttatta gtatgtttaa aggcagatta tcaagaaagt ttctgaaaaa a             1611
```

<210> SEQ ID NO 66
<211> LENGTH: 537
<212> TYPE: PRT
<213> ORGANISM: Brachyspira hyodysenteriae

<400> SEQUENCE: 66

```
Met Ser Glu Asn Lys Thr Val Ser Lys Glu Lys Ile Ala Lys Ser Ser
1               5                   10                  15

Leu Lys Met Ser Leu Val Thr Thr Val Ser Arg Val Phe Gly Leu Val
            20                  25                  30

Arg Asp Gln Ile Gln Ala Ala Leu Leu Gly Thr Thr Phe Ile Ala Asp
        35                  40                  45

Ala Phe Ala Ile Gly Phe Ile Leu Pro Asn Leu Leu Arg Arg Leu Phe
    50                  55                  60

Ala Glu Gly Asn Met Val Ala Ser Phe Ile Pro Val Phe Thr Glu Leu
65                  70                  75                  80

Glu Lys Glu Lys Gly Ile Glu Glu Ser Lys Lys Phe Phe Arg Ala Val
                85                  90                  95

Phe Thr Leu Leu Gly Leu Ile Leu Ile Val Val Gly Ile Gly Ile
            100                 105                 110

Ile Ile Ser Pro Leu Leu Val Lys Ile Leu Tyr Lys Ser Ala His Asn
        115                 120                 125

Asn Ile Glu Ala Leu Asn Leu Ala Ser Asp Leu Ser Arg Ile Met Phe
    130                 135                 140

Pro Tyr Leu Leu Phe Ile Ser Leu Ala Ala Leu Met Gln Gly Val Leu
145                 150                 155                 160

Asn Ile Arg Gly Tyr Tyr Ser Ile Ser Ala Ala Ser Pro Ile Leu Leu
                165                 170                 175

Asn Thr Val Ile Ile Ser Met Ala Leu Phe Phe Lys Phe Phe Leu Pro
            180                 185                 190

Asn Phe Phe Asn Asn Met Ala Tyr Val Phe Ala Phe Ala Val Leu Leu
        195                 200                 205

Gly Gly Phe Val Gln Phe Ala Tyr Gln Met Pro Phe Val His Lys Gln
    210                 215                 220

Gly Phe Ser Phe Lys Pro Tyr Phe His Phe Lys Glu Pro Tyr Val Ile
225                 230                 235                 240

Lys Met Ile Lys Leu Phe Ala Pro Gly Ile Phe Gly Ala Ser Ile Tyr
                245                 250                 255

Gln Ile Asn Leu Leu Val Ser Thr Ala Phe Ala Gly Ala Ile Gly Glu
            260                 265                 270

Gly Arg Val Ser Ala Val Thr Phe Ala Thr Arg Ile His Glu Phe Val
        275                 280                 285

Leu Gly Val Phe Ala Val Ser Val Ala Thr Val Met Leu Pro Thr Leu
    290                 295                 300

Ser Lys Leu Ile Ala Asp Asn Lys Lys Asp Glu Ala Val Glu Asn Leu
305                 310                 315                 320

Gly Tyr Ser Leu Arg Leu Val Ala Leu Val Thr Ile Pro Ala Thr Phe
                325                 330                 335
```

```
Gly Phe Val Val Leu Gly Arg Glu Ile Val Arg Met Ile Phe Glu Tyr
            340                 345                 350
Gly Ala Phe Ser Ser Lys Ser Thr Tyr Leu Val Ser Ser Ala Leu Arg
        355                 360                 365
Tyr Leu Ser Ile Ser Leu Phe Phe Val Ala Ser Tyr Arg Ile Leu Val
    370                 375                 380
Gln Ser Phe Tyr Ala Met Lys Asp Met Lys Thr Pro Val Tyr Val Ala
385                 390                 395                 400
Phe Phe Thr Phe Ile Ile Asn Ala Val Ser Asn Tyr Leu Cys Val Tyr
                405                 410                 415
Ile Phe Lys Phe Asp Ile Ile Gly Ile Ser Ile Ser Val Val Ala
            420                 425                 430
Asn Ile Val Ser Phe Cys Ile Leu Tyr Ile Leu Ile Lys Arg Met
        435                 440                 445
Ala Val Lys Ser Ile Ile Asn Lys Lys Ile Glu Val Val Lys Thr Leu
    450                 455                 460
Ala Ala Ser Leu Phe Met Ala Ala Ser Val Tyr Gly Met Lys Tyr Tyr
465                 470                 475                 480
Leu Leu Tyr Ser Asn Ala Asp Ser Arg Ile Ile Phe Ile Ile Lys Val
                485                 490                 495
Phe Ile Val Ile Leu Leu Gly Val Val Val Tyr Ser Ile Met Asn Ile
            500                 505                 510
Ile Leu Arg Asn Asp Asp Phe Val Ser Phe Ile Ser Met Phe Lys Gly
        515                 520                 525
Arg Leu Ser Arg Lys Phe Leu Lys Lys
    530                 535

<210> SEQ ID NO 67
<211> LENGTH: 23
<212> TYPE: DNA
<213> ORGANISM: Brachyspira hyodysenteriae

<400> SEQUENCE: 67
aaacgtttat attttatttt atc                                          23

<210> SEQ ID NO 68
<211> LENGTH: 18
<212> TYPE: DNA
<213> ORGANISM: Brachyspira hyodysenteriae

<400> SEQUENCE: 68
aaacttccaa gtgatacc                                                18

<210> SEQ ID NO 69
<211> LENGTH: 20
<212> TYPE: DNA
<213> ORGANISM: Brachyspira hyodysenteriae

<400> SEQUENCE: 69
aaatataaac ctacaagcag                                              20

<210> SEQ ID NO 70
<211> LENGTH: 23
<212> TYPE: DNA
<213> ORGANISM: Brachyspira hyodysenteriae

<400> SEQUENCE: 70
aatatttcag ttaatctaaa atc                                          23
```

<210> SEQ ID NO 71
<211> LENGTH: 24
<212> TYPE: DNA
<213> ORGANISM: Brachyspira hyodysenteriae

<400> SEQUENCE: 71
actttaatct tgtattaat tttg                                            24

<210> SEQ ID NO 72
<211> LENGTH: 23
<212> TYPE: DNA
<213> ORGANISM: Brachyspira hyodysenteriae

<400> SEQUENCE: 72
ttgttttaat ttgataatat cag                                            23

<210> SEQ ID NO 73
<211> LENGTH: 29
<212> TYPE: DNA
<213> ORGANISM: Brachyspira hyodysenteriae

<400> SEQUENCE: 73
aaaaaaatta ttttattaat atttatatt                                      29

<210> SEQ ID NO 74
<211> LENGTH: 23
<212> TYPE: DNA
<213> ORGANISM: Brachyspira hyodysenteriae

<400> SEQUENCE: 74
ttctcttata atctttacag ttg                                            23

<210> SEQ ID NO 75
<211> LENGTH: 19
<212> TYPE: DNA
<213> ORGANISM: Brachyspira hyodysenteriae

<400> SEQUENCE: 75
catatttctg gtgattctc                                                 19

<210> SEQ ID NO 76
<211> LENGTH: 27
<212> TYPE: DNA
<213> ORGANISM: Brachyspira hyodysenteriae

<400> SEQUENCE: 76 tttttgata aataagtttt ttatttg                                         27

<210> SEQ ID NO 77
<211> LENGTH: 28
<212> TYPE: DNA
<213> ORGANISM: Brachyspira hyodysenteriae

<400> SEQUENCE: 77
tttaatactc ctatattatt aattattt                                       28

<210> SEQ ID NO 78
<211> LENGTH: 18
<212> TYPE: DNA
<213> ORGANISM: Brachyspira hyodysenteriae

<400> SEQUENCE: 78

```
aaggagaatc accagaaa                                            18

<210> SEQ ID NO 79
<211> LENGTH: 23
<212> TYPE: DNA
<213> ORGANISM: Brachyspira hyodysenteriae

<400> SEQUENCE: 79
aatgatatta ttaaagtgat aaa                                      23

<210> SEQ ID NO 80
<211> LENGTH: 20
<212> TYPE: DNA
<213> ORGANISM: Brachyspira hyodysenteriae

<400> SEQUENCE: 80
aaaatctaat ataacggatt                                          20

<210> SEQ ID NO 81
<211> LENGTH: 20
<212> TYPE: DNA
<213> ORGANISM: Brachyspira hyodysenteriae

<400> SEQUENCE: 81
aaatatgctt ccattatagg                                          20

<210> SEQ ID NO 82
<211> LENGTH: 21
<212> TYPE: DNA
<213> ORGANISM: Brachyspira hyodysenteriae

<400> SEQUENCE: 82
acttttagga agaagtttaa c                                        21

<210> SEQ ID NO 83
<211> LENGTH: 25
<212> TYPE: DNA
<213> ORGANISM: Brachyspira hyodysenteriae

<400> SEQUENCE: 83
tatattttca ttatatattt attag                                    25

<210> SEQ ID NO 84
<211> LENGTH: 18
<212> TYPE: DNA
<213> ORGANISM: Brachyspira hyodysenteriae

<400> SEQUENCE: 84
ctaggcatag attttcca                                            18

<210> SEQ ID NO 85
<211> LENGTH: 28
<212> TYPE: DNA
<213> ORGANISM: Brachyspira hyodysenteriae

<400> SEQUENCE: 85
gatataatta taataatagt gttaatac                                 28

<210> SEQ ID NO 86
<211> LENGTH: 19
<212> TYPE: DNA
<213> ORGANISM: Brachyspira hyodysenteriae

<400> SEQUENCE: 86
```
ttcagtgtct gaatcattc                                                    19

<210> SEQ ID NO 87
<211> LENGTH: 23
<212> TYPE: DNA
<213> ORGANISM: Brachyspira hyodysenteriae

<400> SEQUENCE: 87
gtatgtttat atgctcagga tac                                               23

<210> SEQ ID NO 88
<211> LENGTH: 21
<212> TYPE: DNA
<213> ORGANISM: Brachyspira hyodysenteriae

<400> SEQUENCE: 88
aacagcagca ctatcttgta a                                                 21

<210> SEQ ID NO 89
<211> LENGTH: 24
<212> TYPE: DNA
<213> ORGANISM: Brachyspira hyodysenteriae

<400> SEQUENCE: 89
cagcagcaac aaataatact actg                                              24

<210> SEQ ID NO 90
<211> LENGTH: 25
<212> TYPE: DNA
<213> ORGANISM: Brachyspira hyodysenteriae

<400> SEQUENCE: 90
tgaatataaa caccttctct caaag                                             25

<210> SEQ ID NO 91
<211> LENGTH: 26
<212> TYPE: DNA
<213> ORGANISM: Brachyspira hyodysenteriae

<400> SEQUENCE: 91
aaaatgtcat tggtaactac tgtaag                                            26

<210> SEQ ID NO 92
<211> LENGTH: 25
<212> TYPE: DNA
<213> ORGANISM: Brachyspira hyodysenteriae

<400> SEQUENCE: 92
cttgataatc tgcctttaaa catac                                             25

<210> SEQ ID NO 93
<211> LENGTH: 23
<212> TYPE: DNA
<213> ORGANISM: Artificial Sequence
<220> FEATURE:
<223> OTHER INFORMATION: pTrcHis-F primer

<400> SEQUENCE: 93
caatttatca gacaatctgt gtg                                               23

<210> SEQ ID NO 94
<211> LENGTH: 23
<212> TYPE: DNA

```
<213> ORGANISM: Artificial Sequence
<220> FEATURE:
<223> OTHER INFORMATION: pTrcHis-R primer

<400> SEQUENCE: 94
tgcctggcag ttccctactc tcg                                             23
```